United States Patent [19]
Hunter et al.

[11] Patent Number: 5,811,255
[45] Date of Patent: Sep. 22, 1998

[54] APPARATUS AND METHOD FOR ANAEROBIC RESPIROMETRY

[75] Inventors: Robert M. Hunter; Frank M. Stewart, both of Gallatin, Mont.

[73] Assignee: Yellowstone Environmental Science, Bozeman, Mont.

[21] Appl. No.: 530,539

[22] Filed: Sep. 20, 1995

[51] Int. Cl.$^6$ .............................. C12Q 1/02; C12M 1/34
[52] U.S. Cl. .................... 435/29; 435/287.1; 435/287.5; 210/614
[58] Field of Search .............................. 435/288.1, 288.6, 435/287.1, 287.5, 303.2, 801, 300.1, 4, 29, 34, 37, 39; 210/603, 614; 422/79; 436/62

[56] References Cited

U.S. PATENT DOCUMENTS

| | | | |
|---|---|---|---|
| 4,352,886 | 10/1982 | Pillis et al. | 435/262 |
| 4,986,916 | 1/1991 | Hickey | 210/603 |
| 5,024,949 | 6/1991 | Hegeman et al. | 435/262 |
| 5,125,262 | 6/1992 | Garg | 73/19.12 |
| 5,228,995 | 7/1993 | Stover | 210/603 |
| 5,342,769 | 8/1994 | Hunter et al. | 435/166 |
| 5,470,745 | 11/1995 | Beteau et al. | 435/286.1 |

FOREIGN PATENT DOCUMENTS

| | | | |
|---|---|---|---|
| 212984 | 8/1984 | Germany | 435/287.1 |
| 2-171177 | 7/1990 | Japan | 435/287.1 |
| 662579 | 5/1979 | U.S.S.R. | 435/286.1 |
| 93/16169 | 8/1993 | WIPO | 435/286.1 |

OTHER PUBLICATIONS

Dang et al., "Evaluation of biodegradation kinetic with respirometric data." Research Journal WPCF, vol. 61, No. 11/12 (Nov./Dec.–1989).

Hunter et al.(May 1995). Anaerobic Respirometer for Bioremediation Process Design. Phase I Final Technical Report prepared for NASA. Yes Inc.

Abd–el–Malek, Y. & Rizk, S.G.(1963). Bacterial sulphate reduction and the development of alkalinity. I. Experiments with synthetic media. *J. Appl. Bacteriol.*, 26, 7–13.

Aeckersberg, F., Bak, F., & Widdel, F. (1991). Anaerobic oxidation of saturated hydrocarbons to $CO^2$ by a new type of sulfate–reducing bacterium. *Arch. Microbiol.*, 1 56, 5–14.

Andrews, J.F. (1968). A mathematical model for the continuous culture of microorganisms utilizing inhibitory substrates. *Biotech. Bioeng.*, 10, 707–723.

Bak, F. & Widdel, F. (1986). Anaerobic degradation of phenol derivatives by *desulfobacterium phenolicum* sp. nov. *Arch. Microbiol.*, 146, 177–180.

Bakker, G. (1977). Anaerobic degradation of aromatic compounds in the presence of nitrate. *FEMS Microbiol. Lett.*, 1, 103–108.

Belay, N. & Daniels, L. (1987). Production of ethane, ethylene, and acteylene from halogeneated hydrocarbons by methanogenic bacteria. *Appl. Environ. Microbiol.*, 53, 1604–1610.

Beller, H.R., Reinhard, M., & Grbi–Gali , D. (1992). Metabolic by–products of anaerobic toluene degradation by sulfate–reducing enrichment cultures. *Appl. Environ. Microbiol.*, 58, 3193–3195.

(List continued on next page.)

*Primary Examiner*—William H. Beisner

[57] ABSTRACT

An apparatus and method for anaerobic and aerobic respirometry. The apparatus and method provide for automatically collecting and analyzing the data required to calibrate mathematical models for bioprocesses that involve anaerobic respiration, aerobic respiration and dehalogenation. Dissolved electron-acceptor concentrations and/or product concentrations and/or headspace pressures are automatically monitored during the progress of a biotransformation occurring in a batch reactor to produce a data set. The data set is analyzed to derive intrinsic kinetic parameters and stoichiometric coefficients. The cultures biocatalyzing the oxidation-reduction reactions of interest may be aerobic, denitrifying (e.g., nitrate-reducing), sulfate reducing and/or methanogenic. The models thus developed may be used for design of wastewater treatment or bioremediation processes.

19 Claims, 12 Drawing Sheets

OTHER PUBLICATIONS

Beller, H.R., Grbic–Galic, D., & Reinhard, M. (1992). Microbial degradation of toluene under sulfate–reducing conditions and the influence of iron on the process. *Appl. Environ. Microbiol.*, 58, 786–793.

Bossert, I.D. & Young, L.Y. (1986). Anaerobic oxidation of p–cresol by a denitrifying bacterium. *Appl. Environ. Microbiol.*, 52, 1117–1122.

Bossert, I.D., Rivera, M.D., & Young, L.Y. (1986), p–Cresol biodegradation under denitrifying conditions: Isolation of a bacterial coculture. *FEMS Microbiology Ecology*, 38, 313–319.

Bouwer, E.J. & McCarty, P.L. (1983). Transformations of halogenated organic compounds under denitrification conditions. *Appl. Environ. Microbiol.*, 45, 1295–1299.

Chu, K.H., & Jewell, W.J. (1994). Treatment of tetrachloroethylene with anaerobic attached film process. *J. Environ. Eng.*, 120, 58–71.

Coetzee, C.J. & Freiser, H. (1968). *Anion–responsive electrodes based on ion association extraction systems.* Tucson, Az: The University of Arizona, Department of Chemistry.

Coschigano, P.W., Häggblom, M.M., & Young, L. Y. (1994). Metabolism of both 4–Chlorobenzoate and Toluene under denitrifying conditions by a constructed bacterial strain. *Appl. Environ. Microbiol.*, 60, 989–995.

Criddle, C.S., DeWitt, J.T., & McCarty, P.L. (1990). Reductive dehalogenation of carbon tetrachloride by *Escherichia coli* K–12. *Appl. Environ. Microbiol.*, 56, 3247–3254.

Cox, R.P., Miller, M., Nielsen, J.B., Nielson, M., & Thomsen, J.K. (1989). Continuous turbidometric measurements of microbial cell density in bioreactors using a light–emmiting diode and a photodiode. *J. Microbiol. Meth.*, 10, 25–31.

DeBruin, W.P., Kotterman, J.J., Posthumus, M.A., Schraa, G., & Zehnder, A.J.B. (1992). Complete biological reductive transformation of tetrachlorethene to ethane. *Appl. Envorin. Microbiol.*, 58, 1996–2000.

DiStefano, T.D., Gossett, J.M., & Zinder, S.H. (1992). Hydrogen as an electron donor for dechlorination of tetrachloroethene by an anaerobic mixed culture. *Appl. Environ. Microbiol.*, 58, 3622–3629.

Edwards, E.A. & Grbi –Gali (1994). Anaerobic degradation of toluene and o–xylene by a methanogenic consortium. *Appl. Environ. Microbiol.*, 60, 313–322.

Edwards, E.A., Wills, L.E., Reinhard, M., & Grbic–Galic, D. (1992). Anaerobic degradation of toluene and xylene by aquifer microorganisms under sulfate–reducing conditions. *Appl. Envorin. Microbiol.*, 58, 794–800.

Edwards, E.A. & Grbic–Galic, D. (1992). Complete mineralization of benzene by aquifer microorganisms under strictly anaerobic conditions. *Appl. Environ. Microbiol.*, Aug., 2663–2666.

Edwards, E.A., Edwards, A.M., & Grbi–gali , D. (1994). A method for detection of aromatic metabolites at very low concentrations: Application to detection of metabolites of anaerobic toluene degradation. *Appl. Environ. Microbiol.*, 60, 323–327.

Egli, C. Scholtz, R., Cook, A.M., & Leisinger, T. (1987). Anaerobic dechlorination of tetrachloromethane and 1,2–dichloroethane to degradable products by pure cultures of *Desulfobacterium* sp. and *Methanobacterium* sp. *FEMS Microbiol. Lett.*, 43, 257–261.

Egli, C., Tschan, T., Scholtz, R., Cook, A.M., & Leisinger, T. (1988). Transformation of tetrachloromethane to dichloromethane and carbon dioxide by *Acetobacterium woodii*. *Appl. Environ. Microbiol.*, 54, 2819–2824.

Egli, C., Stromeyer, S., Cook, A.M., & Lesinger, T. (1990). Transformation of tetra–and trichloromethane to CO2 by anaerobic bacteria is a non–enzymic process. *FEMS Microbiol. Lett.*, 68, 207–212.

Evans, P.J., Mang, D.T., Kim, K.S., & Young, L.Y. (1991). Anaerobic degradation of toulene by a denitrifying bacterium. *Appl. Environ. Microbiol.*, 57, 1139–1145.

Evans, P.J., Mang, D.T., & Young, L.Y. (1991). Degradation of toluene and m–xylene and transformation of o–xylene by denitrifying enrichment cultures. *Appl. Environ. Microbiol.*, 57, 450–454.

Evans, P.J., Ling, W. Goldschmidt, B., Ritter, E.R., & Young, L.Y. (1992). Metabolites formed during anaerobic transformation of toluene and 0–xylene and their proposed relationship to the initial steps of toluene mineralization. *Appl. Environ. Microbiol.*, Feb., 496–501.

Fathepure, B.Z., Nengu, J.P., & Boyd, S.A. (1987). Anaerobic bacteria that dechlorinate perchloroethene. *Appl. Environ. Microbiol.*, 53, 2671–2674.

Fatherpure, B.Z. & Boyd, S.A. (1988). Dependence of tetachloroethylene dechlorination on methanogenic substate consumption by *Methanosarcina* sp. strain DCM. *Appl. Environ. Microbiol.*, 54, 2976–2980.

Fatherpure, B.A. & Boyd, S.A. (1988), Reductive dechlorination of perchloroethylene and the role of methanogens. *FEMS Microbiol. Lett.*, 49, 149–156.

Freedman, D.L. & Gossett, J.M. (1989). Biological reductive dechlorination of tetrachloroethylene and trichloroethylene to ethylene under methanogenic conditions. *Appl. Environ. Microbiol.*, 55, 2144–2151.

Fries, M.R., Zhou, J., Chee–Sanford, J., & Tiedje, J.M. (1994). Isolation characterization, and distribution of denitrifying toluene degraders from a variety of habitats. *Appl. Environ. Microbiol.*, 60, 2802–2810.

Gibson, S.A. & Sewell, G.W. (1992). Stimulation of reductive dechlorination of tetrachloroethene in anaeroic aquifer microcosms by addition of short–chain organic acids or alcohols. *Appl. Environ. Microbiol.*, 58, 1392–1393.

Grady, C.P.L., Jr. (1990). Biodegradation of toxic organics: status and potential. *J. Environ. Eng.*, 116, 805–828.

Grady, C.P.L., Jr. (1989). Biological detoxification of hazardous wastes: What do we know? What should we know? In Y.C. Wu (Ed.), *Proceedings of the International Conference on Physiochemical and Biological Detoxificationof Hazardous Wastes*, (pp. 3–16). Lancaster, Pennsylvania: Technomic.

Grady, C.P.L., Jr., Aichinger, G., Cooper, S.F., & Naziruddin, M. (1989). Biodegradation kinetics for selected toxic/hazardous organic compounds. *Hazardous Waste Treatment: Biosystems for Pollution Control*, Pittsburgh, Pennsylvania: Air and Waste Management Association, 141–153.

Grbic–Galic, D. & Vogel, T.M. (1987). Transformation of toluene and benzene by mixed methanogenic cultures. *Appl. Environ. Microbiol.*, 53, 254–260.

Häggblom, M.M., Rivera, M.D., Bosser, I.D., Rogers, J.E., & Young, L.Y. (1990). Anaerobic biodegradation of para–cresol under three reducing conditions. *Microbial Ecology*, 20, 141–150.

Han, K. & Levenspiel, O. (1988). Extended monod kinetics for substrate, product, and cell inhibition. *Biotech. Bioeng.*, 32, 430–437.

Heddle, J.F. (1978). Rspirometric oxygen demand tests for waste waters. *Water & Soil Misc. Publication, No. 29*, 29–34.

Holliger, C., Schraa, G., Stams, A.J.M., & Zehnder, A.J.B. (1992). Enrichment and properties of an anaerobic mixed culture reductively dechlorinating 1,2,3–trichlorobenzene to 1,3–dichlorobenzene. *Appl. Environ. Microbiol.*, May, 1636–1644.

Hooker, B.S., Skeen, R.S., & Petersen, J.N. (1994). Biological destruction of Cc14: II. Kinetic modeling. *Biotech. Bioeng., 44*, 211–218.

Hsiung, K.P. Kuan, S.S., & Guilbault, G.G. (1976). An ion–selective electrode for methylamine. *Analytica Chimica Acta, 84*, 15–22.

Hu, L.Z. & Shieh, W.K. (1987). Anoxic biofilm degradation of monocyclic aromatic compounds. *Biotech. Bioeng., 30*, 1077–1083.

Hunter, R.M. (1989). Biocatalyzed partial demineralization of acidic metal–sulfate solutions (Doctoral dissertion, Montana State University), *University Microfilms International.*

Hunter, R.M. & Stewart, F.M. (1992). *Biomimetoc Process for Hazardous Waste Remediton*. Phase I Final Technical Report prepared for Defense Advanced Research Projects Agency. Yes Inc.

Hutchins, S.R. (1991). Biodegradation of monoaromatic hydrocarbons by aquifer microorganisms using oxygen, nitrate, or nitrous oxide as the terminal electron acceptor. *Appl. Environ. Microbiol.*, Aug., 2403–2407.

James, H., Carmack, G., & Freiser, H. (1972). Coated wire ion selective electrodes *Analytical Chemistry, 44*, 856–857.

Kästner, M. (1991). Reductive dechlorination of tri–and tetrachloroethylenes depends on transition from aerobic to anaerobic conditions. *Appl. Environ. Microbiol., 57*, 2039–2046.

Khoury, N., Dott, W., & Kämpfer, P. (1992). Anaerobic degradation of p–cresol in batch and continuous cultures by a denitrifying bacterial consortium. *Appl. Microbiol. Biotech., 37*, 529–531.

Khoury, N., Dott, W., & Kämpfer, P. (1992). Anaerobic degradation of phenol in batch and continuous cultures by a denitrifying bacterial consortium. *Appl. Microbiol. Biotech., 37*, 524–528.

Kleopfer, R.D., Easley, D.M., Haas, B.B. Jr., Deihl, T.G., Jackson, DE., & Wurrey, C.J. (1985). Anaerobic degradation of trichloroethylene in soil. *J. Environ. Sci. Tech., 19*, 277–280.

Krone, U.E., Laufer, K., & Thauer, R.K. (1989). Coenzyme F430 as a possible catalyst for the reductive dehalogenation of chlorinated C1 hydrocarbons in methanogenic bacteria. *Biochem., 28*, 10061–10065.

Krone, U.E., & Thauer, R.K. (1992). Dehalogenation of trichlorofluoromethane (CFC–11) by *Methanosarcina barkeri*. *FEMS Microbiol. Lett., 90.* 201–204.

Kuhn, E.P., Zeyer, J., Eicher, P, & Schwarzenbach, R.P. (1988). Anaerobic degradation of alkylated benzenes in denitrifying laboratory aquifer columns. *Appl. Environ. Microbiol., 54*, 490–496.

Kuhn, E.P., Townsend, G.T., & Suflita, J.M. (1990). Effect of sulfate and organic carbon supplements on reductive dehalogenation of chloroanilines in anaerobic aquifer slurries *Appl. Environ. Microbiol., 56*, 2630–2637.

Luong, J.H.T. (1987). Generalization of Monod kinetics for analysis of growth data with substrate inhibition. *Biotech. Bioeng., 29*, 242–248.

Ma, T.S. & Hassan, S.S.M. (1982). *Organic Analysis Using Ion–Selective Electrodes*. New York: Academic Press.

Major, D.W., Mayfield, C.I., & Barker, J.F. (1988). Biotransformation of benzene by dentrification in aquifer sand. *Ground Water, 26*, 8–14.

McCarty, P.L. (1971). Energetics and bacterial growth. In S.D. Faust and J.V. Hunter (Eds.), *Organic Compounds in Aquatic Enviroments*. New York: Marcel Dekker, Inc.

Molin, G. & Nilssan, I. (1985). Degradation of phenol by *Pseudomonas putida* ATCC 11172 in continuous culture at different ratios of biofilm surface to culture volume. *Appl. Environ. Microbiol., 50*, 946–950.

Montgomery, H.A.C. (1967). The determination of biochemical oxygen demand by respirometric methods. *Water Research, 1*, 631–662.

Mulchandani, A. & Luong, J.H.T. (1989). Microbial inhibition kinetics revisited. *Enzyme Microbiology and Technology, 11*, 66–73.

Naziruddin, M. (1989). *Determination of Biodegradation Kinetics of Volatile Organic Compounds through use of Respirometry*. Master's Thesis, Clemson University, Clemson, SC.

Nelson, M.J., Montgomery, S.O., Mahaffey, W.R., & Pritchard, P.H. (1987). Biodegradation of trichloroethylene and involvement of an aromatic biodegradative pathway. *Applied and Enviromental Microbiology, 53*, 949–954.

Oldenhuis, R., Oedzes, J.Y., Van Der Waarde, J.J., & Janssen, D.B. (1991). Kinetics of chlorinated hydrocarbon degradation by *Methylosinus trichosporium* OB3b and toxicity of trichloro–ethlene. *Appl. Environ. Microbiol., 57*, 7–14.

Paris, D.F., Steen, W.C., Baughman, G.L., & Barnett, J.T., Jr. (1981). Second–order model to predict microbial degradation of organic compounds in natural waters. *Appl. Environ. Microbiol., 41*, 603–609.

Pavlostathis, S.G., & Zhuang, P. (1991) Transformation of trichloroethylene by sulfate–reducing cultures enriched from a contaminated subsurface soil. *Appl. Microbiol. Biotech., 36*, 416–420.

Petersen, J.N., Skeen, R.S., Amos, K.M., & Hooker, B.S. (1994). Biological destruction of CC14: I. Experimental design and data. *Biotech. Bioeng., 43*, 521–528.

Pungor, E. & Havas, J. (1966). Electrochemical behaviour of ionite and complexonites membrane electrodes. *Acta Chimica Academiae Scientiarum Hungaricae Tomus, 50*, 77–104.

Rabus, R., Nordhaus, R., Ludwig, W., & Widdel, F. (1993). Complete oxidation of toluene under strictly anoxic conditions by a new sulfate–reducing bacterium. *Appl. Environ. Microbiol., 59*, 1444–1451.

Seyfried, B., Glod, G., Schocher, R., Tschech, A., & Zeyer, J. (1994). Initial reactions in the anaerobic oxidation of toluene and m–xylene by denitrifying bacteria. *Appl. Environ. Microbiol., 60*, 4047

Shamat, N.A. & Maier, W.J. (1980). Kinetics of biodegradation of chlorinated organics. *Jounral WPCF, 52*, 2158–2166.

Skeen, R.S., Truex, M.J., Persen, J.N., & Hill, J.S. (1994). A batch reactor for monitoring process dynamics biodegradation of volatile organics. *Enviromental Progress, 13*, 174–176.

Suidan, M.T., Najm, I.M., Pfeffer, J.T., & Wang, Y.T. (1988). Anaerobic biodegradation of phenol: inhibition kinetics and system stability. *J. Environ. Eng., 114*, 1359–1376.

Tandol, V., DiStefano, T.D., Bowser, P.A., Gossett, J.M., & Zinder, S.H. (1994). Reductive dehalogenation of chlorinated ethenes and hologenated ethanes by a high-rate anaerobic encrichment culture. *Environ. Sci. Technol., 28,* 973–979.

Thomsen, J.K., Geest, T., & Cox, R.P. (1994). Mass spectrometric studies of the effect of pH on the accumulation of intermediates in denitrification by *Paracoccus denitrificans. Appl. Environ. Microbiol., 60.* 536–541.

Tschech, A. & Fuchs, G. (1987). Anaerobic degradation of phenol by pure cultures of newly isolated denitrifying pseudomonads. *Arch. Microbiol., 148,* 213–217.

Umbreit, W.W., Burris, R.H., & Stauffer, J.F. (1964). Manometric techniques and related methods for the study of tissue metabolism. Minneapolis, MN: Burgess Publishing Co.

Vogel, T.M. & McCarty, P.L. (1985). Biotransformation of tetrachloro–ethylene to trichloroehtylene, vinyl chloride, and carbon dioxide under methanogenic conditions. *Appl. Environ. Microbiol., 49,* 1080–1083.

Zache & Rehm. (1989). Degradation of phenol by a coimmobilized entrapped mixed culture. *Appl. Microbial Biotech., 30,* 426–432.

Almeida, J.S., Reis, M.A.M., & Carrondo, M.J.T. (1995). Competition between nitrate and nitrite reduction in denitrification by Pseudomonas fluorescens. *Biotech. Bioeng., 46,* 476–484.

APPARATUS AND METHOD FOR ANAEROBIC RESPIROMETRY

STATEMENT AS TO RIGHTS IN INVENTIONS MADE UNDER FEDERALLY-SPONSORED RESEARCH AND DEVELOPMENT

This invention was made with Government support under Small Business Innovation Research Contract No. NAS10-12165 awarded by the National Aeronautics and Space Administration. The Government has certain rights in the invention.

BACKGROUND OF THE INVENTION

The background of the invention is set forth in two parts: the field of the invention and the description of related art.

1. Field of the Invention

This invention is related to anaerobic and aerobic respirometry. In particular, it relates to an apparatus and method for respirometry involving aerobic, denitrifying, iron-reducing, sulfate-reducing and/or methanogenic microbial cultures.

2. Description of Related Art

Most productive research on new biotechnologies for hazardous waste remediation is conducted from a reactor engineering perspective. Grady explained this phenomenon as follows (Grady, C. P. L., Jr. *Biological detoxification of hazardous wastes: What do we know? What should we know?* In Y. C. Wu (Ed.), *Proceedings of the International Conference on Physiochemical and Biological Detoxification of Hazardous Wastes*. Lancaster, Pa.: Technomic, 1989, pp. 3–16.):

"Many of the major advances in pollution control technology have come from the application of reactor engineering to wastewater treatment systems. Reactor engineering is based on the premise that, if the kinetics of a reaction can be expressed mathematically, then it is possible to investigate the impact of reactor type and configuration on the extent of reaction through application of mathematical models that incorporate both transport and reaction terms."

The reactor engineering approach involves gathering the information required to mathematically model various process options. Reliance on process modeling offers a number of advantages. First, development of the model in the early stages of the project can facilitate design of the experimental apparatus and procedures. Second, a model provides a framework for understanding the microbiology of the system under study. Finally, a calibrated model is a valuable tool for investigating applications for the knowledge gained during the research and the resulting scale-up of that knowledge.

Recent research has revealed the promise of novel bioremediation schemes that rely, either in part or totally, on anaerobic processes. These include metabolic processes (such as aerobic respiration, denitrification and sulfate reduction) and/or methogenesis and/or cometabolic processes (such as reductive dechlorination), (Hunter et al. *Biomimetic process for hazardous waste remediation*. Phase I Final Technical Report prepared for Defense Advanced Research Projects Agency, Yellowstone Environmental Science, Inc. (YES), 1992).

Biotransformation of some compounds of interest applicable to bioremediation process design have been found to occur under denitrifying conditions. Bakker disclosed that a mixed culture can degrade phenol, o-cresol, m-cresol and p-cresol under anaerobic conditions in the presence of nitrate as the terminal electron acceptor (Bakker, G. *Anaerobic degradation of aromatic compounds in the presence of nitrate, FEMS Microbiology Letters*, 1, 103–108, 1977). Pure cultures of three Gram-negative, slightly curved, monotrichously flagellated rods, including strain DSM 981, were capable of phenol decomposition under anaerobic conditions in the presence of nitrate. Pillis and Davis (in U.S. Pat. No. 4,352,886, Oct. 5, 1982) disclosed a mutant microorganism, *Pseudomonas putida* CB-173, that is capable of degrading phenolics at a temperature as low as 1° C. to 4° C. at a faster rate than known *Pseudomonas putida* type strains, and they disclosed a process for treating wastewater containing phenolics using the mutant microorganism strain. Molin and Nilssan disclosed a pseudomonad that is capable of growing in continuous culture with phenol as the only carbon and energy source under aerobic conditions (Molin, G. & Nilssan, I. *Degradation of phenol by Pseudomonas putida ATCC* 11172 *in continuous culture at different ratios of biofilm surface to culture volume, Applied and Environmental Microbiology*, 50, 946–950, 1985). Bossert et al. disclosed two bacterial species which utilize p-cresol as the sole source of carbon when grown in a co-culture of both microorganisms under nitrate-reducing conditions (Bossert, I. D., Rivera, M. D., & Young, L. Y. *p-Cresol biodegradation under denitrifying conditions: Isolation of a bacterial coculture, FEMS Microbiology Ecology*, 38, 313–319, 1986). A syntrophic relationship was documented. Bossert and Young disclosed metabolism of p-cresol as a sole carbon source under nitrate-reducing conditions by the denitrifying bacterial isolate PC-07 (Bossert, I. D. & Young, L. Y. *Anaerobic oxidation of p-cresol by a denitrifying bacterium, Applied and Environmental Microbiology*, 52, 1117–1122, 1986). Nitrate was required as the external electron acceptor and was reduced to molecular nitrogen. Phenol, toluene, o-cresol and m-cresol were not metabolized by the isolate.

Tschech and Fuchs disclosed several strains of bacteria which, in the absence of molecular oxygen, oxidized phenol to carbon dioxide with nitrate as the terminal electron acceptor (Tschech, A. & Fuchs, G. *Anaerobic degradation of phenol by pure cultures of newly isolated denitrifying pseudomonads, Archives of Microbiology*, 148, 213–217, 1987). The bacteria were facultatively-anaerobic Gram-negative rods. Hu and Shieh disclosed removal of phenol and o-cresol under anoxic conditions in an upflow biofilter with nitrate as the electron acceptor (Hu, L. Z. & Shieh, W. K. *Anoxic biofilm degradation of monocyclic aromatic compounds, Biotechnology and Bioengineering*, 30, 1077–1083, 1987). O-cresol was removed at a slower rate. Major et al. disclosed the biodegradation of benzene, toluene and the isomers of xylene (BTX) in anaerobic batch microcosms containing shallow aquifer material. Denitrification was confirmed by nitrous oxide accumulation after acetylene blockage of nitrate reductase (Major, D. W., Mayfield, C. I., & Barker, J. F. *Biotransformation of benzene by denitrification in aquifer sand, Ground Water*, 26, 8–14, 1988). They proposed that the addition of nitrate to gasoline-contaminated aquifers would serve as an adjunct to current remedial techniques.

Kuhn et al. disclosed mineralization of toluene, m-xylene, m-cresol and p-cresol in an anaerobic laboratory aquifer column operated under continuous-flow conditions with nitrate as an electron acceptor (Kuhn, E. P., Zeyer, J., Eicher, P, & Schwarzenbach, R. P. *Anaerobic degradation of alkylated benzenes in denitrifying laboratory aquifer columns, Applied and Environmental Microbiology*, 54, 490–496, 1988). Benzene was not metabolized. Kuhn et al. also confirmed the mineralization of toluene, m-xylene, m-cresol and p-cresol by denitrifiers. Zache and Rehm disclosed the degradation of phenol by a defined mixed culture consisting of *Pseudomonas putida F8* and *Cryptococcus elinovii H1* under aerobic conditions (Zache & Rehm *Degradation of phenol by a coimmobilized entrapped mixed culture, Applied Microbial Biotechnology*, 30, 426–432, 1989). Häggblom et al. disclosed metabolism of p-cresol under denitrifying conditions (Häggblom, M. M., Rivera, M. D., Bossert, I. D., Rogers, J. E., & Young, L. Y. *Anaerobic biodegradation of para-cresol under three reducing conditions, Microbial Ecology*, 20, 141–150, 1990). Phenol was utilized at a slower rate. Evans et al. isolated a denitrifying bacterium that grew on toluene as the sole source of carbon (Evans, P. J., Mang, D. T., Kim, K. S., & Young, L. Y. *Anaerobic degradation of toluene by a denitrifying bacterium, Applied and Environmental Microbiology*, 57, 1139–1145, 1991). Evans et al. documented the biotransformation of toluene, m-xylene and o-xylene under denitrifying conditions (Evans, P. J., Mang, D. T., & Young, L. Y. *Degradation of toluene and m-xylene and transformation of o-xylene by denitrifying enrichment cultures, Applied and Environmental Microbiology*, 57, 450–454, 1991). No transformation of benzene or p-xylene was reported. Hegeman and Nickens (in U.S. Pat. No. 5,024,949, Jun. 18, 1991) disclosed bacterium of the genus Pseudomonas which utilizes a branched chain alkyl-substituted aromatic hydrocarbon as its sole carbon and energy source, and which is capable of substantial degradation of trichlorethylene (TCE) under aerobic conditions. The bacterium was described as being capable of denitrification, but the electron donor during denitrification is undisclosed. Also disclosed were methods utilizing the bacterium for the detoxification of TCE-contaminated material. Hutchins disclosed biodegradation of toluene, ethyl benzene, m-xylene and o-xylene under nitrate-reducing conditions. Benzene was not degraded (Hutchins, S. R. *Biodegradation of monoaromatic hydrocarbons by aquifer microorganisms using oxygen, nitrate, or nitrous oxide as the terminal electron acceptor, Applied and Environmental Microbiology*, August, 2403–2407, 1991). Evans et al. isolated a nitrate-reducing bacterium (NRB), which they named Strain T1, capable of mineralization of toluene and o-xylene (Evans, P. J., Ling, W., Goldschmidt, B., Ritter, E. R., & Young, L. Y. *Metabolites formed during anaerobic transformation of toluene and o-xylene and their proposed relationship to the initial steps of toluene mineralization, Applied and Environmental Microbiology*, February, 496–501, 1992). Khoury et al. reported the anaerobic degradation of p-cresol by a denitrifying culture (Khoury, N., Dott, W., & Kampfer, P. *Anaerobic degradation of p-cresol in batch and continuous cultures by a denitrifying bacterial consortium, Applied and Environmental Biotechnology*, 37, February, 529–531, 1992) and the anaerobic degradation of phenol by a denitrifying culture (Khoury, N., Dott, W., & Kampfer, P. *Anaerobic degradation of phenol in batch and continuous cultures by a denitrifying bacterial consortium, Applied and Environmental Biotechnology*, 37, February, 524–528, 1992). Coschigano et al. disclosed the metabolism of toluene under denitrifying conditions by a constructed bacterial strain (Coschigano, P. W., Häggblom, M. M., & Young, L. Y. *Metabolism of both 4-Chlorobenzoate and Toluene under denitrifying conditions by a constructed bacterial strain, Applied and Environmental Microbiology*, 60, 989–995, 1994). Seyfried et al. reported that the denitrifying bacteria Pseudomonas sp. Strain T and Pseudomonas sp. Strain K172 oxidize toluene under denitrifying conditions, and that Strain T also oxidizes m-xylene (Seyfried, B., Glod, G., Schocher, R., Tschech, A., & Zeyer, J. *Initial reactions in the anaerobic oxidation of toluene and m-xylene by denitrifying bacteria, Applied and Environmental Microbiology*, 60, 4047–4052, 1994). Fries et al. characterized anaerobic toluene degradation under denitrifying conditions (Fries, M. R., Zhou, J., Chee-Sanford, J., & Tiedje, J. M. *Isolation, characterization, and distribution of denitrifying toluene degraders from a variety of habitats, Applied and Environmental Microbiology*, 60, 2802–2810, 1994).

Dehalogenation by denitrifying cultures has also been reported. Bouwer and McCarty documented the dechlorination of carbon tetrachloride (CT), but not 1,1,1-trichloroethane (TCA), under denitrifying conditions (Bouwer, E. J. & McCarty, P. L. *Transformations of 1- and 2-carbon halogenated aliphatic organic compounds under methanogenic conditions, Applied and Environmental Microbiology*, 45, 1286–1294, 1983). Egli et al. were unable to cause a hydrogen-oxidizing, autotrophic nitrate-reducing bacteria (NRB) to degrade CT (Egli, C., Tschan, T., Scholtz, R., Cook, A. M., & Leisinger, T. *Transformation of tetrachloromethane to dichloromethane and carbon dioxide by Acetobacterium woodii, Applied and Environmental Microbiology*, 54, 2819–2824, 1988). Criddle et al. isolated a denitrifying Pseudomonas sp. (strain KC) that is capable of dechlorinating CT (Criddle, C. S., DeWitt, J. T., Grbić-Galić, D., & McCarty, P. L. *Transformation of carbon tetrachloride by Pseudomonas sp. Strain KC under denitrification conditions. Applied and Environmental Microbiology*, 56, 3240–3246, 1990). Petersen et al. characterized a denitrifying consortium capable of transforming carbon tetrachloride (Petersen, J. N., Skeen, R. S., Amos, K. M., & Hooker, B. S. *Biological destruction of $CCl_4$: I. Experimental design and data, Biotechnology and Bioengineering*, 43, 521–528, 1994). Hooker et al. described kinetic modeling of biotransformation of carbon tetrachloride by a denitrifying consortium (Hooker, B. S., Skeen, R. S., & Petersen, J. N. *Biological destruction of $CCl4$: II. Kinetic Modeling. Biotechnology and Bioengineering*, 44, 211–218, 1994). Skeen et al. described a batch reactor used to monitor biodegradation of carbon tetrachloride by a denitrifying culture (Skeen, R. S., Truex M. J., Petersen, J. N., & Hill, J. S. *A batch reactor for monitoring process dynamics during biodegradation of volatile organics. Environmental Process*, 13, 174–177, 1994).

Bak and Widdel isolated a marine sulfate-reducing bacteria (SRB), *Desulfobacterium phenolicum*, that could anaerobically degrade phenol and phenol derivatives (Bak, F. & Widdel, F. *Anaerobic degradation of phenol derivatives by Desulfobacterium phenolicum sp. nov. Archives of Microbiology*, 146, 177–180, 1986). Aeckersberg et al. reported the anaerobic oxidation of $C_{12}$ to $C_{20}$ saturated hydrocarbons to carbon dioxide by a sulfate-reducing bacterium (Aeckersberg, F., Bak, F., & Widdel, F. *Anaerobic oxidation of saturated hydrocarbons to $CO_2$ by a new type of sulfate-reducing bacterium, Archives of Microbiology*, 156, 5–14, 1991). Edwards et al. documented the mineralization of toluene and the three isomers of xylene under sulfate-reducing conditions (Edwards, E. A., Wills, L. E., Reinhard, M., & Grbić-Galić, D. *Anaerobic degradation of toluene and xylene by aquifer microorganisms under sulfate-reducing conditions, Applied and Environmental Microbiology*, 58, 794–800, 1992). Beller et al. documented microbial degradation of toluene under sulfate-reducing conditions (Beller, H. R., Grbić-Galić, D., & Reinhard, M. *Microbial degradation of toluene under sulfate-reducing* conditions and the influence of iron on the process, Applied and Environmental Microbiology, 58, 786–793, 1992). Beller et al. identified two dead-end metabolites of toluene degradation under sulfate-reducing enrichment cultures (Beller, H. R., Reinhard, M., & Grbić-Galić, D. *Metabolic by-products of anaerobic toluene degradation by sulfate-reducing enrichment cultures, Applied and Environmental Microbiology,* 58, 3192–3195, 1992). Edwards & Grbić-Galić documented the mineralization of benzene under sulfate-reducing conditions (Edwards, E. A. & Grbić-Galić, D. *Complete mineralization of benzene by aquifer microorganisms under strictly anaerobic conditions, Applied and Environmental Microbiology,* August, 2663–2666, 1992). Rabus et al. isolated a sulfate-reducing bacterium, *Desulfobacula toluolica*, that could completely oxidize toluene (Rabus, R., Nordhaus, R., Ludwig, W., & Widdel, F. *Complete oxidation of toluene under strictly anoxic conditions by a new sulfate-reducing bacterium, Applied and Environmental Microbiology,* 59, 1444–1451, 1993).

Dechlorination reactions have been shown to occur under sulfate-reducing conditions (Kuhn, E. P., Townsend, G. T., & Suflita, J. M. *Effect of sulfate and organic carbon supplements on reductive dehalogenation of chloroanilines in anaerobic aquifer slurries, Applied and Environmental Microbiology,* 56, 2630–2637, 1990). Egli et al. established that SRB *Desulfobacterium autotrophicum* can dechlorinate TCA during metabolism of lactate, but cannot dechlorinate PCE or TCE (Egli, C., Scholtz, R., Cook, A. M., & Leisinger, T. *Anaerobic dechlorination of tetrachloromethane and 1,2-dichloroethane to degradable products by pure cultures of Desulfobacterium sp. and Methanobacterium sp, FEMS Microbiology Letters,* 43, 257–261, 1987). Egli et al. (1988) documented the dechlorination of CT by *Desulfobacterium autotrophicum*. Pavlostathis and Zhuang disclosed the transformation of TCE to cis-1,2-dichloroethylene (cDCE) by sulfate-reducing cultures (Pavlostathis, S. G., & Zhuang, P. *Transformation of trichloroethylene by sulfate-reducing cultures enriched from a contaminated subsurface soil, Applied Microbiology and Biotechnology,* 36, 416–420, 1991). Further dechlorination of cDCE was not observed.

Transformation of aromatic hydrocarbons has been shown to occur under methanogenic conditions. Grbić-Galić and Vogel disclosed the anaerobic transformation of toluene and benzene by mixed methanogenesis cultures (Grbić-Galić, D. & Vogel, T. M. *Transformation of toluene and benzene by mixed methanogenic cultures, Applied and Environmental Microbiology,* 53, 254–260, 1987). Suidan et al. documented the inhibition kinetics of the anaerobic degradation of phenol (Suidan, M. T., Najm, I. M., Pfeffer, J. T., & Wang, Y. T. *Anaerobic biodegradation of phenol: inhibition kinetics and system stability, Journal of Environmental Engineering,* 114, 1359–1376, 1988). Edwards and Grbić-Galić documented complete mineralization of toluene and o-xylene under methanogenic conditions (Edwards, E. A. & Grbić-Galić, D. *Anaerobic degradation of toluene and o-xylene by a methanogenic consortium, Applied and Environmental Microbiology,* 60, 313–322, 1994). Degradation of toluene and o-xylene in stable, mixed methanogenic cultures followed Monod kinetics. Inhibition was noted above 0.7 millimoles (mM) for o-xylene and 1.8 mM for toluene. Edwards et al. disclosed a method of detection of the metabolites of anaerobic toluene degradation (Edwards, E. A., Edwards, A. M., & Grbić-Galić, D. *A method for detection of aromatic metabolites at very low concentrations: Application to detection of metabolites of anaerobic toluene degradation, Applied and Environmental Microbiology,* 60, 323–327, 1994).

Because of the significant advantages of accomplishing dehalogenation under anaerobic conditions, many researchers have investigated methods involving anaerobic reductive dehalogenation under methanogenic conditions. Kleopfer et al. characterized reductive dechlorination of TCE in soils (Kleopfer, R. D., Easley, D. M., Haas, B. B. Jr., Deihl, T. G., Jackson, D. E., & Wurrey, C. J. *Anaerobic degradation of trichloroethylene in soil. Journal of Environmental Science and Technology,* 19, 277–280, 1985). Vogel and McCarty reported the biotransformation of PCE to TCE, DCE, VC and $CO_2$ (Vogel, T. M. & McCarty, P. L. *Biotransformation of tetrachloroethylene to trichloroethylene, dichloroethylene, vinyl chloride, and carbon dioxide under methanogenic conditions, Applied and Environmental Microbiology,* 49, 1080–1083, 1985). Freedman and Gossett described reductive dechlorination of PCE and TCE to non-toxic ethylene under methanogenic conditions (Freedman, D. L. & Gossett, J. M. *Biological reductive dechlorination of tetrachloroethylene and trichloroethylene to ethylene under methanogenic conditions, Applied and Environmental Microbiology,* 55, 2144–2151, 1989). Kästner documented the biotransformation of PCE and TCE under methanogenic conditions (Kästner, M. *Reductive dechlorination of tri- and tetrachloroethylenes depends on transition from aerobic to anaerobic conditions, Applied and Environmental Microbiology,* 57, 2039–2046, 1991). DeBruin et al. documented the complete reductive dechlorination of PCE to ethene and then to ethane under methanogenic conditions (DeBruin, W. P., Kotterman, J. J., Posthumus, M. A., Schraa, G., & Zehnder, A. J. B. *Complete biological reductive transformation of tetrachlorethene to ethane, Applied and Environmental Microbiology,* 58, 1996–2000, 1992). DiStefano et al. suggested that electron donors which cause the production of a large hydrogen pool or hydrogen gas should be selected for bioremediation of high levels of tetrachloroethylene (DiStefano, T. D., Gossett, J. M. and Zinder, S. H. *Hydrogen as an electron donor for dechlorination of tetrachloroethene by an anaerobic mixed culture, Applied and Environmental Microbiology,* 58, 3622–3629, 1992). Gibson and Sewell stimulated reductive dechlorination of PCE under methanogenic conditions by addition of short-chain organic acids or alcohols (Gibson, S. A. & Sewell, G. W. *Stimulation of reductive dechlorination of tetrachloroethene in anaerobic aquifer microcosms by addition of short-chain organic acids or alcohols, Applied and Environmental Microbiology,* 58, 1392–1393, 1992). Tandol et al. described the reductive dehalogenation of PCE to ethylene by an anaerobic enrichment culture (Tandol, V., DiStefano, T. D., Bowser, P. A., Gossett, J. M., & Zinder, S. H. *Reductive dehalogenation of chlorinated ethenes and halogenated ethanes by a high-rate anaerobic enrichment culture, Environ. Sci. Technology,* 28, 973–979, 1994).

Different methanogenic bacteria strains vary in their abilities to reductively dechlorinate chlorinated aliphatic hydrocarbons. *Methanosarcina mazei* strain S6 and *Methanosarcina_sp.* strain DCM isolated from a methanogenic enrichment growing on chlorophenol can produce TCE from PCE, while *Methanosarcina acetivorans* and a highly enriched culture of *Methanothrix sp.* also obtained from the chlorophenol enrichment do not have this ability (Fathepure, B. Z., Nengu, J. P., & Boyd, S. A. *Anaerobic bacteria that dechlorinate perchloroethene, Applied and Environmental Microbiology,* 53, 2671–2674, 1987; Fathepure, B. Z. & Boyd, S. A. *Reductive dechlorination of perchloroethylene and the role of methanogens, FEMS Microbiology Letters,* 49, 149–156, 1988; Fathepure, B. Z. & Boyd, S. A. *Dependence of tetrachloroethylene dechlo-* rination on methanogenic substrate consumption by Methanosarcina sp. strain DCM, Applied and Environmental Microbiology, 54, 2976–2980, 1988). Methanobacterium thermoautotrophicum can produce ethylene (ethene) from 1,2-dichloroethylene (1,2-dichloroethene) (Egli et al., 1987). Methanobacterium thermoautotrophicum can also dechlorinate carbon tetrachloride (tetrachloromethane), (Egli, C., Stromeyer, S., Cook, A. M., & Leisinger, T. Transformation of tetra- and trichloromethane to $CO_2$ by anaerobic bacteria is a non-enzymic process. FEMS Microbiology Letters, 68, 207–212, 1990). Methanobacterium thermoautotrophicum strain ΔH, Methanococcus deltae strain ΔLH, and Methanococcus thermolithotrophicus can produce ethane from bromoethane; ethylene from bromoethane sulfonate; 1,2-dibromoethane and 1,2-dichloroethane and acetylene from 1,2-dibromoethylene (Belay, N. & Daniels, L. Production of ethane, ethylene, and acetylene from halogenated hydrocarbons by methanogenic bacteria, Applied and Environmental Microbiology, 53, 1064–1610, 1987). Krone et al. found that cell suspensions of Methanosarcina barkeri strain Fusaro (ATCC 29787) harvested from a methanol or acetate medium could dehalogenate carbon tetrachloride to form chloroform, methylene chloride and minor amounts of methyl chloride with carbon monoxide as the electron donor (Krone, U. E., Laufer, K., & Thauer, R. K. Coenzyme $F_{430}$ as a possible catalyst for the reductive dehalogenation of chlorinated $C_1$ hydrocarbons in methanogenic bacteria, Biochemistry, 28, 10061–10065, 1989). This strain was also able to dehalogenate chloroform and methylene chloride individually under the same conditions. The strain was unable to accomplish the dehalogenation of methyl chloride. Krone and Thauer reported that cell suspensions of Methanosarcina barkeri strain Fusaro (ATCC 29787) harvested from a methanol medium were able to catalyze the reductive dehalogenation of trichlorofluoromethane (CFC-11, also known as FREON 11) to form $CHFCl_2$, CO, fluoride and minute amounts of $CH_2FCl$ in the presence of either $H_2$ or CO (Krone, U. E., & Thauer, R. K. Dehalogenation of trichlorofluoromethane (CFC-11) by Methanosarcina barkeri, FEMS Microbiology Letters, 90, 201–204, 1992). The presence of either $H_2$ or CO was necessary for dehalogenation of CFC-11 to occur. Dehalogenation of CFC-12 (dichlorodifluoro-methane) occurred at less than five percent of the rate at which CFC-11 was dehalogenated. CFC-11 completely inhibited methanogenesis in Methanosarcina barkeri strain Fusaro at the concentrations tested (6.7 μmol in a 120-ml serum bottle containing 10 ml of cell suspension). Chu and Jewell reported the dechlorination of tetrachloroethylene and trichloroethylene in an anaerobic fixed-film process under methanogenic conditions (Chu, K. H., & Jewell, W. J. Treatment of tetrachloroethylene with anaerobic attached film process, Journal of Environmental Engineering, 120, 58–71, 1994). Hunter and Stewart (in U.S. Pat. No. 5,342,769, Aug. 30, 1994) disclosed microbial dehalogenation using naturally-occurring strains of methanogenic bacteria.

Successful bioremediation processes utilize two key pieces of information: the amount of reactants and products consumed or produced, and how fast a reaction will proceed under a given set of conditions. Stoichiometry describes the amounts of reactants (such as the growth substrate or electron acceptor) and products (such as biomass and mineral products) that are consumed or produced in relationship to each other. The most common form of expressing stoichiometry is the written chemical reaction, such as in the following reaction:

$$C_7H_8 + 9O_2 \rightarrow 7CO_2 + 4H_2O \tag{1}$$

In other words, for each mole of toluene ($C_7H_8$) consumed, nine moles of oxygen are consumed, seven moles of carbon dioxide are produced and four moles of water are produced. More complex models arise when the production of biomass is considered, as will be shown later.

The second key piece of information is the knowledge of how fast a reaction will proceed under a given set of environmental conditions, and as a function of the concentration of the reacting species. This information is called kinetics. For instance, in modeling the growth of microorganisms, the Monod expression has gained widespread usage:

$$\mu = \mu_{max} S / (K_s + S) \tag{2}$$

where:

$\mu$ is the specific growth rate of the organisms, $\mu_{max}$ is the maximum specific growth rate, S is the substrate concentration, and $K_S$ is the half-saturation coefficient.

The term $\mu_{max}$ is a constant defined as the maximum value possible for $\mu$ under a specific set of conditions. $K_S$ determines how fast $\mu$ approaches $\mu_{max}$. As shown in FIG. 1, which is a plot of specific growth rate versus substrate concentration data pairs that fit the Monod equation, $K_S$ is the substrate concentration at which $\mu$ is equal to one half of $\mu_{max}$. More complex models may be used, but many of them reduce to the above "saturation-type" kinetic expression when inhibition of the reaction is not important.

In the previous two equations (equations 1 and 2), the engineer implementing the process must have clear knowledge of the values of the stoichiometric and kinetic parameters. Well-designed experiments must be carried out which clearly demonstrate the relationships between substrates consumed, electron acceptors consumed, products formed and the rates at which these reactions occur. When performed in a batch study, these coefficients (parameters) are determined by plotting one variable against another and calibrating kinetic and stoichiometric models so that they produce the least deviation of the model from the experimental data. Parameter values which produce the smallest deviation are then used in further scale-up and design of bioremediation processes.

While anaerobic bioprocesses such as those described above offer great promise as steps in engineering bioremediation processes, a significant constraint to the design and scale-up of such processes is the lack of kinetic and stoichiometric parameter data upon which to base reliable process models. Unfortunately, in the instance of anaerobic processes, because of the challenges presented by: 1) excluding oxygen from small experimental reactors, 2) substrate volatility and 3) substrate and product toxicity and gas generation, little experimental work has been done to quantify the intrinsic kinetic rates of important anaerobic and anoxic microorganisms and consortia. The work that has been done has proven to be labor intensive and time consuming.

For example, in the prior art, batch reactor studies are often used to generate the data upon which model parameter estimates can be based. A number of experiments are run at different initial substrate concentrations to assess biomass growth rates at different initial substrate concentrations. In this way, preliminary plots of biomass concentration versus time, such as those illustrated in FIG. 2, may be developed. Such plots can reveal if substrate inhibition is occurring.

Typically, biomass concentrations are monitored (by manually taking samples and analyzing these samples for biomass concentration or a proxy for biomass concentration) during an experimental run at a selected initial substrate concentration. Biomass concentration data for each run are plotted against time on graphs similar to the example shown in FIG. 2. Analysis of such graphs can reveal if substrate inhibition is occurring.

The data obtained from these experiments can be plotted on a series of biomass concentration versus time curves. The data (see FIG. 3) or their natural logarithms (see FIG. 4) can be plotted. As noted on FIG. 3, analysis of the data from each experiment (started at a given initial substrate concentration) reveals that the given substrate concentration produces biomass growth at a certain specific growth rate. A variety of linearized versions of the Monod equation can be plotted to determine $\mu_{max}$ and $K_s$. For example, in the Hofstee form shown on FIG. 5, D/S or (D+b)/S is plotted against D or (D+b) and the result is a straight line with slope $1/K_s$ and ordinate intercept $\mu_{max}/K_s$. In situations in which substrate inhibition is occurring and in which S is much greater than $K_s$, plots of the reciprocal of the specific growth rate, $\mu$, versus the initial (or average) substrate concentration, S, are then analyzed as shown on FIG. 6 to determine $\mu_{max}$ and $K_i$. From this simple example, it is apparent why the process is very time consuming and labor intensive. Furthermore, relatively large errors (uncertainty) are associated with analytical determinations of biomass at relatively low biomass concentrations typically associated with anaerobic biodegradation of inhibitory compounds in batch experiments.

Because the data required to evaluate kinetic parameters must be taken over time, the prior art contains other examples of automated approaches to data acquisition. Cox et al. (Cox, R. P., Miller, M., Nielsen, J. B., Nielson, M., & Thomsen, J. K. *Continuous turbidometric measurements of microbial cell density in bioreactors using a light-emitting diode and a photodiode, Journal of Microbiological Methods*, 10, 25–31, 1989), Iversen et al. (Iversen, J. J. L., Nielsen, M., & Cox, R. P. *Design and performance of a simple inexpensive modular laboratory-scale bioreactor, Biotech. Educ.*, 1, 11–15, 1989) and Thomsen et al. (Thomsen, J. K., Geest, T., & Cox, R. P. *Mass spectrometric studies of the effect of pH on the accumulation of intermediates in denitrification by Paracoccus denitrificans, Applied and Environmental Microbiology*, 60, 536–541, 1994) described use of continuous turbido-metric measurements of microbial cell density to evaluate kinetic parameters. With this approach, cell concentration was continually monitored by circulating the culture through a measuring chamber with a light-emitting diode-photodiode. The approach has been used to study denitrification.

Respirometry has long been a useful tool in bioremediation process research. Reviews of the field of respirometry have been published by Jenkins (Jenkins, D. *The use of manometric methods in the study of sewage and trade wastes.* In *Wastewater Treatment*, P. C. G. Issac (Ed.). Permagon Press, 1960), Montgomery (Montgomery, H. A. C. *The determination of biochemical oxygen demand by respirometric methods, Water Research*, 1, 631–662, 1967), Steinecke (Steinecke, N. *Direct determination of the BOD, GWF-Wasser/Abwasser*, 117, 454–461, 1976) and Heddle (Heddle, J. F. *Respirometric oxygen demand tests for waste waters, Water & Soil Misc. Publication*, No. 29, 29–34, 1978). Theoretical and practical aspects of aerobic electrolytic respirometry, wherein oxygen is the electron acceptor, were described by Grady et al. (Grady, C. P. L., Jr., Aichinger, G., Cooper, S. F., & Naziruddin, M. *Biodegradation kinetics for selected toxic/hazardous organic compounds. Hazardous Waste Treatment: Biosystems for Pollution Control*, Pittsburgh, Pa.: Air and Waste Management Association, 141–153, 1989) and Naziruddin (Naziruddin, M. *Determination of Biodegradation Kinetics of Volatile Organic Compounds through Use of Respirometry.* Master's Thesis, Clemson University, Clemson, S.C., 1989). Roš classified respirometers into two groups: (1) closed respirometers and (2) open respirometers (Roš, M. *Respirometry of Activated Sludge.* Lancaster, Pa.: Technomic Publishing Company, Inc., 1993).

Manometric respirometers measure changes in pressure in a constant column system, typically as oxygen is consumed. The Warburg respirometer is an example of this type (Umbreit, W. W., Burris, R. H., & Stauffer, J. F. *Manometric Techniques and Related Methods for the Study of Tissue Metabolism.* Minneapolis, Minn.: Burgess Publishing Co., 1964). Oxygen consumption over time is determined by noting the decrease in pressure of a constant-volume system held at a constant temperature. Carbon dioxide that is evolved during aerobic respiration is absorbed by a solution of potassium hydroxide.

The Sapromat respirometer uses the volumetric (or electrolytic) method (Voith-Morden, Inc. Sapromat®B [Brochure]. Appleton, Wis.: Author, 1993). With this type of respirometer, the reactor containing the sample is connected to an electrolytic cell that generates and releases pure oxygen as the internal pressure of the system decreases. Again, carbon dioxide is absorbed into an alkaline solution.

Open respirometers are open vessels equipped with an oxygen probe, oxygen meter, recorder and computer for sampling and computing results. Discontinuous types are operated in a batch mode while continuous types are operated as continuously stirred tank reactors (CSTRs).

An alternative to conventional batch studies for determination of kinetic parameters was developed by Grady et al. (1989) for uninhibited aerobic cultures of acclimated and enriched biomass. Those investigators showed it is possible to determine the kinetics of biodegradation of single organic compounds using only measurements of oxygen consumption in batch reactors.

Some investigators have used chloride-specific electrodes to study dechlorination. Nelson et al. used a chloride-specific electrode to investigate the stoichiometry of TCE dechlorination by cultures of an aerobic bacterium resuspended in a potassium phosphate buffer (Nelson, M. J., Montgomery, S. O., Mahaffey, W. R., & Pritchard, P. H. *Biodegradation of trichloroethylene and involvement of an aromatic biodegradative pathway, Applied and Environmental Microbiology*, 53, 949–954, 1987). Oldenhuis et al. measured the chloride produced by dechlorination of TCE by aerobic methanotrophic bacteria (Oldenhuis, R., Oedzes, J. Y., Van Der Waarde, J. J., & Janssen, D. B. *Kinetics of chlorinated hydrocarbon degradation by Methylosinus trichosporium OB3b and toxicity of trichloro-ethylene, Applied and Environmental Microbiology*, 57, 7–1, 1991). Chloride production varied from about 0.2 mM (7 mg/l) to about 6 mM (200 mg/l). Hollinger et al. monitored chloride production by reductive dechlorination of PCE by a pure culture of a novel anaerobic bacterium (Holliger, C., Schraa, G., Stams, A. J. M., & Zehnder, A. J. B. *Enrichment and properties of an anaerobic mixed culture reductively dechlorinating 1,2,3-trichlorobenzene to 1,3-dichlorobenzene, Applied and Environmental Microbiology*, May, 1636–1644, 1992). A low-chloride medium was used, and measured chloride production varied from 3.4 to 4.6M (120 to 160 mg/l).

A number of manufacturers including Arthur Technology, Inc.; Columbus Instruments International Corp.; Challenge Environmental Systems; Voith, Inc. and N-CON Systems Company, Inc. sell respirometers that can be used to monitor aerobic and methanogenic processes. As these units can monitor and/or control only gas concentrations of oxygen ($O_2$), carbon dioxide ($CO_2$) and methane ($CH_4$), they cannot be used in anaerobic respirometry studies of bioremediation processes that incorporate denitrification or sulfate-reduction steps. Nor can these units be used to characterize reductive dechlorination processes. Additional information on the prior art is disclosed in a Phase I Final Report prepared for the National Aeronautics and Space Administration (NASA) Small Business Innovation Research (SBIR) program by Yellowstone Environmental Science, Inc. entitled *Anaerobic Respirometer for Bioremediation Process Design*. This report is incorporated herein by reference as if fully set forth.

SUMMARY OF THE INVENTION

The present invention provides an apparatus and method for anaerobic and aerobic respirometry. The apparatus and method provide for automatically collecting and analyzing the data required to develop intrinsic kinetic and stoichiometric model parameters for biological processes that involve anaerobic respiration, aerobic respiration and dehalogenation. The apparatus and method involve automatically monitoring dissolved electron acceptor concentrations and/or pressures to establish electron acceptor uptake rates and stoichiometry. It may also involve automatically monitoring halogen or halogenated hydrocarbon concentrations to monitor dehalogenation reactions. In a preferred embodiment, the apparatus is operated and the method is performed by means of software residing in a computer.

The justification for using electron acceptor uptake data to obtain intrinsic kinetic parameters lies in the concept of an energy balance. Under this concept, all of the electrons available in a substrate (electron donor) undergoing biodegradation must either be transferred to a terminal electron acceptor (e.g., oxygen, iron, nitrate, sulfate, acetate, etc.) or they must be incorporated into new biomass or soluble products. Thus, electron donor consumption is coupled to reduction of an electron acceptor, biomass growth and possibly product generation. In a anaerobic environment, if the concentrations of substrate, biomass and products are all expressed in electron mole units, then electron acceptor uptake ($EA_u$) at any time in a batch reactor is characterized by the following equation:

$$EA_u = (S_o - S_t) - (X_t - X_o) - (P_t - P_o) \quad (3)$$

where:

$Ea_u$ is the electron acceptor uptake, $S_o$ is the substrate concentration at the start of the experiment, $X_o$ is the biomass concentration at the start of the experiment, $P_o$ is the product concentration at the start of the experiment, $S_t$ is the substrate concentration at any time t during the experiment, $X_t$ is the biomass concentration at any time t during the experiment, and $P_t$ is the product concentration at any time t during the experiment.

For the above equation to be applicable, certain assumptions about the modeled system must be true. First, substrate removal and associated biomass growth and product generation must be coupled and be the only events contributing to electron acceptor consumption. Second, essentially all of the biomass must be capable of degrading the substrate. Third, the biomass must be acclimated to the substrate. Fourth, the concentrations for the initial and final cell, substrate and product must be determinable in electron mole units.

In the instance of denitrification, if a source of nitrogen that is more easily incorporated into biomass than nitrate (such as ammonia nitrogen) is available in the growth medium and none is incorporated into products, then monitoring nitrate consumption with a nitrate ion-selective electrode during batch culture produces the data upon which estimates of kinetic parameters can be based. In this situation, equation (3) above simplifies to:

$$EA_u = S_o - S_t \quad (4)$$

Furthermore, because the stoichiometry of many such reactions is known, monitoring of consumption of other reactants or production of products (such as $H^+$ by means of monitoring of pH) may also be performed.

System software is executed on a programmed digital computer or processor. In the best mode the invention is executed on an IBM-compatible microcomputer (running the Microsoft Windows™ operating system) which includes a central processing unit, main storage, input/output resources and a user interface including a manually-operated keyboard and mouse. An example of such a microcomputer is The Gateway 2000™ P5-60 Computer System. The architecture and operation of The Gateway 2000™ P5-60 Computer System are described in the *User's Guide* by Gateway 2000, 610 Gateway Drive, North Sioux City, S. Dak. 57049. In alternative embodiments, other types of microcomputers (such as the Apple Macintosh) and/or other operating systems (such as IBM's OS/2) are used.

System software is used to automate data collection and display and to support analysis of the collected data for bioprocess model calibration. Collected data may include temperature, pH, oxidation-reduction potential (ORP), pressure, electron donor concentration and electron acceptor concentration. Data analysis may involve fitting electron acceptor depletion data to metabolic and cometabolic bioprocess models.

One object of the present invention is to allow characterization of microbial degradation rates under anaerobic (e.g., denitrifying, sulfate-reducing, iron-reducing and methanogenic) conditions. Another object is to facilitate characterization of both metabolic and cometabolic (e.g., reductive dechlorination) processes. Another object is to allow bioremediation process designers to adopt a "reactor-engineering" approach to process design. Another object is to reduce the labor and time required to collect the data needed to estimate intrinsic kinetic and stoichiometric parameters using conventional procedures. Yet another object is to facilitate the design of industrial wastewater treatment systems. Further objects and advantages of the invention will become apparent from consideration of the drawings and the ensuing description.

BRIEF DESCRIPTION OF THE DRAWINGS

The features of the invention will be better understood by reference to the accompanying drawings which illustrate presently preferred embodiments of the invention.

In the drawings.

Figure 1:
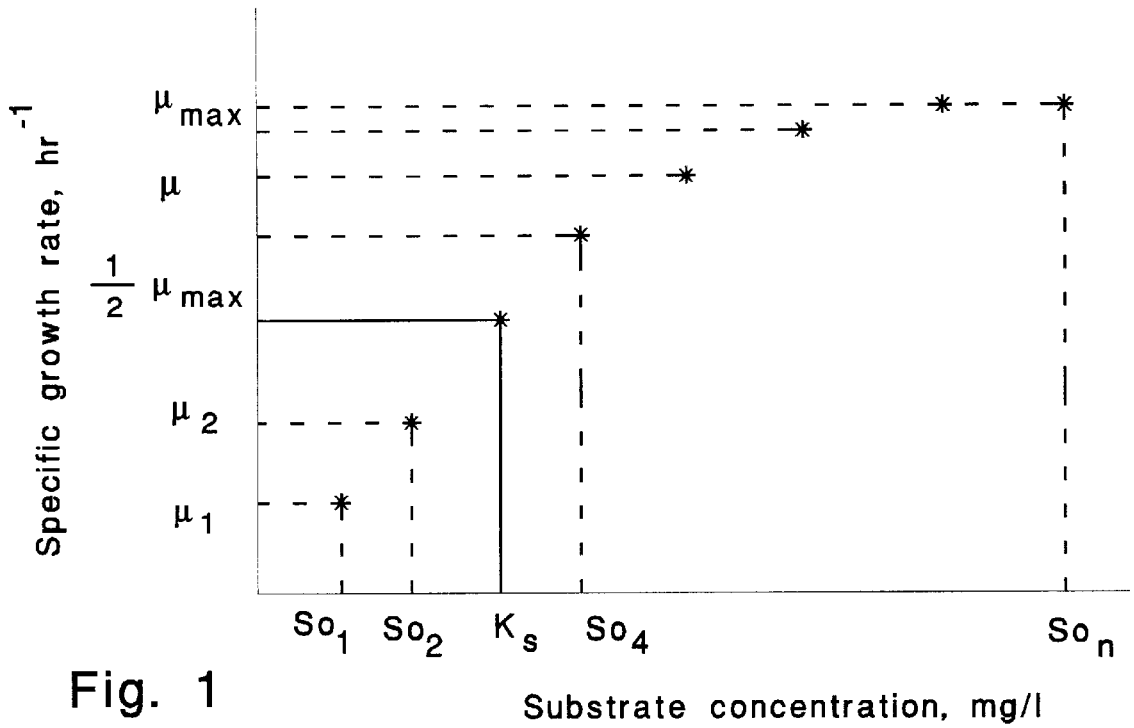
FIG. 1 is a plot of data that fits the Monod equation.
Figure 2:
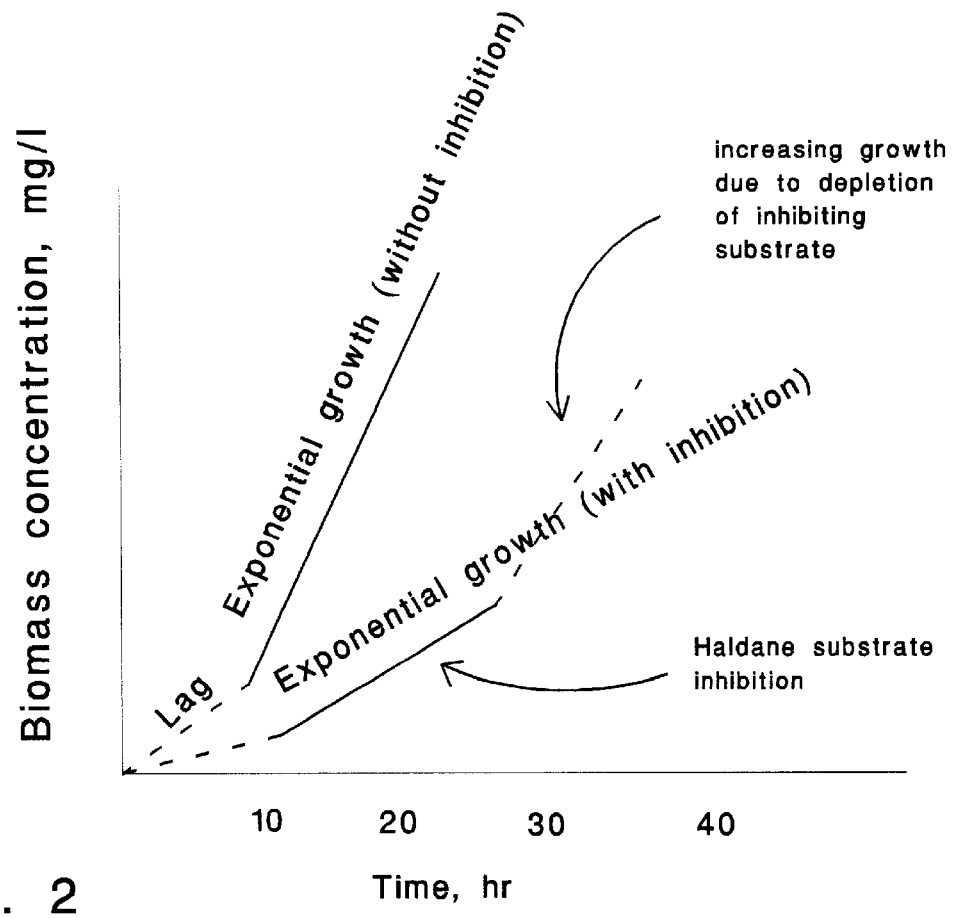
FIG. 2 is a preliminary plot of biomass concentration data versus time.
Figure 3:
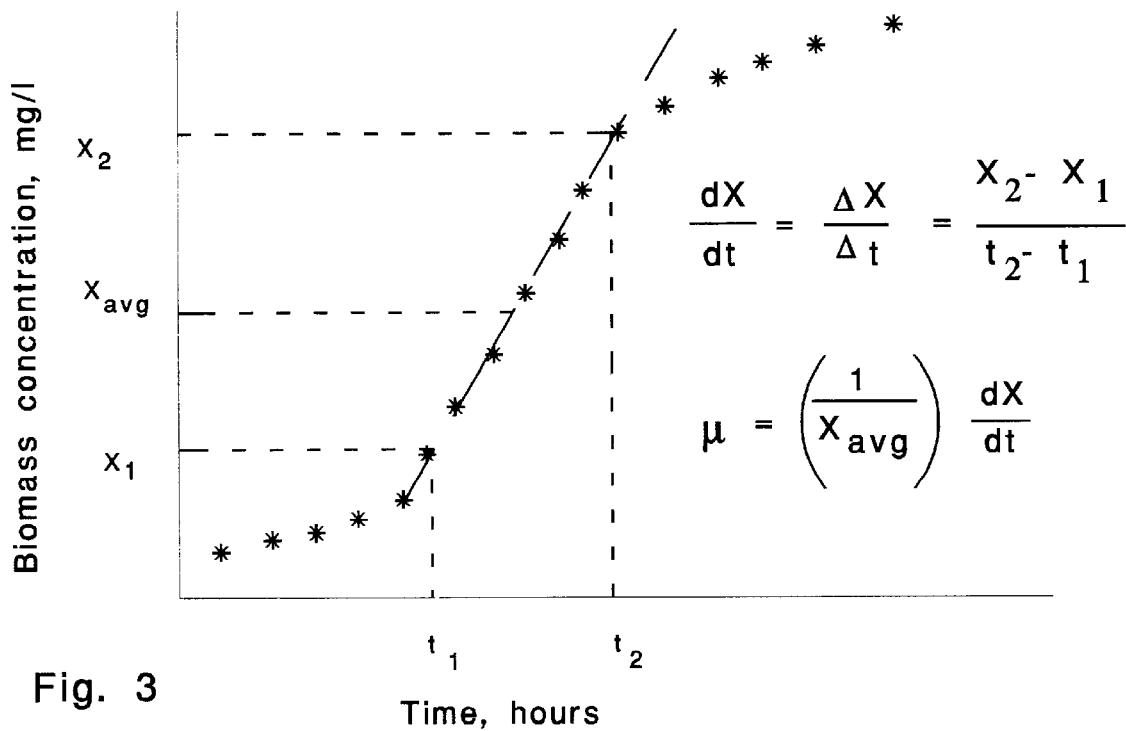
FIG. 3 is a linear plot of biomass concentration versus time data.
Figure 4:
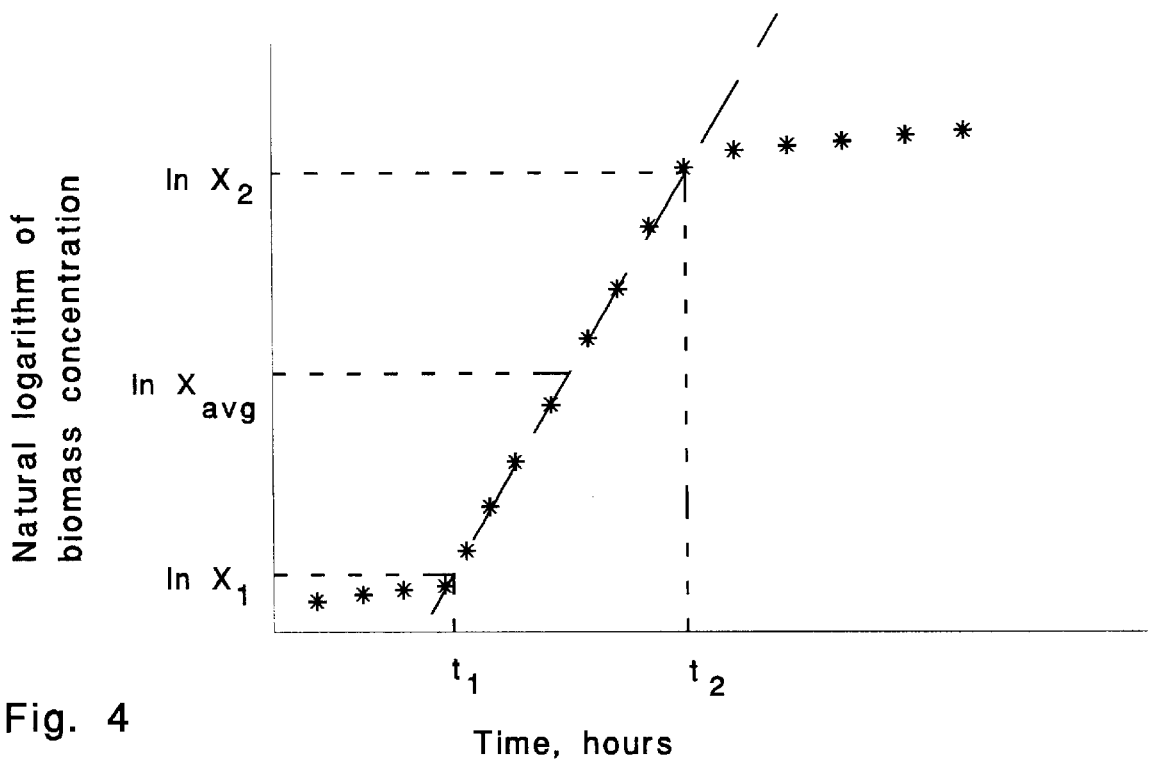
FIG. 4 is a plot of the natural logarithm of biomass concentration versus time.
Figure 5:
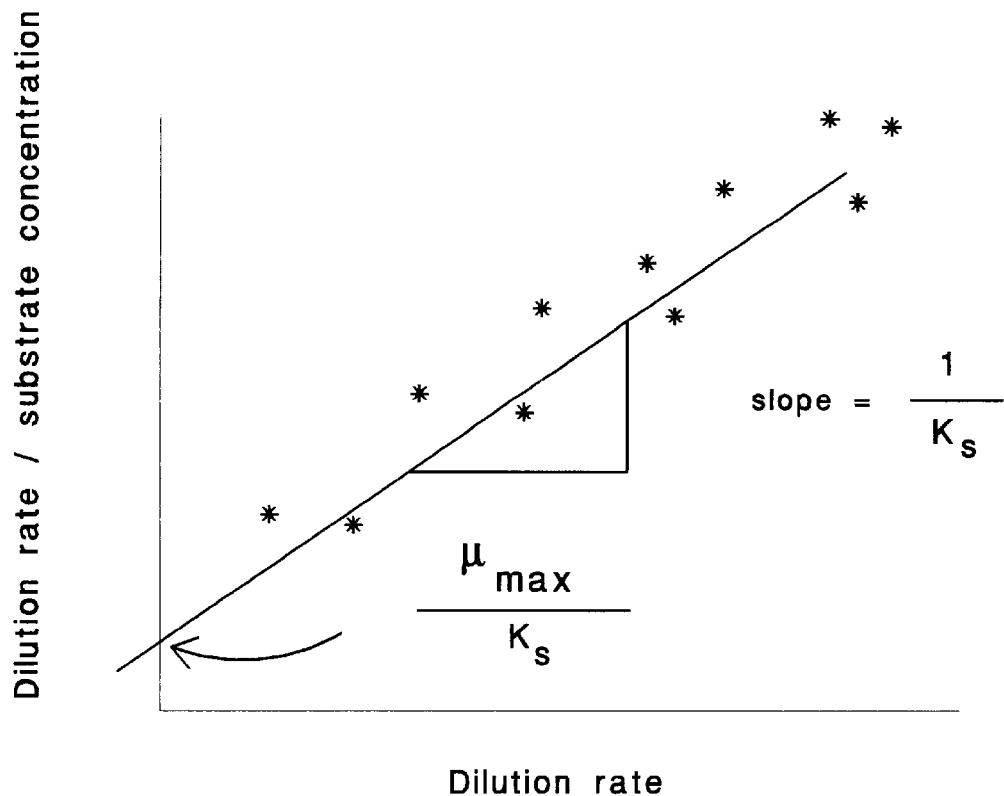
FIG. 5 is a linearized Hosftee plot of the Monod equation.
Figure 6:
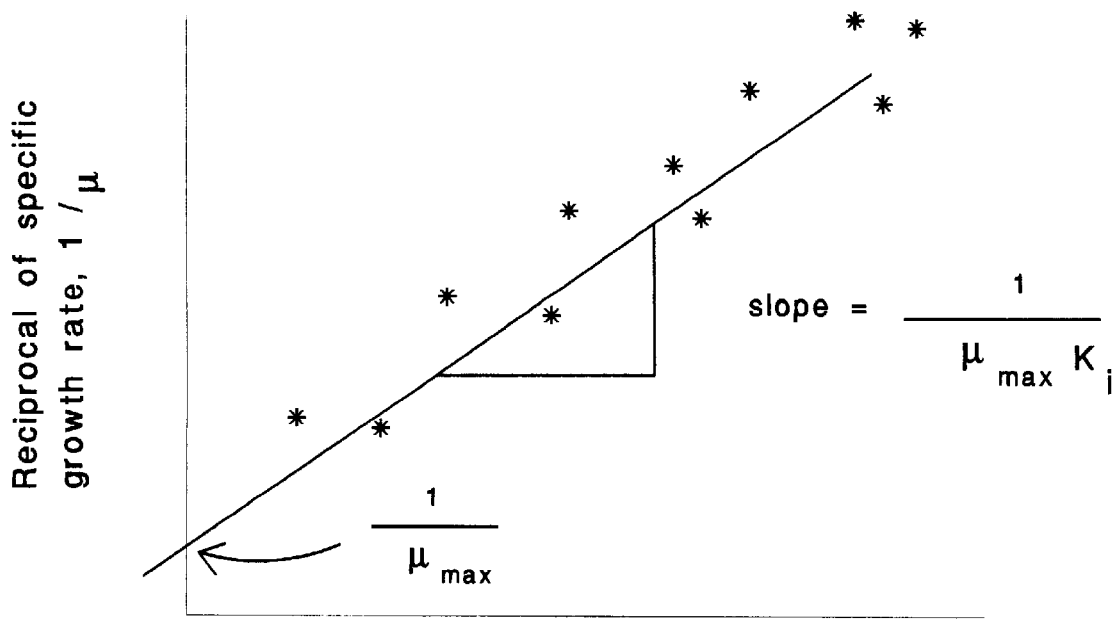
FIG. 6 is a linearized plot used for determination of the half saturation constant.

The following reference numbers are used to indicate the various components of the invention on the drawings:
1 apparatus for anaerobic and aerobic respirometry
3 growth environment subassembly
5 concentration-sensing subassembly
7 pressure-sensing subassembly
9 computer
11 monitor
13 keyboard
14 instrument control subassembly
15 interface hardware
17 software program
25 printer
26 mouse
27 growth reactor
29 growth medium
31 water bath
40 stirrer/heater
42 bottle
44 water
46 magnetic stir bar
50 threaded closure cap
52 gasket
54 stainless steel disk
56 stainless steel tube
58 stainless steel tube
60 stainless steel tube
62 headspace
100 define data set (S, X, E) step
102 plot S vs E and X vs E step
104 linear portions check step
106 set weighting function step
107 differential solution method step
108 determine linear regressions for plots of S vs E and X vs E step
110 determine yield coefficients, electron acceptor demand equivalent of biomass step
111 determine minimum error (difference between predicted and actual values) step
112 determine equations to express S and X as functions of yield coefficients step
114 integral solution method step
116 determine minimum error (difference between predicted and actual values) step
118 end loop and display parameter errors/compare results step
120 program terminate step
122 set weighting function step
124 differential solution method step
126 integral solution method step
128 store values corresponding to minimum error step
200 define input values step
202 determine stoichiometric and kinetic parameters for primary metabolism step
204 calculate specific growth rate step
206 generate and display time plots step
208 define time zones step
210 set manual time zones step
212 fit data to cometabolic model step
214 write step
216 regression step
218 program terminate step
300 high reference standard
302 low reference standard
304 first inoculated medium sample
306 second inoculated medium sample
308 third inoculated medium sample
309 one-liter glass vessels
310 sterile control sample
312 constant-temperature water bath
314 water tank
318 probe manifold
320 nitrate probe
322 chloride probe
324 computer
326 pH probe
328 ORP probe
330 meter
332 first adjusting fluid
334 second adjusting fluid
336 submersible heater
338 magnetic stir plates
340 first solenoid valve
342 second solenoid valve
344 compressed nitrogen tank
346 peristolic pump
348 third solenoid valve
350 Teflon™ tubing
352 Teflon™ tubing
354 regulator
356 pressure sensors

DESCRIPTION OF THE PREFERRED EMBODIMENTS

Figure 7:
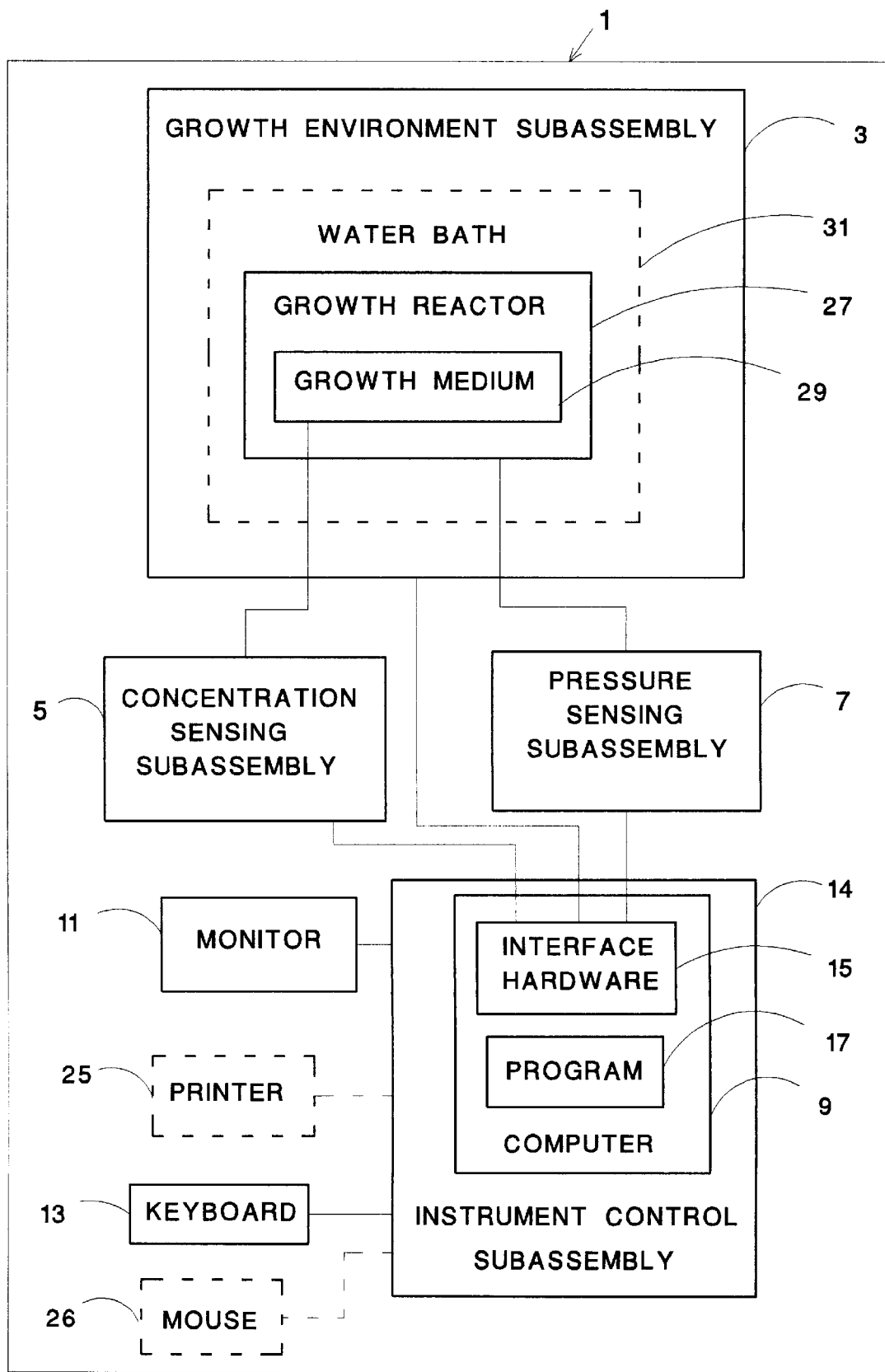
FIG. 7 is a highly schematic diagram of a preferred embodiment of an apparatus for anaerobic and aerobic respirometry.

Reference is now made to FIG. 7 which is a highly schematic block diagram of a representative embodiment of apparatus for anaerobic and aerobic respirometry. Apparatus 1 comprises growth environment subassembly 3, concentration-sensing subassembly 5, pressure-sensing subassembly 7, and instrument control subassembly 14. Instrument control subassembly 14 comprises computer 9, output device or monitor 11, input device or keyboard 13, and interface hardware 15 and software program or programs 17 which preferably reside in computer 9. Growth environment subassembly 3 preferably comprises water bath 31, growth reactor 27 and growth medium 29. Apparatus 1 may also comprise printer 25 and mouse 26. In an alternative embodiment, apparatus 1 may comprise a network (not shown), and all or part of program or programs 17 comprising sets of instructions may reside and/or be executed in a second computer (not shown).

The purpose of growth-environment subassembly 3 is to provide an appropriate environment for microbial growth. The two critical elements of this subassembly are growth reactor 27 and growth medium 29. Growth-environment subassembly 3 preferably includes water bath 31.

The materials of construction and design of reactor 27 are such that it does not corrode, absorb constituents of medium 29, or participate in microbially-mediated reactions. Water bath 31 is capable of maintaining growth medium 29 in growth reactor 27 at a constant temperature.

In one embodiment, growth reactor 27 is a batch-reactor design that has been used to monitor process dynamics during cometabolism of carbon tetrachloride by a denitrifying consortium (Skeen, R. S., Truex, M. J., Petersen, J. N., & Hill, J. S. *A batch reactor for monitoring process dynamics during biodegradation of volatile organics, Environmental Progress*, 13, 174–176, 1994). While the reactor volume (1.0 liter) was larger than would be required with automatic (instead of manual) reactor monitoring, the basic design has been proven in a similar application. One shortcoming of this design is its high cost due to the material utilized (stainless steel) and the requirement for low-volume, custom manufacture.

In a preferred embodiment, reactor 27 is comprised of 250-, 500- or 1,000-ml commercial glass bottles fitted with Teflon™-lined closures. In this embodiment, each closure has two or three perforations for sample removal and/or medium additions. As indicated schematically in FIG. 8 with this embodiment, water bath 31 is placed on magnetic stirrer/heater 40 and Pyrex™ glass bottle 42 is placed in water bath 31. Water bath 31 is filled with water 44 which may be heated by stirrer/heater 40 or by a circulation heater (not shown). Magnetic stir bar 46 is placed in bottle 42 and rotated by stirrer 40, thereby mixing growth medium 29. Threaded closure cap 50 is screwed firmly on bottle 42, thereby compressing gasket 52 between the mouth of bottle 42 and stainless steel disk 54. Disk 54 is perforated by three stainless steel tubes 56, 58 and 60. Tube 56 extends into medium 29 so that samples of medium 29 can be removed from bottle 42. Tubes 58 and 60 terminate in headspace 62 of bottle 42 and can be used to introduce a titrant (e.g., acid or base) into bottle 42 or to sample or determine the pressure of headspace 62.

Referring again to FIG. 7, in a preferred mode of operation of apparatus 1, kinetic and stoichiometric studies are conducted on microorganisms in batch suspended culture in medium 29 to ensure that mass transport limitations do not obscure intrinsic biodegradation rates. Typically, growth medium 29 is designed for each type of microorganism under study. Growth medium 29 must contain all of the constituents required for growth of that microorganism. The concentration of one constituent, typically the electron donor, is selected to be the limiting factor in the rate of microbial growth. This constituent is called the "limiting substrate."

Accurate sensing of the concentrations of electron acceptors and products (e.g., $NO_3^-$, $Cl^-$, and $SO_4^{-2}$) in medium 29 is most readily achieved by designing growth media which contain relatively small concentrations of these constituents. Preferably, designs (recipes) of growth media 29 reduce the concentrations of these constituents without either preventing or retarding microbial growth, or causing the constituents to become limiting nutrients. Major media constituent concentrations for denitrification, sulfate reduction and methanogenesis are given in Tables 1, 2 and 3. These tables contain concentrations for typical, allowable and proposed constituent concentrations.

TABLE 1

Comparison of Typical, Proposed and Allowable Denitrification Media Constituent Concentrations

| | Concentration, mg/l | | | |
| | | | Allowable | |
| Ion | Typical | Proposed | Nitrate electrode | Chloride electrode |
| --- | --- | --- | --- | --- |
| Carbon source | 4000[a] | 20 | NL[b] | NL |
| Ammonium | 800[a,c] | 1 | NL | <1[e] |
| Chloride | 50[a] | 10 | NL | 1.8–35,000 |
| Hydroxide | $10^{-7}M$[a] | $10^{-6}M$ | NL | $10^{-12}$–$10^{-2}M$ |
| Phosphate, dihydrogen | 40[a] | 40 | <3,500 | NL |
| Phosphate, monohydrogen | 370[a] | 370 | <3,400 | NL |
| Nitrate | 3,000[a] | 150 | 0.5–60,000 | NL |
| Sulfate | 800+[a] | 800 | <6,900 | NL |

[a]Source: Jeter and Ingraham, 1981
[b]No limit
[c]Optional

TABLE 2

Comparison of Typical, Proposed and Allowable Sulfate-Reduction Media Constituent Concentrations

| | Concentration, mg/l | | | |
| | | | Allowable | |
| Ion | Typical | Proposed | Chloride electrode | Lead electrode |
| --- | --- | --- | --- | --- |
| Carbon source | 5000[a] | 20 | NL[b] | NL |
| Ammonium | 100[a] | 1 | <1[c] | NL |
| Bicarbonate | 1,900[a] | 0 | NL | 20,000 |
| Calcium | 40[a] | 0 | NL | 0 |
| Chloride | 700+[a] | 10 | 1.8–35,000 | $10^5$ |
| Hydroxide | $10^{-7}M$[a] | $10^{-7}M$ | $10^{-12}$–$10^{-2}M$ | $10^{-10}$–$10^{-7}M$ |
| Phosphate | 0[a] | 0 | NL | 0 |
| Phosphate, bihydrogen | 140[a] | 140 | NL | NL |
| Sulfate | 2,000+[a] | 2,000 | NL | >10 |
| Sulfide | $10^{-8}M$[a] | $10^{-8}M$ | $<10^{-5}M$ | NL |

[a]Source: Pfennig et al., 1981
[b]No limit
[c]Ammonia is the interfering constituent

TABLE 3

Comparison of Typical, Proposed and Allowable Methanogenic Media Constituent Concentrations

| | Concentration, mg/l | | |
| | | | Allowable |
| Ion | Typical | Proposed | Chloride electrode |
| --- | --- | --- | --- |
| Carbon source | 1,500[a] | 500 | NL |

TABLE 3-continued

Comparison of Typical, Proposed and Allowable Methanogenic Media Constituent Concentrations

| | Concentration, mg/l | | |
|---|---|---|---|
| Ion | Typical | Proposed | Allowable Chloride electrode |
| Ammonium[b] | <[a] | 1 | 1[b] |
| Chloride | <[a] | 1 | 1.8–35,000 |
| Hydroxide | $10^{-7}$M[a] | $10^{-7}$M | $10^{-12}$–$10^{-2}$M |

[a]Source: Mah and Smith, 1981
[b]Ammonia is the interfering constituent

The purpose of concentration-sensing subassembly 5 is to monitor constituent concentrations in growth medium 29 during a batch experiment. In an embodiment preferred for bioremediation design purposes, the following constituents are monitored:

Nitrate as electron acceptor
Chloride as product
Sulfate as electron acceptor
Acetate as electron acceptor and electron donor The concentration-sensing subassembly may comprise a range of sensing technologies. In a preferred embodiment, one or both sensing technologies are used to monitor transformations during anaerobic respiration: ion-specific electrode (ISE) technology and ion chromatography (IC). In another preferred embodiment, a dissolved oxygen electrode and/or a pressure sensor is used to monitor transformations during aerobic respiration.

Ion-selective electrode technology may be used to measure nitrate concentrations. Commercial nitrate electrodes are of the PVC-membrane type. This type of electrode features a water-insoluble liquid ion exchanger held in place by an inert porous membrane. In nitrate electrodes, a non-porous polyvinyl chloride (PVC) gel contains the ion exchanger. They can be used to measure nitrate concentrations in the range 0.5 to 62,000 mg/l ($7*10^{-6}$ to 1.0M), at temperatures from 0° to 50° C., and over a pH range of 2.5 to 11 (Cole-Parmer Instrument Company. Cole-Parmer [catalog]. Niles, Ill.: Author, 1994).

Orion Research states that direct electrode measurements of nitrate are reproducible to ± two percent, with calibration every hour (Orion Research, Inc. ORION Model 94-17B Chloride and Model 96-17B Combination Chloride Electrodes [Brochure]. Boston, Mass.: Author, 1994). Electrode response times are good (99 percent in one minute or less) for nitrate concentrations above 60 mg/l ($10^{-3}$M), but these response times fall to two to five minutes at a concentration below 60 mg/l. Samples and standard solution temperatures should be within ±1° C. At a concentration of $10^{-3}$M, a 1° C. difference in temperature can cause a two percent error in concentration measurement. High concentrations of interfering ions may cause errors in concentration measurements.

Ion-selective electrode technology can also be used to measure chloride concentrations. Commercial chloride electrodes are of the solid-state type. This type of electrode has a sensing membrane permanently mounted in the electrode tip, across which an ion potential develops. They can be used to measure chloride concentrations in the range of 1.8 to 35,500 mg/l ($5*10^{-5}$ to 1.0M), at temperatures from 0° to 100° C., and over a pH range of 2 to 12 (Cole and Parmer, 1994).

Orion Research (1994) also states direct electrode measurements of chloride are reproducible to ±2 percent of reading, with calibration every hour. Samples and standard solution temperatures should be within ±1° C. At a concentration of $10^{-3}$M, a 1° C. difference in temperature can cause a two percent error in concentration measurement. Strongly-reducing solutions may form a surface layer of silver on the membrane which may be removed by polishing.

Sulfate ion-selective electrodes are not available commercially. Pungor et al. reported an electrode that is specific to sulfate ions can be constructed using barium sulfate as the active material in a silicone rubber matrix (Pungor, E. & Havas, J. *Electrochemical behavior of ionite and complexonites membrane electrodes*, Acta Chimica Academiae Scientiarum Hungaricae Tomus, 50, 77–104, 1966). Phosphate causes interference, but not 0.1M potassium chloride. Saunders patented a similar electrode in U.S. Pat. No. 3,709,811, the disclosure of which is incorporated by reference herein as if fully set forth (Saunders, A. M., U.S. Pat. No. 3,709, 811, Jan. 9, 1973).

A commercially available ion-selective system for measurement of sulfate-ion concentrations involves using a lead electrode to determine the endpoint of sulfate titration (Orion Research, 1994). Lead ion-selective electrodes are of the solid state type. They can be used to measure lead concentrations in the range 0.2 to 20,700 mg/l ($10^{-6}$ to $10^{-1}$M), at temperatures from 0° to 80° C., and over a pH range of 4 to 7.

A lead electrode can be used as an endpoint detector for titrations of sulfate ion (as low as 10 mg/l) with lead perchlorate. An ORION 960 Autochemistry System may be used to automate these titrations. High concentrations of interfering ions may cause errors in concentration measurements. Samples are diluted 1:1 with methanol-formaldehyde solution before performing the titration. A minimum original sample size of 0.5 ml is recommended.

Another option for monitoring the rate of at least biological sulfate reduction with an ion-selective electrode is to use a carbon dioxide/carbonate electrode. This is possible because the rate bicarbonate plus carbonate alkalinity production is linearly proportional to the rate of sulfate reduction (Abd-el-Malek, Y. & Rizk, S. G. *Bacterial sulphate reduction and the development of alkalinity. I. Experiments with synthetic media*, Journal of Applied Bacteriology, 26, 7–13, 1963; Hunter, R. M. *Biocatalyzed partial demineralization of acidic metal-sulfate solutions*, (Doctoral dissertation, Montana State University), University Microfilms International, 1989). Commercial carbon dioxide/carbonate electrodes are of the gas sensing type. This type of electrode has a gas permeable/ion impermeable membrane across which $CO_2$ diffuses causing the pH of the internal filling solution to change. The change in internal pH is sensed by the electrode. They can be used to measure carbon dioxide/carbonate in the range 4.4 to 440 mg/l ($10^{-4}$ to $10^{-2}$M), at temperatures from 0° to 50° C., and over a pH range of 4.8 to 5.2 (Cole-Parmer, 1994). Because of the nature of the electrode, pH adjustment of the sample prior to analysis would be required. Volatile weak acids cause interferences. Algorithms are available for calculating $HCO_{3-}$ and $CO_3^{-2}$ alkalinities, once the concentrations for pH and carbon dioxide and total filtrable residue (total dissolved solids) are known.

Concentrations of carboxylic ions, such as acetate and formate, can be determined using specially-prepared liquid membrane or heterogenous solid-state electrodes (Ma, T. S. & Hassan, S. S. M. *Organic analysis using ion-selective electrodes*. New York: Academic Press, 1982). Coetzee and Freiser used an Orion calcium electrode with a 0.1M sodium chloride reference phase and an organic phase that consisted of a 10 percent (V/V) solution of Aliquat 336S in one decanol (Coetzee, C. J. & Freiser, H. *Anion-responsive electrodes based on ion association extraction systems.* Tucson, Ariz.: The University of Arizona, Department of Chemistry, 1968). The organic phase was converted to the proper form by repeated soaking in an aqueous solution of the sodium salt of the anion of interest. The useful life of the electrode is one month or longer. The concentration of carboxylic anions within a useful concentration range can be determined with an accuracy of ±0.7 percent.

James et al. demonstrated a liquid-membrane ion-selective electrode with no internal reference solution (James, H., Carmack, G., & Freiser, H. *Coated wire ion selective electrodes, Analytical Chemistry,* 44, 856–857, 1972). The electrode is constructed by coating a fine platinum wire (0.01–0.02 inches in diameter) with a 10:1 mixture of eight percent (W/V) polyvinyl chloride: cyclohexanane and a decanol solution of the ion associate complex. A useful concentration range for acetate of 0.59 to 590 mg/l was reported.

Heterogenous solid-state electrodes that are selective for anions of some saturated monocarboxylic acids (e.g., formate and acetate) have been prepared (Materova, E. & Ovchinnikova, *S. Zh. Anal. Khim.*, 32, 331, 1977). The internal electrolyte solution is 0.1M sodium carboxylate and 5 mM sodium chloride. Nernstian response is reported for 0.5 mM to around one molar (M) concentrations.

An air-gap, gas-sensing, ion-selective electrode has been developed for methylamine (Hsiung, K. P. Kuan, S. S., & Guilbault, G. G. *An ion-selective electrode for methylamine, Analytica Chimica Acta,* 84, 15–22, 1976; Selig, W. *Microdetermination of hydroxyl groups in polymers using phosgene, Mikrochimica Acta,* 612–622, 1972). Prior to direct measurement, the sample pH must be adjusted to 12. An indirect (titration) method has been developed to measure methanol concentrations using a chloride electrode.

In one embodiment, ion-selective electrode technology is used to measure nitrate (directly), chloride (directly), sulfate (directly and indirectly) and acetate (directly) over the concentration range of interest. Use of this sensing technology for sensing requires the following:

1. Frequent (hourly) recalibration of each sensor is necessary. Thus, the sensors must be situated in an external, low-volume, temperature-controlled, valved manifold. Circulation (pumping) of growth medium, as well as calibration standards (and possibly titrant), is required.

2. Operation of the electrodes in non-linear or low concentration regions is required.

3. Standards used to calibrate the electrodes preferably contain the same concentration of interfering substances as the growth medium (and preferably would be comprised of the medium itself).

Some of the interfering substances listed in Tables 1–3 (shown previously) participate in acid-base equilibria reactions that must be considered in measuring the free ion concentrations in the media. A summary of the effects of these substances at pH 7 is shown in Table 4.

TABLE 4

Interfering Concentration of Ions
Interfering ion concentration that causes a 10 percent error at indicated $NO_3$—N concentration, mg/l

| Interfering ion | 1 | 10 | 100 |
|---|---|---|---|
| Nitrite ($NO_2^-$) | 2 | 23 | 230 |
| Bisulfide ($HS^-$) | 2 | 23 | 230 |
| Bicarbonate ($HCO_3^-$) | 44 | 440 | 4,400 |
| Carbonate ($CO_3^{-2}$) | 86 | 860 | 8,600 |
| Chloride ($Cl^-$) | 76 | 760 | 7,600 |
| Dihydrogen phosphate ($H_2PO_4^-$) | 346 | 3,464 | 34,640 |
| Monohydrogen phosphate ($HPO_4^{-2}$) | 343 | 3,430 | 34,300 |
| Phosphate ($PO_4^{-3}$) | 339 | 3,390 | 33,700 |
| Acetate ($Oa_c^-$) | 1,042 | 10,420 | 100,420 |
| Sulfate ($SO_4^{-2}$) | 6,857 | 68,570 | 685,700 |

In a preferred embodiment, ion chromatography is used as the concentration-sensing technology, This technology relies on use of ion-exchange resins to separate ions in chromatographic columns and detection of the ions in discharge from the columns. A typical system includes a liquid eluent (to carry the sample), a (pulseless) high-pressure pump, an injection valve (injector), a separator column (typically in a heater), a detector (often an ion-exchange suppression column or cartridge coupled to a conductivity meter), and a recorder/integrator (which may be software) that runs on a personal computer. The two types of ion chromatography applicable to this invention are anion ion chromatography (anion IC, for $NO_3^-$, $Cl^-$, and $SO_4^{-2}$) and, preferably, ion chromatography exclusion (ICE).

Typical elution conditions for suppressor-type anion IC of solutions with a complex matrix include use of an eluent comprised of 0.003M $NaHCO_3$/0.0012M $NaCO_3$, an eluent flow rate of 2–3 milliliters per minute (ml/min), and an approximate analysis time of 15–18 minutes (Smith, F., Jr. & Chang, R. C. *The Practice of Ion Chromatography.* New York: John Wiley & Sons, 1983). A normal sample injection volume is about 100 $\mu$l, but one to two ml of sample are typically used to flush the transfer line and sample loop.

Particulates must be removed from IC samples by filtration (0.5 $\mu$m or smaller) to prevent column degradation. UV radiation has also been used to kill bacteria before IC injection to prevent their consumption of the resins (Smith and Chang, 1983).

High concentrations of one or more ions in a sample (e.g., chloride in seawater) can overwhelm the column and prevent resolution of individual ions. This problem can often be overcome by sample dilution or treatment, use of different lengths or types of separator columns, or use of different eluent strengths or eluents.

The primary technical limitations of this concentration-sensing option include a relatively large sample volume (>1 ml), a sample filtration requirement and a relatively long analysis time (at least 10 minutes). The primary technical advantage is that all ions of primary interest ($NO_3^-$, $Cl^-$, $SO_4^-$, and $CH_3COO^-$) can be monitored with one sensing means (sensor).

Microorganisms capable of aerobic respiration, as well as those capable of anaerobic respiration (denitrification, sulfate reduction and methanogenesis), produce and/or consume gases during growth. Some of the gaseous products can inhibit growth at higher concentrations. For this reason, sensing of the headspace pressure of the growth environment may be practiced to monitor reactant consumption or produce formation rates. In a preferred embodiment, pressure sensing subassembly 7 comprises a Lucas NovaSensor gage pressure sensor. Model NPI-19J-101GH has 316 stainless steel wetted surfaces, a range of 0 to 15 psi and a linearity of 0.1 percent of full scale (FS). The unit is temperature compensated with a 0.75 percent of FS maximum thermal error over a 0° to 70° C. compensated range and has a ⅛-27 NPT pressure port.

Instrument control subassembly 14 is responsible for: (1) automatically performing required measurement sequences, and/or (2) maintaining constant growth conditions and (3) performing data-manipulation functions. This subassembly comprises computer 9, interface hardware 15 and software program 17. Measurement-sequence control involves actuating pumps and valves, taking probe readings and storing data. Constant-growth control involves comparing sensor readings to desired (or "set-point") values and performing feedback control actions if the measured values are outside of desired limits. Control of pH and electron-acceptor concentration is accomplished by pumping a pre-set volume of acid, base, or a concentrated solution of electron acceptor to the growth reactor and repeating the measurement.

Software program 17 comprises instructions that control operation of apparatus 1. Program 17 may be involved in measuring and controlling the temperature of water bath 31, in measuring and controlling the pressure in growth reactor 27 and in measuring and controlling the concentration of constituents in growth medium 29. In a preferred embodiment, program 17 sends control signals to and receives measurement signals from concentration-sensing subassembly 5 and pressure-sensing subassembly 7.

Software program 17 stores the data it receives from concentration-sensing subassembly and pressure-sensing subassembly in one or more databases. Data from these databases are manipulated to calibrate mathematical models that characterize the biological processes occurring in growth reactor 27.

Many mathematical models of bioprocesses have been developed. The models used in bioremediation process design preferably characterize the intrinsic capabilities of bacteria to degrade or transform hazardous materials. Because bacteria reproduce by dividing in two, the reaction rate for bacterial growth is often expressed as a first order equation:

$$r_{g/x} = \mu X \tag{5}$$

where:
$r_{g/x}$ is the rate of generation of cell material,
$\mu$ is the specific growth rate constant, and
X is cell (biomass) concentration.
Similarly, bacterial death and decay can be expressed as $$-r_{d/x} = bX \tag{6}$$

where:
$r_{d/x}$ is the rate of death and decay of cell material and
b is the maintenance or decay coefficient.
The units of $\mu$ and b are per hour (hr$^{-1}$).
The true growth yield, $Y_g$, is the ratio of the rate of generation of cell material (in the absence of maintenance energy requirements) to the rate of substrate removal:

$$Y_g = r_{g/x}/(-r_s) \tag{7}$$

Combining the above two equations yields:

$$-r_s = (\mu/Y_g)X \tag{8}$$

Thus, the rate of substrate consumption is also first order with respect to the concentration of cells.

The value of the specific growth rate constant, $\mu$, depends on the concentration of the limiting nutrient available for growth. Unfortunately, a mechanistic equation for the relationship between $\mu$ and S has not yet been discovered. As was stated above, the equation that has gained greatest acceptance is the one proposed by Monod:

$$\mu = \mu_{max} S/(K_S + S) \tag{2}$$

While the Monod equation is used in many bioprocess modeling applications, in those situations wherein the substrate is inhibitory to microorganism growth at higher concentrations, a variety of other growth rate equations are also used (Luong, J. H. T. *Generalization of Monod kinetics for analysis of growth data with substrate inhibition, Biotechnology and Bioengineering*, 29, 242–248, 1987; Hans, K. & Levenspiel, O. *Extended monod kinetics for substrate, product, and cell inhibition, Biotechnology and Bioengineering*, 32, 430–437, 1987; Mulchandani, A. & Luong, J. H. T. *Microbial inhibition kinetics revisited, Enzyme Microbiology and Technology*, 11, 66–73, 1989). One such equation is the following that was proposed by Haldane:

$$\mu = \mu_{max}^* S/((K_S + S)(1 + S/K_i)) \tag{9}$$

In the Haldane equation, $K_i$, the inhibition coefficient, is used to correct for substrate inhibition. As $K_i$ approaches infinity, equation 9 approaches the Monod equation 2.

A similar growth rate equation was proposed by Andrews (Andrews, J. F. *A mathematical model for the continuous culture of microorganisms utilizing inhibitory substrates, Biotechnology and Bioengineering*, 10, 707–723, 1968):

$$\mu = \mu_{max}^* S/(K_S + S + S^2/K_i) \tag{10}$$

Again, equation 10 approaches equation 2 as $K_i$ approaches infinity.

The Monod equation has been found to be adequate for modeling the microbial metabolism of a variety of xenobiotic compounds (Shamat, N. A. & Maier, W. J. *Kinetics of biodegradation of chlorinated organics, Journal WPCF*, 52, 2158–2166, 1980; Grady, C. P. L., Jr. *Biodegradation of toxic organics: status and potential, J. Environmental Engineering*, 116, 805–828, 1990). A leader in the field has made the following recommendation concerning model selection (Grady, 1990):

"Because the estimation of $K_i$ requires significant effort, the best procedure would be to adopt a maximum concentration unlikely to be exceeded in wastewaters and to use the Monod model if the compound shows no inhibitory characteristics at that concentration. Otherwise, an inhibition function should be employed."

When the substrate concentration is much lower than $K_s$, the Monod rate expression reduces to the following second-order equation:

$$-r_S = (\mu_{max}/(Y^* K_S))(X^* S) \tag{11}$$

Paris et al. have confirmed the reliability of use of second-order rate constants for biodegradation of xenobiotics (Paris, D. F., Steen, W. C., Baughman, G. L., & Barnett, J. T., Jr. *Second-order model to predict microbial degradation of organic compounds in natural waters, Applied & Environmental Microbiology*, 41, 603–609, 1981).

The model parameters, maximum specific growth rate, half saturation constant and inhibition constant, together with true growth yield, constitute the set of intrinsic kinetic and stoichiometric parameters which characterizes the biodegradation of a toxic organic compound. They are intrinsic because of their dependence only on the nature of the compound and the kind of biomass, but not the physical system.

If one were to consider only the Monod model for reaction occurring in a batch reactor with completely soluble substrate, then the electron balance equation for substrate is:

$$dS/dt = -(\mu_m/Y_g)(S_t/(K_S+S_t))X_t \quad (12)$$

The electron balance equation for substrate is:

$$dX/dt = \mu_m(S_t/(K_S+S_t))X_t - b(K_S/(K_S+S_t))X_t \quad (13)$$

Product formation can be associated with both substrate utilization and biomass decay; but, typically, substrate utilization is the more important source. Hence, product formation may be assumed to be proportional to substrate utilization with a proportionality constant of $Y_p$. In this case the electron balance equation for product is given by:

$$dP/dt = -Y_p(dS/dt) \quad (14)$$

The three differential equations (12-14) must be solved simultaneously and substituted into equation 1 to calculate electron acceptor uptake versus time. Parameters $\mu_{max}$, $K_S$, $Y_g$, and b may be obtained by a non-linear search routine that results in the best fit of the model to the experimental electron-acceptor uptake curve.

The magnitude of the components of an energy balance may be expressed in a variety of units. The selected units may be any units that are consistently used to express the magnitude of the energy embodied by the component, such that energy is conserved during the biologically-mediated transformation of interest.

In aerobic respirometry, a commonly used unit is grams of chemical oxygen demand (COD). This unit is used because when a molecule of oxygen is involved as the electron acceptor in an biologically-mediated oxidation/reduction reaction, a consistent number of electrons are transferred.

In anaerobic respirometry, a variety of electron acceptors may be involved in biologically-mediated oxidation/reduction reactions, depending on the microorganism involved. Some of those electron acceptors are as follows:

| Microorganism type | Electron acceptor |
|---|---|
| Denitrifiers | Nitrate ($NO_3^-$) |
| | Nitrite ($NO_2^-$) |
| | Nitric oxide (NO) |
| | Nitrous oxide ($N_2O$) |
| Iron reducers | Ferric iron ($Fe^{+3}$) |
| Sulfate reducers | Sulfate ($SO_4^{-2}$) |
| Methanogens | Acetate ($CH_3COO^-$) |
| | Formate ($HCOO^-$) |
| | Methanol ($CH_3OH$) |
| | Methylamine ($CH_3NH_2$) |
| | Dimethylamine (($CH_3)_2NH$) |
| | Trimethylamine (($CH_3)_3N$) |
| | Carbon monoxide (CO) |
| | Carbon dioxide ($CO_2$) |

Because of the variety of electron acceptors involved in anaerobic respiration reactions, it is convenient to use a unit that is common to all such reactions. One such unit is the electron mole. The number of electron moles that are involved in any half reaction of an oxidation/reduction reaction can be determined by writing balanced half reactions similar to the following:

$$N_2 + 6H_2O \rightarrow 2NO_3^- + 12H^+ + 10e^- \quad (15)$$

$$Fe^{+2} \rightarrow Fe^{+3} + e^- \quad (16)$$

$$H_2S + HS^- + 8H_2O \rightarrow 2SO_4^{-2} + 19H^+ + 16e^- \quad (17)$$

The above reactions are written in the oxidation "direction" as is the practice in the art. During anaerobic respiration, such reactions proceed in the direction opposite the one shown above. The number of electron moles involved in each reaction is indicated by the integer preceding the "$e^-$" in each equation.

Using an empirical cell formulation of $C_5H_7O_2N$, the following formula can be used to relate cell weight (e.g., in grams) to the number of moles of electrons involved in cell (biomass) generation:

$$C_5H_7O_2N + 9H_2O \rightarrow 4CO_2 + HCO_3^- + NH_4^+ + 20H^+ + 20e^- \quad (18)$$

Since the molecular weight of the empirical cell formula is 113, (113/20) 5.65 grams of cells (on a volatile solids basis) are formed per mole of electrons transferred (McCarty, P. L. *Energetics and bacterial growth*. In S. D. Faust and J. V. Hunter (Eds.), *Organic Compounds in Aquatic Environments*. New York: Marcel Decker, Inc., 1971).

Typically the identity of the product(s) of a reaction are known or can be inferred from changes in the chemical species present in the reactor. If this is the case, the oxidation-reduction equation for the reaction can be written and its half reactions used to quantify product amounts in electron moles.

The process of determining kinetic parameters associated with biodegradation by means of this invention involves a series of steps. An initial step is to establish the overall stoichiometry of the microbially-mediated reaction involved. In such reactions, three types of half reactions apply:

$$R_b = \text{reaction for the biomass} \quad (19)$$

$$R_d \text{ reaction} = \text{reaction for the electron donor} \quad (20)$$

$$R_a = \text{reaction for the electron acceptor.} \quad (21)$$

The overall stoichiometric equation is the sum of the half reactions:

$$R = R_d - f_e R_a - f_s R_b \quad (22)$$

where:

$f_e$ is the fraction of electron donor used for energy and $f_s$ is the fraction of electron donor used for synthesis of biomass.

In order for equation 22 to balance, then $f_e + f_s = 1.0$. To facilitate combining the half reactions they are conveniently written on an electron equivalent basis, with the electrons on the right side. The minus signs in equation 22 requires that the half reactions $R_a$ and $R_b$ be inverted (so that the right side becomes the left side) before summing the three half reactions.

Appropriate half reactions for oxidation of typical biomass, oxidation of selected electron acceptors, and oxidation of selected electron donors are given in Tables 5, 6 and 7, respectively. As was noted above, if the overall stoichiometry of the reaction is not known, it may be established by characterizing the unknown reactants and/or degradation products of the reaction by means of gas chromatography/mass spectrometry or an equivalent analytical technique. Once the identity and quantity of the reactants and products are known, half reactions similar to those listed in Table 7 can be written by those skilled in the art of balancing oxidation-reduction reactions (Kotz, J. C. & Purcell, K. F. *Chemistry and Chemical Reactivity*. Philadelphia, Pa.: Saunders College Publishing, 1991).

TABLE 5

Oxidation Half Reactions Involving Biomass Synthesis

Ammonia as nitrogen source:

$1/20\ C_5H_7O_2N + 9/20\ H_2O \longrightarrow 1/5\ CO_2 + 1/20\ HCO_3 + 1/20\ NH_4 + H^+ + e^-$ Nitrate as nitrogen source:

$1/28\ C_5H_7O_2N + 11/20\ H_2O \longrightarrow 1/28\ NO_3^- + 5/27\ CO_2 + 29/28\ H^+ + e^-$

TABLE 6

Oxidation Half Reaction Involving Electron Acceptors

Carbon dioxide: $1/8\ CH_4 + 1/4\ H_2O \longrightarrow 1/8\ CO_2 + H^+ + e^-$
Nitrate: $1/10\ N_2 + 3/5\ H_2O \longrightarrow 1/5\ NO_3^- + 6/5\ H^+ + e^-$
Oxygen: $1/2\ H_2O \longrightarrow 1/4\ O_2 + H^+ + e^-$
Sulfate: $1/16\ H_2S + 1/16\ HS^- + 1/2\ H_2O \longrightarrow 1/8\ SO_4^- + 19/16\ H^+ + e^-$

TABLE 7

Oxidation Half Reactions Involving Electron Donors

Acetate (mineralization$^a$): $1/8\ CH_3COO^- + 1/4\ H_2O \longrightarrow 1/4\ CO_2 + 7/8\ H^+ + e^-$
Benzene: $1/30\ C_6H_6 + 6/15\ H_2O \longrightarrow 1/5\ CO_2 + H^+ + e^-$
Cresols (mineralization$^a$): $1/34\ CH_3C_6H_4OH + 13/34\ H_2O \longrightarrow 7/34\ CO_2 + H^+ + e^-$
Ethylbenzene (mineralization): $1/42\ C_6H_5C_2H_5 + 8/21\ H_2O \longrightarrow 4/21\ CO_2 + H^+ + e^-$
Phenol (mineralization): $1/28\ C_6H_5OH + 17/28\ H_2O \longrightarrow 3/14\ HCO_3^- + 17/14\ H^+ + e^-$
Toluene (mineralization): $1/36\ C_6H_5CH_3 + 7/18\ H_2O \longrightarrow 7/36\ CO_2 + H^+ + e^-$
Xylenes (mineralization): $1/42\ C_6H_4(CH_3)_2 + 8/21\ H_2O \longrightarrow 4/21\ CO_2 + H^+ + e^-$ $^a$Conversion to carbon dioxide The preferable experimental design for model calibration experiments is the batch experiment. Before the batch experiment begins, the initial substrate (electron donor) concentration ($S_o$) and the initial biomass concentration ($X_o$) are carefully measured and expressed in mass concentration units (e.g., grams per liter). These mass concentration units can be converted to moles of available electron concentration units by reference to half reactions such as those in Table 7, and molecular weight data such as those shown in Table 8. For example, 0.1 g/l of toluene is equivalent to $(0.1/92.14)*36 = 0.0391$ moles of available electrons per liter (Me/l). (Note: In the above equation, 92.14 was taken from Table 8, and 36 was taken from Table 7).

TABLE 8

Formula Weights

| Compound | Formula | Formula weight |
|---|---|---|
| Acetate | $CH_3COO^-$ | 59.04 |
| Benzene | $C_6H_6$ | 78.11 |
| Cresols | $CH_3C_6H_4OH$ | 108.11 |
| Ethylbenzene | $C_6H_5C_2H_5$ | 106.17 |
| Toluene | $C_6H_5CH_3$ | 92.14 |
| Xylenes | $C_6H_4(CH_3)_2$ | 106.17 |

While a variety of models are available for examining the stoichiometry of biodegradation of a compound, the following general expression may be used to describe metabolism, written in terms of oxygen as the electron acceptor:

$$S + Y_{O/S}O_2 \rightarrow Y_{X/S}X + CO_2 + H_2O \quad (23)$$

where:
  S is the primary substrate and electron donor,
  X is biomass, and
  the coefficients $Y_{O/S}$ and $Y_{X/S}$ are the stoichiometric coefficients for oxygen and biomass in terms of mass per total mass of substrate consumed.

When one considers that biomass itself is only partially oxidized from the original substrate (and in fact may even be more reduced), then further oxidation of biomass is possible:

$$X + \beta O_2 \rightarrow CO_2, H_2O \quad (24)$$

where:

$\beta$ is the oxygen demand equivalent of biomass (conventionally taken as 1.42 g $O_2$ per g biomass).

If the concentration of substrate is expressed as COD (chemical oxygen demand—the amount of oxygen required to oxidize 1 gram of substrate to mineral end products $CO_2$ and water), then it can be shown that $Y_{O/S}$, $\beta$ and $Y_{X/S}$ are related by:

$$Y_{O/S} = 1 - \beta Y_{X/S} \quad (25)$$

For anaerobic processes using alternative electron acceptors (i.e., electron acceptors other than oxygen), one can write a general reaction:

$$S + Y_{E/S}E \rightarrow Y_{X/S}X(+CO_2, H_2O) + Y_{P/S}P_r \quad (26)$$

where $Y_{P/S}$ and $Y_{E/S}$ are the amounts of product ($P_r$) produced and electron acceptor (E) utilized per gram of substrate COD utilized. Because the oxidation state and, therefore, the number of electrons accepted per mole of electron acceptor are known, we can write a similar expression to that shown for oxygen, with the addition of a correction factor for the electrons transferred relative to oxygen, and a molecular weight conversion:

$$Y_{E/S} = (1 - \beta Y_{X/S})\left(\frac{4MW_E}{32n_E}\right) \quad (27)$$

where:

$n_E$ is the number of electrons accepted by E in being transformed to reduce product $P_r$, and $MW_E$ is the molecular weight of the electron acceptor. For instance, $n_E$ is 2 for the transformation of nitrate to nitrite, 5 for the transformation of nitrate to nitrogen gas, and 8 for the transformation of sulfate to sulfide. Similarly, one can define a $\beta_E$ as the electron-acceptor demand equivalent of biomass, where:

$$X + \beta_E E \rightarrow CO_2, H_2O, P_r \quad (28)$$

$$\beta_E = \beta\left(\frac{4MW_E}{32n_E}\right) \quad (29)$$

Note that the biomass yields ($Y_{X/S}$) are not of the same magnitude for these two situations; biomass yields are typically 50 percent of the aerobic yield when nitrate is used as the electron acceptor, and less than 10 percent of the aerobic yield when sulfate is the electron acceptor. The use of the above notation thus provides a general relationship for the stoichiometry of cell growth and cell decay which is based on the industry standard of COD.

Thus, there are two reactions occurring in reactor 27 that the user is concerned about, those represented by equations 26 and 28. If one uses the convention that rates are positive for products and negative for reactants, then one has:

$$r_1 = -r_S = -\frac{r_{gE}}{Y_{E/S}} = +\frac{r_{gX}}{Y_{X/S}} \quad (30)$$

where:

$r_s$ is the rate of substrate removal, $r_{gE}$ is the rate of electron acceptor removal associated with biomass growth, $r_{gX}$ is the rate of biomass production associated with biomass decay for the synthesis reaction, and:

$$r_2 = -r_{dX} = -\frac{r_{dE}}{\beta_E} \quad (31)$$

where:

$r_{dX}$ is the rate of biomass production associated with biomass decay and $r_{dE}$ is the rate of electron acceptor removal associated with biomass decay for the decay (or maintenance) reaction. In a batch system, these reaction rates each contribute to the accumulation of the components according to the following equations:

$$\frac{dS}{dt} = r_S \quad (32)$$

$$\frac{dX}{dt} = r_{gX} + r_{dX} \quad (33)$$

$$\frac{dE}{dt} = r_{gE} + r_{dE} \quad (34)$$

Note that these equations do not require any particular form of kinetics.

The following two kinetic models are often used in bioremediation studies when metabolism of a toxic substrate is occurring:

$$r_1 = \frac{q_m S}{K_S + S + S^2/K_{iS}} \quad (35)$$

where: $q_m = \mu_{max}/Y_{x/s}$, and $K_{iS}$ is the inhibition coefficient for the synthesis reaction, and:

$$r_2 = bX \quad (36)$$

where: b is the biomass decay concentration coefficient for the decay reaction. With these expressions, there are three coupled ordinary differential equations in three dependent variables: E, X, and S, the concentrations of electron acceptor, biomass and substrate, respectively.

Although the above description is directed toward the metabolism of some target compound (e.g., toluene), the material balances, stoichiometry and kinetics also apply to the metabolism of a growth substrate during the cometabolic degradation of a secondary substrate (cometabolite). If desired, the potentially inhibitive effects of cometabolite concentration may be incorporated into the growth model by adding inhibition terms of the form:

$$r_1 = r_{1,id}\left(\frac{K_{ci}}{K_{ci} + C}\right) \quad (37)$$

where:

$r_1$ is the actual growth substrate degradation rate, $r_{1,id}$ is the growth rate as predicted by equation (35), $K_{ci}$ is the inhibition coefficient for the cometabolite, and C is the concentration of the cometabolite.

In the case of multiple possible cometabolites, additional multiplying terms may be added of the same form as shown in equation (37).

An example of cometabolism is certain reductive dechlorination reactions. The reductive dechlorination of trichloroethylene (TCE) involves three dechlorination steps resulting in the production of chloride (Cl$^-$), two chlorinated intermediates (dichloroethene (DCE) and vinyl chloride (VC)), and a non-chlorinated and non-hazardous final product (ethylene). The reduction reactions (written in the reduction direction) involved are as follows:

$$C_2HCl_3 + H^+ + 2e^- \rightarrow C_2H_2Cl_2 + Cl^- \quad (38)$$

$$C_2H_2Cl_2 + H^+ + 2e^- \rightarrow C_2H_3Cl + Cl^- \quad (39)$$

$$C_2H_3Cl + H^+ + 2e^- \rightarrow C_2H_4 + Cl^- \quad (40)$$

Each of these reactions produce Cl$^-$ that, in a preferred embodiment, is measured by apparatus 1. For this disclosure, it is assumed that sequential dechlorination occurs. In other words, all of the TCE is first reduced to DCE, then all of the resulting DCE is reduced to VC. After all of the DCE has been reduced, the resulting VC is reduced to ethylene. Kinetic model parameters for each of the reduction steps may be determined using apparatus 1 in a straight-forward way under this assumption.

Apparatus 1 is used to conduct dechlorination batch experiments to generate chloride versus time data sets. These data sets are analyzed by software program 17 in computer 9 to obtain the degradation kinetic model parameters for reductive dechlorination. A preferred model involves a combination of Michaelis-Menten enzyme kinetics, Haldane substrate inhibition kinetics and Monod primary growth kinetics. In a preferred embodiment, product inhibition of the dechlorination reaction is ignored, as is competitive inhibition, although these complicating factors can also be analyzed if more complex models are used.

Because dechlorination is an enzyme-mediated reaction, and each dechlorination step is carried out by a single enzyme (potentially a different enzyme for each cometabolite), the following substrate inhibition enzyme degradation model may be used:

$$-r_{cj} = \frac{K_{2j}C_j}{K_{Sj} + C_j + \frac{C_j^2}{K_{ij}}} \cdot C_{E0j} \quad (41)$$

where:

$C_j$ is the concentration of cometabolite, $K_{2j}$ is the enzyme-specific degradation rate coefficient, $C_{E0j}$ is the amount of enzyme, and $K_{sj}$ and $K_{ij}$ are the half-saturation and substrate inhibition coefficients, respectively.

The subscript "j" is used to indicate that the above general expression will be used for each of the cometabolites (j=1 for TCE, j=2 for DCE, and j=3 for VC).

Because neither the enzyme concentration or specific rate constant are known a priori, but total biomass may be measured, one may use the following expression: Let $f_j$ equal the fraction of the total biomass dry weight consisting of enzyme $Z_j$. We then have:

$$C_{E0j} = f_j X \quad (42)$$

Furthermore, this fraction, $f_j$, may depend on the primary growth rate of the organisms, or:

$$f_j = f_{j0} \cdot (1 + \alpha_j \mu) \quad (43)$$

where:

$f_{j0}$ is the enzyme mass fraction at stationary (zero growth rate) phase and $\alpha_j$ is the relative increase in enzyme content per growth rate increase.

Substituting into equation (41):

$$-r_{cj} = \frac{C_j}{K_{Sj} + C_j + \frac{C_j^2}{K_{ij}}} \cdot K_{2j} f_{j0} X (1 + \alpha_j \mu) \quad (44)$$

Finally, it is apparent that $K_{2j} f_{j0}$ is a single constant that represents the maximum cometabolite degradation rate of a resting culture, or $v_{mj}$, which may be expressed as micromole of cometabolite "j" dechlorinated per milligram biomass per time. Thus, we have:

$$-r_{cj} = \frac{C_j}{K_{Sj} + C_j + \frac{C_j^2}{K_{ij}}} \cdot V_{mj} X (1 + \alpha_j \mu) \quad (45)$$

By assuming that the dechlorination process occurs sequentially, all three of dechlorination steps have the same chloride stoichiometry, and the production of chloride at any time can be expressed by one of the reduction equations:

$$r_{Cl} = -r_{TCE} \text{ or } = -r_{DCE} \text{ or } = -r_{VC} \quad (46)$$

where $-r_{TCE}$, $-r_{DCE}$, and $-r_{VC}$ are the dechlorination rates of each of the cometabolites. Thus, the user makes a subjective decision to specify the endpoint of one dechlorination reaction and the beginning of the next, and so forth. If no clear delineation occurs between successive dechlorinations (i.e., there are no clear plateaus or slope changes in the chloride production curve), then equation (46) no longer applies, and the following equation applies:

$$r_{Cl} = -r_{TCE} - r_{DCE} - r_{VC} \quad (47)$$

In this case, chloride data alone are insufficient to fit all three degradation rate expressions, and growth medium or headspace sampling is required to determine actual TCE, DCE and VC concentrations in growth medium 29 with time. Chloride production data is then used to estimate the cometabolite concentrations in between sampling points, and the resulting modified data set for each of the cometabolites is used to calibrate the kinetic and models to determine the appropriate kinetic model parameters.

As can be found in many general texts on kinetics and analysis of rate data, there are two widely accepted approaches to the problem of deriving kinetic parameters from a data set. These are the differential and integral methods (Grady, C. P. L. Jr. & Lim, G. C. (1980). *Biological Wastewater Treatment*. New York: Marcel Dekker). The former treats the time derivative as a finite difference, and the finite difference is calculated from adjacent data points at time "j" and "j-1." This difference is then treated as the new dependent variable, and the regression is made to minimize the error between that parameter as calculated from the experimental data and its value as predicted from the model and measured concentrations. For equations 32, 33 and 34, for example, we have:

$$\frac{dS}{dt} = \frac{S_j - S_{j-1}}{t_j - t_{j-1}} = y_j;\ \hat{y}_j = \frac{-q_m S_j X_j}{K_S + S_j + \frac{S_j^2}{K_{si}}} \quad (48)$$

$$\frac{dX}{dt} = \frac{X_j - X_{j-1}}{t_j - t_{j-1}} = z_j;\ \hat{z}_j = Y_{X/S} \frac{q_m S_j X_j}{K_S + S_j + \frac{S_j^2}{K_{si}}} - b X_j \quad (49)$$

$$\frac{dE}{dt} = \frac{E_j - E_{j-1}}{t_j - t_{j-1}} = w_j;\ \hat{w}_j = Y_{E/S} \frac{-q_m S_j X_j}{K_S + S_j + \frac{S_j^2}{K_{si}}} - \beta_E b X \quad (50)$$

where:

$y_j$, $w_j$ and $z_j$ are derived from experimental data and $\hat{y}_j$, $\hat{w}_j$, $\hat{z}_j$ are theoretical values.

The resulting equations above would then be used to determine the kinetic and stoichiometric parameters $q_m$, b, $K_S$, $K_{Si}$, $Y_{X/S}$ and $\beta_E$ by minimizing the errors between $y_j$ and $\hat{y}_j$, $w_j$ and $\hat{w}_j$, and $z_j$ and $\hat{z}_j$.

The integral method is based on obtaining an integrated form of the differential equation, and obtaining model parameters by fitting the integrated form to the experimental data. This approach minimizes the error in the concentrations of the various species, rather than attempting to minimize the error in the calculated rate. Unfortunately, the highly coupled and non-linear form of these equations preclude the determination of an analytical solution to equations (32, 33 and 34). However, the finite difference form shown above may be written as a forward rather than backward difference, as noted below, and then solved for the concentration at the next time step.

$$\hat{S}_{j+1} = S_j + \Delta t \left( \frac{-q_m S_j X_j}{K_S + S_j + \frac{S_j^2}{K_{si}}} \right) \quad (51)$$

$$\hat{E}_{j+1} = E_j + \Delta t \left( Y_{E/S} \frac{-q_m S_j X_j}{K_S + S_j + \frac{S_j^2}{K_{si}}} - \beta_E b X_j \right) \quad (52)$$

-continued $$\hat{X}_{j+1} = X_j + \Delta t \left( Y_{X/S} \frac{q_m S_j X_j}{K_S + S_j + \frac{S_j^2}{K_{si}}} - bX_j \right) \quad (53)$$

Thus, the regression may be set up to minimize the error in the predicted value of the concentration at the next time step. In a preferred embodiment, software program 17 fits the data to a nonlinear model using a nonlinear curve-fittinig algorithm, such as the Levenberg-Marquardt method (Press, W. H., Teukolsy, S. A., Vetterling, W. T. and Flannery, B. P. *Numerial Recipes in C: The Art of Scientific Computing*, Cambridge Univ. Press, 1992, In traditional batch experiments, there are generally an equal number of data points for each of the variables $S_j$, $E_j$ and $X_j$; that is, j=1,n for all three variables. With respirometry, however, n is typically around 10 for the substrate concentration, S, and biomass concentration, X, while there may be 100 to 1,000 times as many data points for the electron acceptor concentration, E. If the errors in y, w and z (for the differential form) or the errors in S, E and X (for the integral form) are minimized separately, much of the impact of the additional electron acceptor data is lost, and statistical significance is also doubtful. Fortunately, the stoichiometric relationships are usually well-behaved. That is, statistically significant estimates of $Y_{X/S}$, $Y_{E/S}$ and $\beta$ with high regression coefficients can usually be obtained with a few data points. Ideally, the concentrations S and X may be written as functions of the stoichiometric coefficients and the electron acceptor concentration, E. The large number of data points for electron acceptor concentration can then be used to determine the more difficult-to-determine kinetic parameters $q_m$, $K_S$, $K_{Si}$ and b. Unfortunately, there is no succinct method for predicting the stoichiometric coefficients $Y_{E/S}$, $Y_{X/S}$ and $\beta_E$ when cell decay is a significant fraction of cell growth. In some experiments, however, there may be portions of the curve where cell decay is negligible. For this condition, the last term containing bX may be dropped from equations (51 through 53). These equations may be combined to yield:

$$X = X_0 + \frac{Y_{X/S}}{Y_{E/S}} (E_0 - E) \quad (54)$$

and:

$$S = S_0 - \frac{1}{Y_{E/S}} (E_0 - E) \quad (55)$$

Figure 9:
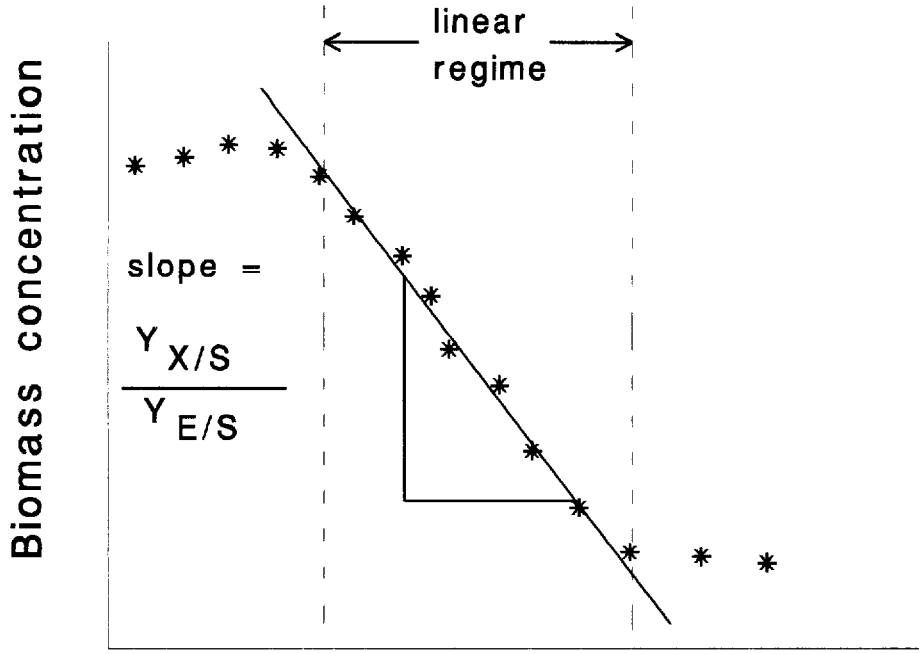
FIG. 9 is a plot of biomass concentration versus electron acceptor concentration data pairs.
Figure 10:
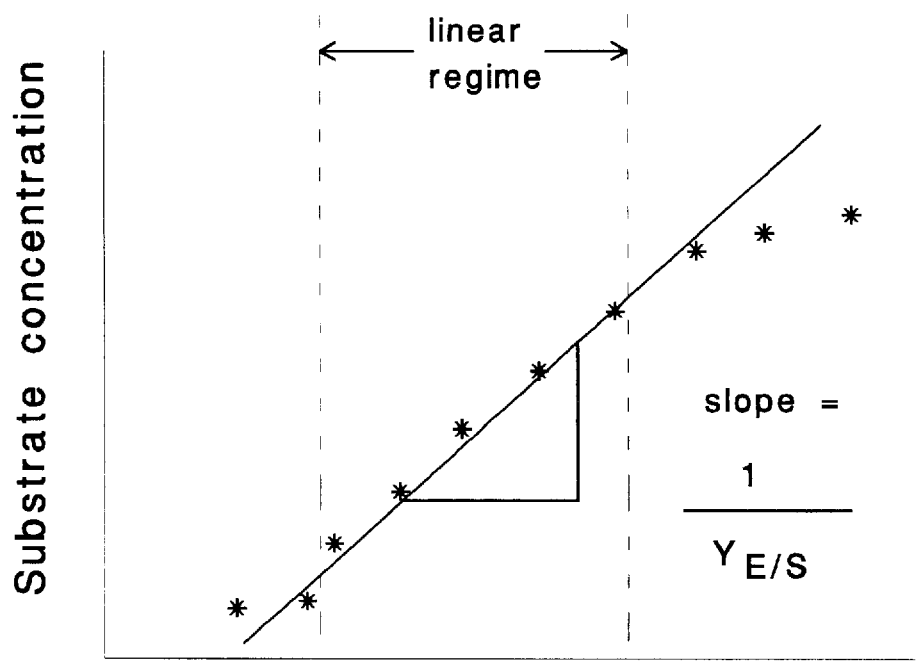
FIG. 10 is a plot of substrate concentration versus electron acceptor concentration data pairs.

Provided that the assumption of negligible cell decay is reasonable, the data taken from apparatus 1 may be used to construct plots of X versus E and S versus E. Sample plots are shown in FIGS. 9 and 10, respectively.

Note that some non-linear behavior is assumed at the beginning (low X, high S) and end (high X, low S) of the experiments for the reasons discussed above. Thus, an envelope of data is chosen by the user of software program 17 which fits the linear stoichiometry model, and the coefficients are determined from the slopes of the lines. Furthermore, equations (54) and (55) above can be used to write S and X in terms of E, and the kinetic model parameters may then be determined by fitting the chosen envelope of E data to equations (2) or (9).

When the stoichiometric coefficients cannot be determined using the above approach, it is necessary to use all of the data and all three equations (48–50) or (51–53) simultaneously. The best approach is to minimize a total error function which weights the data according to the number of data points.

Although a number of other approaches are possible, there are two error functions that are preferably used for error minimization, depending on the character of the data. If the data contain no zero values and the standard deviation of the measurements (i.e., the precision of the measurement technique) is relatively constant, then the mean squared error function (MSE) should be used:

$$MSE = \frac{1}{n} \sum_{j=1}^{n} (f_j - \hat{f}_j)^2 \quad (56)$$

where:

n is the number of measurements, $f_j$ is the measured parameter value, and $\hat{f}_j$ value is the curve-fit parameter value (e.g., electron acceptor concentration).

Alternatively, if the data set does not contain zero values and if the coefficient of variation (the ratio of the standard deviation to the mean) of the measurements is constant, then the relative squared error function (RSE) should be used:

$$RSE = \frac{1}{n} \sum_{j=1}^{n} \left( 1 - \frac{\hat{f}_j}{f_j} \right)^2 \quad (57)$$

When all three equations must be fit simultaneously, the following weighting function is suggested for MSE:

$$MSE = \frac{\sum_{j=1}^{n} (y_j - \hat{y}_j)^2}{\left( \sum_{j=1}^{n} y_j \right)^2} n + \frac{\sum_{j=1}^{n} (z_j - \hat{z}_j)^2}{\left( \sum_{j=1}^{n} z_j \right)^2} n + \frac{\sum_{j=1}^{m} (w_j - \hat{w}_j)^2}{\left( \sum_{j=1}^{m} w_j \right)^2} \quad (58)$$

where:

n is the number of measurements of S, X and m is the number measurements of E.

Weighting of the RSE function is somewhat simpler:

$$SE = n \sum_{j=1}^{n} \left( 1 - \frac{\hat{y}_j}{y_j} \right)^2 + n \sum_{j=1}^{n} \left( 1 - \frac{\hat{z}_j}{z_j} \right)^2 + m \sum_{j=1}^{m} \left( 1 - \frac{\hat{w}_j}{w_j} \right) \quad (59)$$

Thus, the appropriately weighted function is globally minimized with respect to all seven parameter values: $q_m$, $K_S$, $K_{Si}$, b, $Y_{E/S}$, $Y_{X/S}$ and $\beta_E$.

The key to success and to applicability of batch kinetic experiments is the use of the appropriate concentration ranges and the use of acclimated cultures. All respirometry experiments must be started with cultures that have experienced continuous degradation of the target compound for a number of generations. With primary metabolism of more readily degraded substrates, 10 generations is considered adequate. With more recalcitrant compounds and with cometabolism, longer acclimation periods—perhaps as long as 25 generations—are required. Although continuous culture methods are generally considered superior from the viewpoint of developing a fairly stable mixed culture, sequential batches may also be used where 5:1 to 20:1 dilutions are made with fresh media at the end of each growth period. Substrate and/or cometabolite concentrations for the acclimation period should be similar to those used in the respirometry experiments and, of course, in the eventual field application of the culture.

Even with acclimated cultures, it is not uncommon to observe a lag phase when a culture is diluted significantly and placed in fresh medium. Thus, some electron acceptor will be taken up in the absence of substrate uptake during the lag phase. This phenomenon corresponds to a "gearing up" of the organisms in the culture as part of the process of adaptation to the new environmental conditions in the growth reactor 27. Electron acceptor uptake during this period is normally disregarded. Similarly, some electron acceptor uptake is noted following complete disappearance of the substrate, for similar reasons. These data are sometimes used to estimate biomass decay coefficients, but this practice is discouraged. Once the substrate has all been consumed, bacteria have been shown to again change their metabolism to adapt to a low nutrient environment. Many metabolic processes are shut down, and some bacteria undergo sporulation-like behavior, forming smaller cell envelopes and changing the composition of the cell membrane. For these reasons, respiration data at the stationary phase of a growth curve are not representative of what is actually occurring during the active growth phase.

Electron acceptor concentrations at the start of the experiment should always be set just above the stoichiometric maximum requirement for the amount and type of substrate to be tested. This estimate may easily be made by writing balanced half reactions for the substrate acting as electron donor and for the electron acceptor. The electron acceptor required is determined as the ratio of the number of electrons given up by the electron donor, to the number of electrons accepted by the acceptor; such ratio than being multiplied by the molar concentration of donor to be initially used in the experiment. To account for electron acceptor uptake by endogenous respiration and decay, approximately 15 percent excess electron acceptor is recommended. Finally, care should be taken to ensure that other possible electron acceptors are either accounted for in the medium or eliminated altogether.

Although kinetic coefficients may be estimated from the results of a single batch study, more statistically significant results may be obtained from a series of runs. In a preferred embodiment, at least three different initial concentrations of the primary substrate are used, varying from the maximum to be expected in the field to approximately 10 times the maximum contaminant level (MCL) for that particular compound (or ten times the maximum allowable effluent concentration). Runs should be performed at least in duplicate.

Although product inhibition is unusual under aerobic and denitrifying conditions, it is common under sulfate-reducing conditions. Sulfide accumulation above 200 mg/l has been shown to be inhibitive to a number of species of sulfate-reducing bacteria (SRB); care must be taken to avoid this situation. For this eventuality it is recommended that, if feasible, a continuous purge of nitrogen be used to remove excess hydrogen sulfide from reactor 27, and that dual sulfide electrodes be used. One sulfide electrode is located directly within reactor 27, while the other is used in a sulfide trap placed on the exiting nitrogen purge stream. The total mass of sulfide produced may thus be monitored. If volatile substrates are used, the nitrogen purge may be used in a total recycle mode so that there is no loss (or minimum loss) of contaminant due to volatilization.

Statistically, it is not uncommon to have difficulties with high intercorrelation of parameter values when taken from a single data set. For this reason, separate determinations of the key stoichiometric coefficients (parameters) and the kinetic parameters is recommended. This requires that periodic sampling for primary growth substrate and biomass be performed. When the appropriate regressions are performed between biomass and growth substrate and between electron acceptor and growth substrate, the growth yield ($Y_{X/S}$) and electron acceptor requirement ($Y_{E/S}$) may be determined independently. Nonideal or nonlinear behavior at very low or very high substrate concentrations may then be used to determine what data fall into lag and stationary phases, so that these may be excluded from further analyses. Once stoichiometric parameters are determined, they may be treated as known constants in subsequent curve-fitting of the more detailed electron acceptor data to determine the kinetic parameters.

The design of respirometry experiments that use apparatus I to determine cometabolism model parameters (e.g., a model for reductive dechlorination of TCE) should address the following considerations:

1) When monitoring the degradation of TCE during a respirometry experiment, in addition to monitoring chloride concentration, electron acceptor (or its reduced counterpart) should also be monitored. This is done to ensure that the primary growth kinetics do not change while TCE is being degraded. Also, by comparing electron acceptor data from the cometabolite experiments with electron acceptor data from the primary growth studies (in the absence of the cometabolite), it can be shown that reductive dechlorination is truly a "cometabolic" process and does not significantly contribute to cell growth and maintenance. These determinations can be made by confirming the stoichiometry of the denitrification or sulfate reduction reaction using the electron acceptor versus time and periodic sampling for the primary growth substrate.

2) Medium 29 should be periodically sampled to determine the relative concentration of TCE, DCE, VC, ethylene and ethane. The results can be used for these determinations:
   a) Mass balance on the reactor to insure there are no leaks and loss due to volatilization.
   b) Confirm the assumption that the reductive dechlorination steps are occurring sequentially. This sampling should show an accumulation of DCE while TCE is degraded and an accumulation of VC while DCE is degraded.
   c) The determination of the times when each of the reductive dechlorination steps is occurring (determination of $t_1$ and $t_2$).

3) Separate experiments should be run with just vinyl chloride and just DCE. Such experiments enable more accurate determination of the kinetic parameters for the dechlorination of these two intermediates. In addition, these experiments give insight into whether or not product inhibition and/or competitive inhibition is occurring. These experiments may show that TCE, DCE and VC have specific effects on the degradation of one another.

4) The cultures used in all of the experiments should be adequately acclimated to the growth substrate and cometabolite on which they are to be studied. This should include at least 25 generations in the presence of these compounds (double batch growth starter cultures or continuous culture for 25 generations).

In preferred embodiment, software program 17 is developed by means of an object-oriented design process and is implemented in an object-oriented computer language, such as C++. Object-oriented design is the process by which software requirements are turned into a detailed specification of objects (Wirfs-Brock, R., et al. *Designing Object-Oriented Software*. New Jersey: PTR Prentice-Hall, 1990). The object-oriented design process is typically iterative.

A review of user requirements formed the basis of software design. The software accepts the system control and setup information from the user described in Table 9. The software provides a framework for collecting, organizing and reporting the measurements taken by system hardware. The reactor data parameters described in Table 10 are managed for each reactor. Input and output parameters for the modeling subsystem are shown in Table 11. The software produces a real-time graphical report of the following information for each reactor as shown in Table 12.

TABLE 9

Control and Setup Parameters

| Entity name | Data type |
| --- | --- |
| Reactor ID | C[a] |
| Ion chromatograph parameter ID | C |
| Number of reactors | I[b] |
| Number of pumps | I |
| Number of valves | I |
| Pump time on | I |
| Pump rate | N[c] |
| Pump ID | C |
| Valve time on | N |
| Valve ID | C |
| Electron acceptor titrant type | C |
| Electron acceptor titrant concentration | N |
| PH titrant type | C |
| PH titrant concentration | N |
| IC detector in use | C |
| IC column in use | C |
| IC filter in use | C |
| Calibration fluid vessel ID | C |
| Calibration fluid type | C |
| Calibration fluid concentration | N |
| Probe ID | C |
| Electron accepter name | C |
| Reactor liquid initial volume | N |
| Reactor initial headspace volume | N |

[a]Character string, 1–10 characters.
[b]Integer, +/−100.
[c]Numeric, floating decimal, 5 significant digits.

TABLE 10

Measurement and Computed Data

| Entity name | Data type |
| --- | --- |
| Measurement (Raw) Data | |
| Time/date | time/date |
| Temperature device mv | N[a] |
| ISE probe mv | N |
| Pressure sensor mv | N |
| Ion chromatograph parameter value | N |
| Digital port status | I[b] |
| Computed Data | |
| Reactor temperature | N |
| Reactor electron acceptor concentration | N |
| Reactor chloride concentration | N |
| Reactor pH | N |
| Reactor ORP | N |
| Reactor headspace pressure | N |
| IC filter pressure | N |
| Probe gain | N |
| Probe off set | N |
| Reactor liquid volume | N |
| Reactor headspace volume | N |

[a]Numeric, floating decimal, 5 significant digits.
[b]Integer, +/−100.

TABLE 11

Modeling Data

| Entity name | Data type |
| --- | --- |
| Project ID | C[a] |
| Number of data files | I[b] |
| Record file ID | C |
| Model type | C |
| User input a (TCE conc., etc.) | N[c] |
| User input b | N |
| Curve fit parameter a | N |
| Curve fit parameter b | N |
| Curve fit parameter c | N |
| Curve fit parameter d | N |
| Curve fit parameter e | N |
| Curve fit parameter f | N |
| Curve fit parameter g | N |
| Computed graph file ID | C |
| Stoichiometric data input a | N |
| Stoichiometric data input b | N |
| Stoichiometric data input c | N |

[a]Character string, 1–10 characters
[b]Integer, +/−100
[c]Numeric, floating decimal, 5 significant digits

TABLE 12

Real-Time Display Parameters

Reactor temperature
Reactor electron acceptor concentration
Reactor pH
Reactor ORP
Reactor chloride concentration
Reactor headspace pressure
Time until next sample
Pump and valve status (indicated with simulated LEDs)

Following procedures recommended by Wirfs-Brock (1990) and Booch (Booch, G. *Object-Oriented Design with Applications*. U.S.A.: Benjamin/Cummings Publishing Company, Inc., 1991), an initial exploratory phase of object-oriented software design is conducted. Key abstractions that occur in the problem domain are identified. In this way, the requirements specification are decomposed into a variety of objects which communicate with one another to achieve the overall goal of the software. Objects are instances of classes and comprise sets of instructions for the operation of computer 9. One way this is accomplished is by reviewing an outline requirements specification to extract noun phrases, from which to build a list of candidate classes of objects. Candidates for abstract superclasses are identified by grouping classes that share common attributes. A short statement of the purpose of each class is prepared.

The responsibilities of the software are extracted from the specification, noting actions and information. These responsibilities are then assigned to specific classes. Collaborations between classes are identified by examining the responsibilities associated with each class. A collaboration is the embodiment of a contract between a client class and a server class. A client class sends a message to a server class requesting assistance in fulfilling a client responsibility. The output of this design phase is class tables (Wirfs-Brock, 1990).

Exploration of the problem domain begins with identification of the key classes of objects by capturing the user's vocabulary in nouns (classes) and verbs (methods). The key classes of objects included in the invention are: sensor interface objects, instrument control objects, database objects, model calibration objects, data visualization objects and user interface objects.

Exploratory design of the software identifies classes of persistent database objects the application must manage. The attributes of each class of database objects are quantified. Specifically, for each data object (instance of a class), the description, type and length of database field that will hold the object is presented. Key components of domain-interaction systems are database objects. The purpose of these objects is to maintain data in a form that is changeable, but that persists from one use of the software to another.

Each database class is responsible for management of its data elements. As this database management behavior is shared by all database management classes, an abstract superclass (Database) is created to capture this shared behavior in one place. Those shared behaviors (member functions) and database class responsibilities are shown in Table 13.

TABLE 13

Database Class Responsibilities

| Member function | Responsibilities |
|---|---|
| appendRecord | Add a new record to a database object. |
| bottomRecord | Retrieve the bottom (last appended) record of a database object. Position the pointer at the last record, |
| closeDatabase | Close the currently active database object. |
| createDatabase | Create and open a new database object. If successful, it becomes the active database object. |
| createIndex | Create a new index for the active database object. Make it the active index. |
| deleteRecord | Delete a record from the active database object. |
| recordNumber | Return the current record number. |
| retrieveRecord | Retrieve the fields specified for a record. |
| setExact | Set exact or inexact matches on character data types. |
| setFilter | Set a filter for the entire database. Restrict the available records to those that satisfy the filter. |
| skipRecord | Retrieve a record after moving the pointer. |
| topRecord | Retrieve the top (first) record of a database object. Position the pointer at the top record. |
| updateRecord | Update the current record in the active database. |
| useDatabase | Open a database object Make it active. |

Subsystems are groups of classes, or groups of classes and other subsystems, that collaborate among themselves to fulfil a responsibility. Subsystems are developed by generating diagrams called collaborations graphs. These graphs are useful for specifying the detailed functionality of the subsystems which will be implemented. Table 14 shows collaborations for user interface class collaborations. Classes of windows objects, screen objects and other user interface classes are shown in Tables 15, 16 and 17 respectively.

TABLE 14

Collabroations Between Classes

| Client class/responsibility | Server class |
|---|---|
| EditObjects | |
| Display edit object(s) | RecordWindows |
| | OrderedRecordDisplayWindows |
| | OrderedRecordEditWindows |
| Read records | RecordDatabases |
| Write records | RecordDatabases |
| InferenceEngines | |
| Read records | RecordDatabases |
| Write records | RecordDatabases |
| Obtain knowledge | Knowledgebases |
| Obtain answers | RadioButtons |
| OrderedRecordEditWindows | |
| Prevent duplicate order RadioButtons | OrderVerifiers |
| Display buttons TextDisplayWindows | AnswerWindows |
| Obtain text | TextMovers |
| TextEditor | |
| Obtain text | TextMovers |
| Display text | TextEditWindows |
| TextMovers | |
| Read text | TextFiles |
| Write text | TextFiles |

TABLE 15

Classes of Windows Objects

| Class | Responsibilities |
|---|---|
| ControlWindows | Display buttons. |
| MainWindows | Display main menu. |
| OrderedRecordDisplayWindows | Display selected record elements in screen objects in order. |
| OrderedRecordEditWindows | Display selected record elements in order in screen objects. Allow order number editing. |
| RecordEditWindows | Display records in screen objects. Allow record editing. |
| TextDisplayWindows | Display word-wrapped text files. |
| TextEditWindows | Display word-wrapped text files. Allow text editing. |

TABLE 16

Classes of Screen Objects

| Class | Responsibilities |
|---|---|
| Buttons | Display button. Accept a button press. |
| CheckBoxes | Display a set of check boxes. Allow one or more to be selected. |
| ComboBoxes | Display a list of items. Allow one to be edited and/or selected. |
| EditBoxes | Display multiple lines of text. Allow it to be edited. |
| EditLines | Display one line of text. Allow it to be edited. |
| ListBoxes | Display a list of items. Allow one or more to be selected. |
| Menus | Display menu items. Allow one or more to be selected. |
| RadioButtons | Display a set of radio buttons. Allow one to be selected. |

TABLE 17

Other User Interface Classes

| Class | Responsibilities |
|---|---|
| OrderVerifiers | Allowed selection and ordering of records. Verify that record orders are different. |
| TextEditor | Allow text editing. |
| TextMovers | Retrieve text from text file. Write text to text file. |

Figure 11:
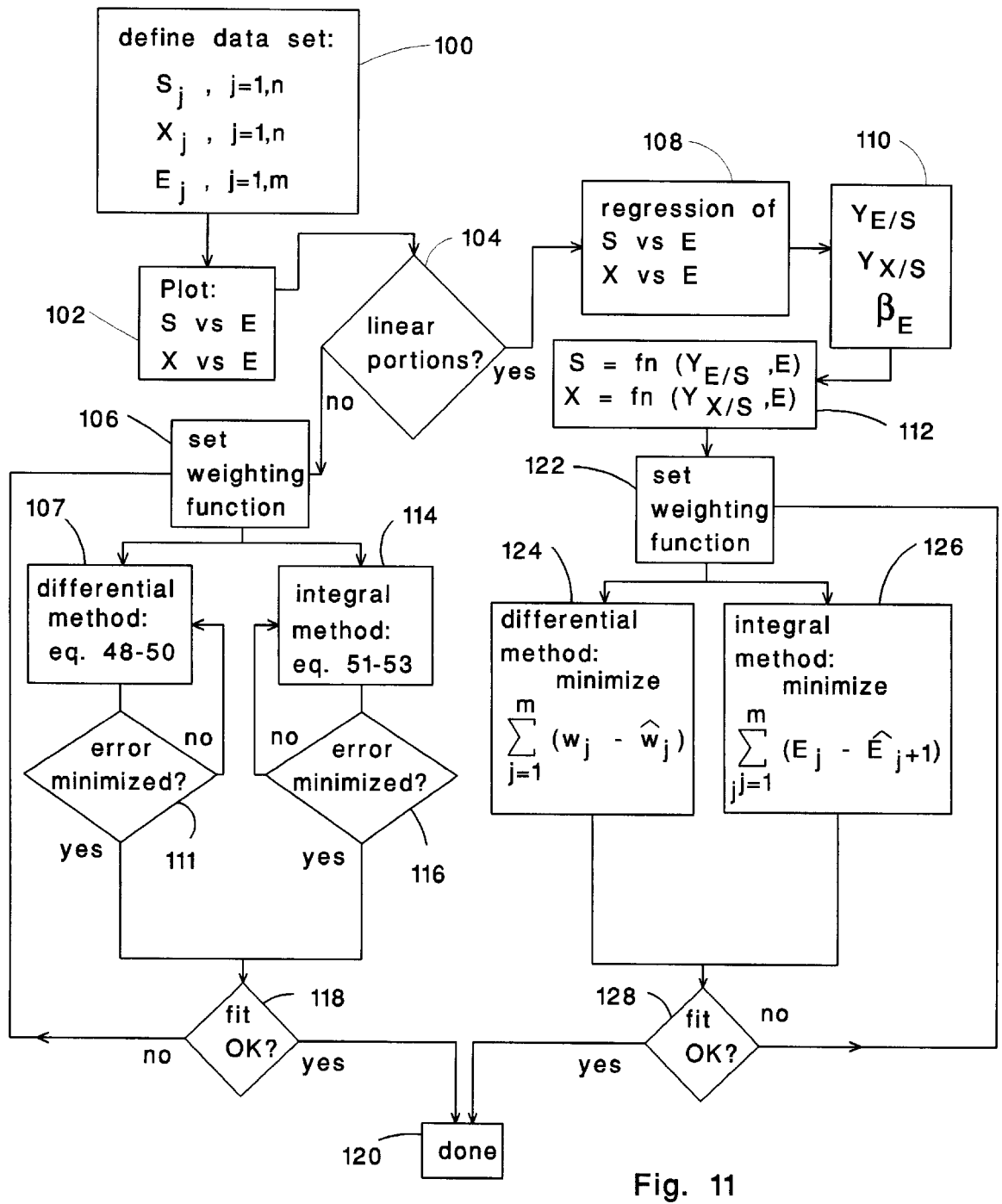
FIG. 11 is a flowchart for the primary metabolism model.

Model calibration classes use information in certain database classes to develop estimates of bioprocess model parameters. A flow chart for one embodiment of a process for calibration of metabolism models is presented in FIG. 11. In this embodiment of the calibration process, kinetic and stoichiometric parameters are determined from data collected during a set of experimental runs. In step 100, values at known times are selected for substrate concentration (S), biomass concentration (X), and electron acceptor concentration (E). Typically, the number of data points for E, which are measured by the respirometer, will be much greater than the number of data points for S and X, which are determined by external analysis.

S and X values are plotted versus E values in Step 102 and checked for linearity in Step 104. If the plots are determined to be linear within preset limits, then the stoichiometric parameters are determined directly (prior to determination of kinetic parameters) in Steps 108 through 112. In Step 108, best-fit linear regressions are determined for the plots. In Step 110, the best-fit slopes are used to determine the yield coefficients $Y_{E/S}$ and $Y_{X/S}$, and the electron acceptor demand equivalent of biomass ($\beta_E$). In step 112, equations are determined which express S and X as functions of yield coefficients and E.

In Step 122, the user selects a weighting function for the error calculations to be carried out in subsequent steps. One preferred weighting function is the mean squared error function (MSE) shown in Equation 56. Another preferred weighting function is the relative squared error function (RSE) shown in Equation 57. In Step 124, the differential solution method is performed by minimizing the error of the slope of $\Delta E/\Delta t$, as shown in Equation 50. The values for the kinetic parameters corresponding to the minimum error are stored in Step 128. In Step 126, the integral solution method is performed by minimizing the error of computed values of E versus measured values of E as shown in Equation 52. The values for the kinetic parameters corresponding to the minimum error are stored in Step 128. In Step 128, the user compares the results of the two computational methods and accepts or rejects the solution. If the solution is accepted, the program terminates in Step 120. If the solution is rejected, the program returns to Step 122, where the user selects a different weighting function, after which the computations are repeated.

Referring to Step 104, if the plots of S versus E and X versus E are determined to be nonlinear within preset limits, then stoichiometric and kinetic parameters are determined simultaneously. In Step 106, a weighting function is selected for the error calculations to be performed in subsequent steps. One preferred weighting function is the MSE function for simultaneous solution of multiple equations shown in Equation 58. Another preferred weighting function is the RSE function for simultaneous solution of multiple equations shown in Equation 59. In Step 107, the differential solution method is performed by inserting trial values for $q_m$, b, $K_S$, $K_{SI}$, $Y_{E/S}$, and $Y_{X/S}$, along with measured values S, X, and E into equations 48–50. The error (difference between predicted values and actual experimental data) is then recorded in Step 111, and then Step 107 is rerun for another set of trial values for $q_m$, b, $K_S$, $K_{SI}$, $Y_{E/S}$, and $Y_{X/S}$. When the minimum error has been determined in Step 111, the loop terminates and the errors for each parameter are displayed in Step 118. In Step 114, the integral solution method is performed by inserting trial values for $q_m$, b, $K_S$, $K_{SI}$, $Y_{E/S}$, and $Y_{X/S}$ along with measured values S, X, and E into equations 51–53. The error is recorded in Step 116, and then Step 114 is rerun with another set of trial values for $q_m$, b, $K_S$, $K_{SI}$, $Y_{E/S}$, and $Y_{X/S}$. When the minimum error has been determined in Step 116, the loop terminates and the errors for each parameter are displayed in Step 118.

In Step 118, the user compares the results of the two computation methods and approves or rejects the solutions. If the data are accepted, the program terminates in Step 120. If the data are rejected, the program returns to Step 106, where the user will select an alternate weighting method, after which the differential and integral solution methods are rerun.

Figure 12:
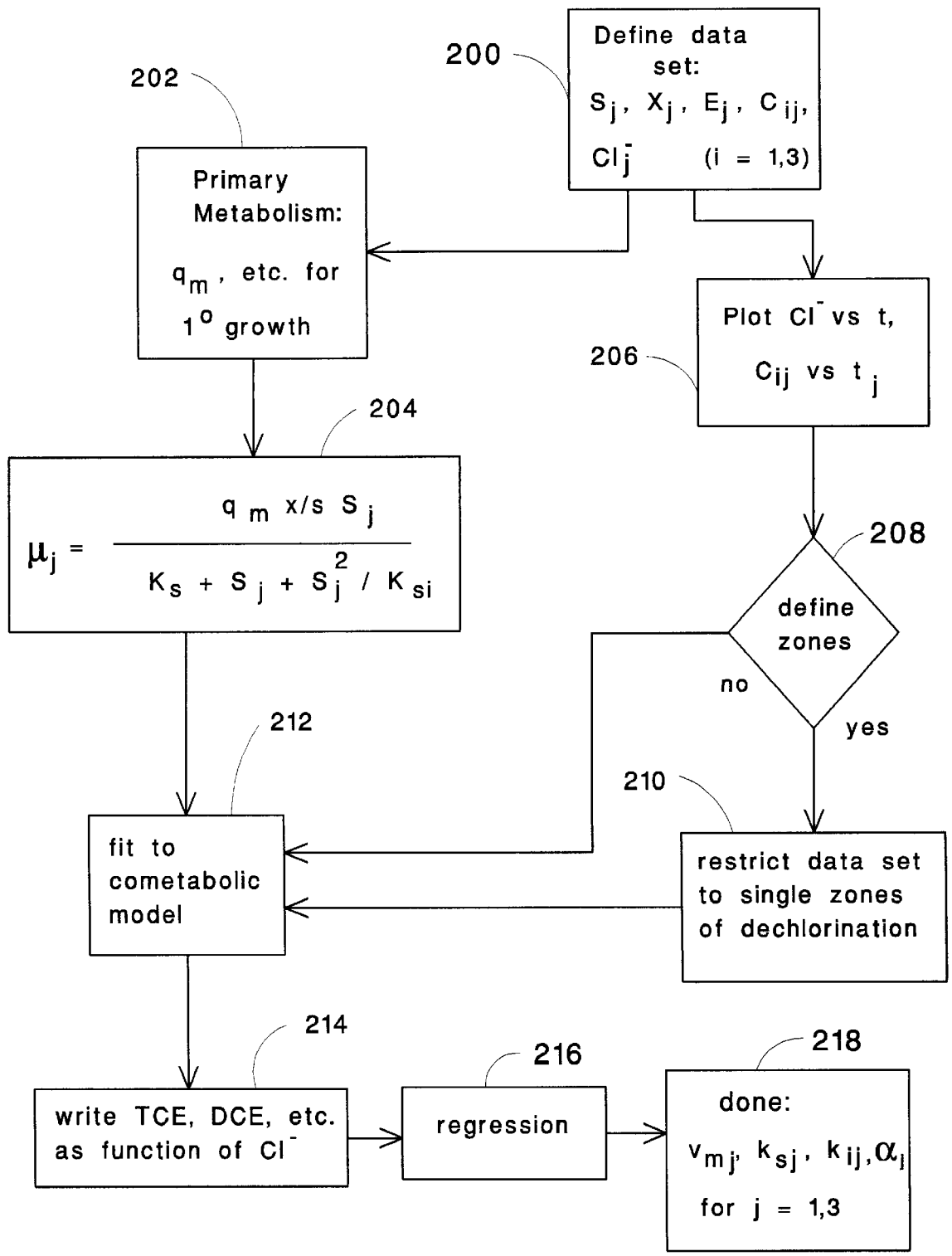
FIG. 12 is a flowchart for the cometabolism model.

A flow chart for one embodiment of a process for calibration of cometabolism models is presented in FIG. 12. This modeling procedure is appropriate for use when it is desired to determine both kinetic and stoichiometric parameters from data collected during a set of experimental runs. In Step 200, input values to be used in the process are selected. These inputs consist of values for primary substrate (S), biomass concentration (x), electron acceptor concentration (E), chloride (Cl$^-$), and cometabolic substrates #1, #2, and #3 ($C_1$, $C_2$, and $C_3$). In Step 202, the stoichiometric and kinetic parameters for primary metabolism (during first order growth) are determined by performing all of the steps shown in FIG. 11. In Step 204, a specific growth rate ($\mu$) is calculated for each set of data points. In Step 206, time plots are generated for Cl$^-$, $C_1$, $C_2$, and $C_3$ and displayed to the user. In Step 208, the user can choose to manually partition the data into sequential time zones (corresponding to the zones of degradation of $C_1$, $C_2$, and $C_3$) or the user can allow the program to determine these zones automatically. If manual partitioning is selected, the user sets the zones in Step 210. If automatic partitioning is selected, the program advances to Step 212, where the data is fit to a cometabolic model. A preferred cometabolic model is shown in Equation 45. In Step 214, the values of $C_1$, $C_2$, and $C_3$ are each expressed as functions of Cl$^-$. In Step 216, regression is performed to find a best-fit solution for the three functions. The program terminates in Step 218, where all of the computed parameters are displayed.

WORKING EXAMPLE

A working model of an embodiment of apparatus 1 was constructed and three experimental runs were conducted using the working model over a one-month period. Equipment which was employed in the system tests included the items which are shown schematically in FIG. 13.

Experimental runs were initiated by preparing high and low concentration reference standards 300 and 302, inoculated media samples 304, 306 and 308; and a sterile control sample 310. All standards and samples were put in similar one-liter glass reactor vessels 309, and the vessels were installed in a constant-temperature water bath 312. System status and probe readings were displayed graphically on the monitor of computer 324 during a run. Typical runs took from two to twenty days to complete, depending on the type and concentration of contaminant being degraded.

Measurements were taken automatically at timed intervals or manually under operator control. A complete measurement cycle involved the following steps:

1. Pump the high-level reference standard 300 through the probe manifold 318 and record millivolt readings from the nitrate and chloride probes 320 and 322.
2. Pump the low-level reference standard 302 through the probe manifold 318 and repeat the measurements as in the previous step.
3. Verify that probe responses are within tolerance for the two reference standards, and compute gains and offsets for each probe automatically with computer 324.
4. Pump a portion of first inoculated sample 304 through the probe manifold 318 and record readings for nitrate, chloride, pH and ORP (oxidation/reduction potential) with probes 320, 322, 326, and 328, respectively. Recover a sealed sample of the fluid for laboratory analysis by ion chromatograph (IC) and/or gas chromatograph (GC) (neither shown).
5. Repeat the measurements for additional samples 306, 308 and 310.
6. Transmit the probe readings through meter 330 to computer 324. In computer 324, convert the millivolt probe readings to ppm (parts per million) concentration readings for nitrate and chloride, to pH units for hydrogen ion concentration, and to calibrated ORP millivolts for oxidation/reduction potential. Add the data to a persistent database within computer 324, and add the data to the graphical screen display in computer 324.

The system was capable of providing constant reaction conditions in sample 310 by adding adjusting fluids 332 and 334 to sample 310 automatically in response to the probe readings. When used in this mode, the volume of additives is automatically recorded. The components of the system which were in contact with fluids or system gas ("wetted components") were selected for the following characteristics: impermeability to oxygen, low absorbance and reactivity to aromatic and chlorinated hydrocarbons, and minimum volume for plumbing.

Figure 8:
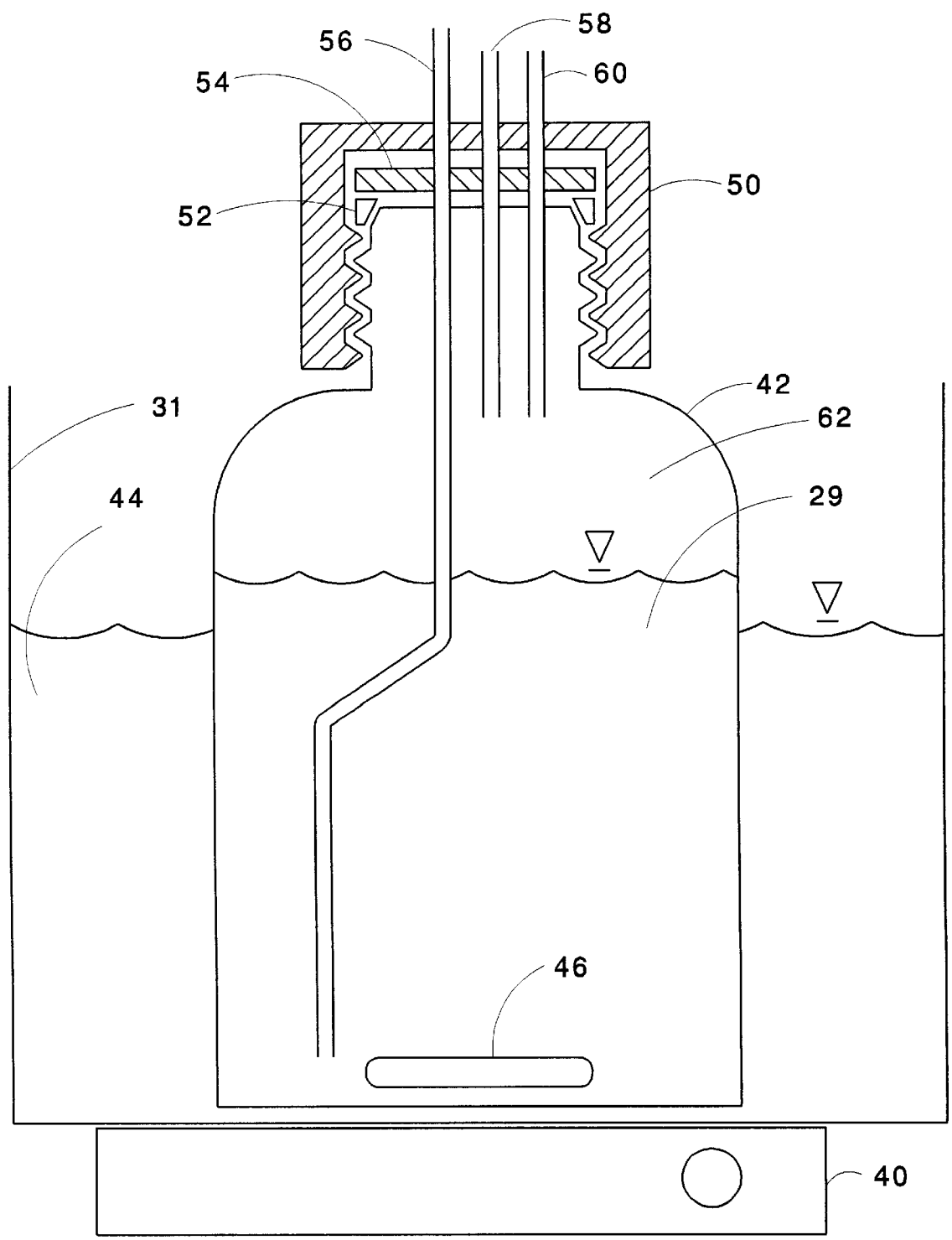
FIG. 8 is a vertical cross-section view of a preferred embodiment of a growth environment subassembly.

The growth-environment subassembly was comprised of the reactor vessels 309, the reference standards 300 and 302, connecting "plumbing" 350 and 352, and the water bath 312. Referring to FIG. 8, the reactors were comprised of one-liter autoclavable glass screw-top bottles 42, custom-fabricated stainless steel bulkheads 54 and plastic tops 50 with teflon seals. Each reactor contained a magnetic stir bar 46. Referring back to FIG. 13, the bulkhead had three small ports (¼-20 threads per inch) and one large port (⅛-inch NPT). Two of the ports were connected to stainless steel tubes (1/16 inch ID) which extended into the glass vessel; the long tube was used to withdraw liquids and the short tube was used for gas pressurization. The additional two ports were used for pressure gauges and possible auxiliary sensors. Each reactor was weighted with a two-pound lead ring (not shown) to reduce its buoyancy in the water bath 312. The calibration-standard vessels were identical to the reactor vessels, except their bulkheads contained only two ports: one for gas pressurization and one for liquid withdrawal.

The water bath consisted of a 30-gallon rectangular polyethylene tank 314, a 200-watt submersible heater 336 and a circulation pump (not shown). The purpose of the water bath was to maintain the reactors and standards at a constant fixed temperature. The water bath also provided a low-oxygen barrier between the system components and atmospheric oxygen. The tank was modified by the installation of an 11-inch×18-inch viewing port (not shown), which is useful for detecting plumbing leaks, monitoring biofouling of plumbing and checking growth in the reactors. The bottom of the bath contained a plate (not shown) with cutouts to hold and position 16 glass vessels. The water tank was mounted on an external wooden base (not shown) which was fitted for 16 magnetic stir plates 338. When the water bath is assembled, the vessels are correctly positioned above the stir plates.

Figure 13:
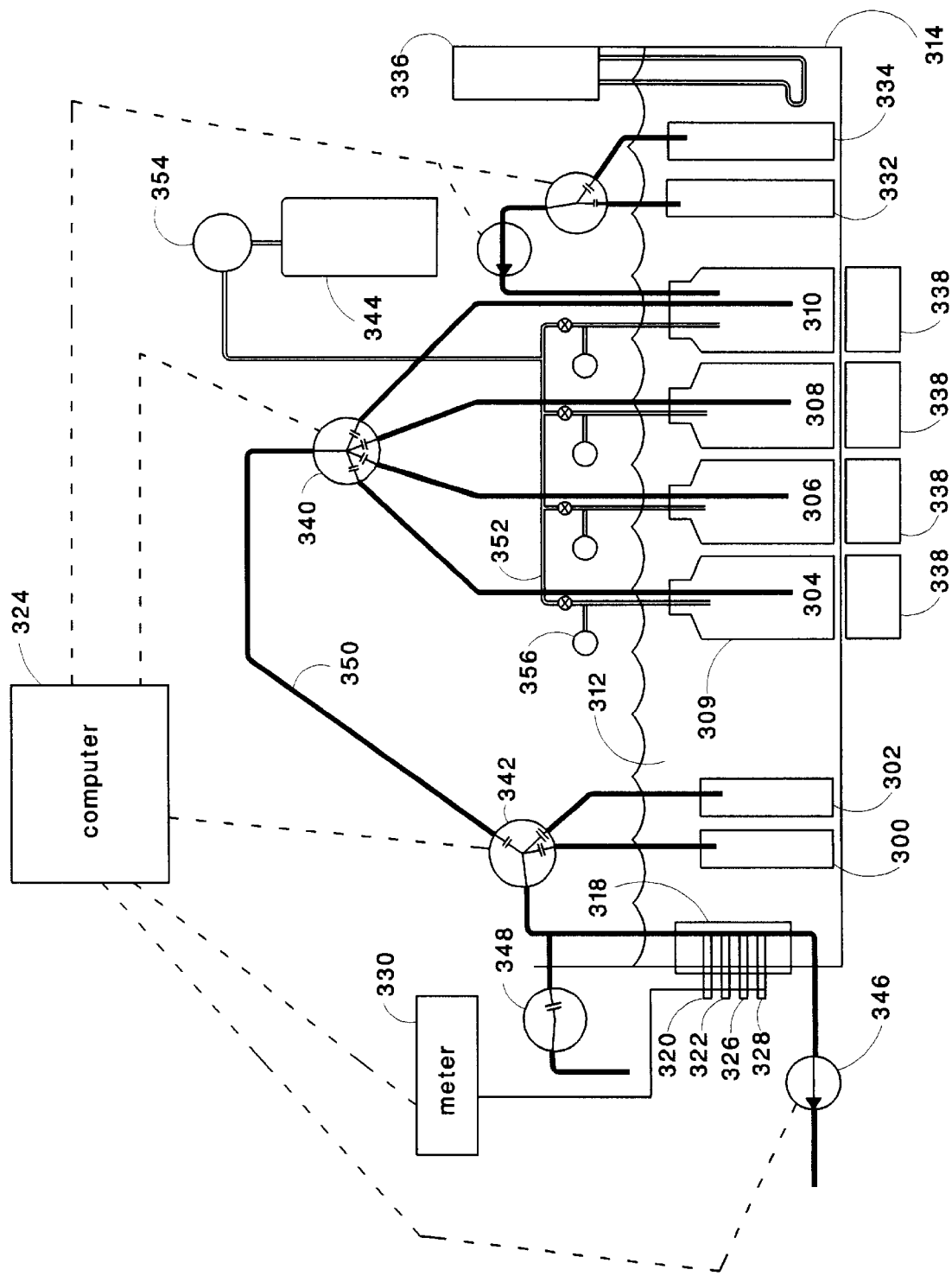
FIG. 13 is a schematic drawing of the working model.

Fluid was transferred from a vessel 309 to the probe manifold 318 by actuating first solenoid valve 340 and second solenoid valve 342. Driving force for the flow was supplied by the system gas pressure. Flow rate through the manifold was set by adjusting a needle valve (not shown) while observing drops per second of the effluent into a graduated cylinder. For some runs, the needle valve was replaced by a precision variable-flowrate peristolic pump 346. This pump is shown in FIG. 13 at the outlet side of the probe manifold, but was placed at the inlet side of the manifold for some runs, in order to compare probe performance with the measured fluid at different pressures.

Samples are collected by actuating third solenoid valve 348 which is connected via Teflon™ tubing to a 20-gauge syringe needle (not shown). The vessel-selector solenoid valves 340 and 342 consist of two identical devices, each with four normally-off inputs and one output. The wetted parts are hydrocarbon-resistant Teflon™ with a very low internal dead volume.

Fluid plumbing 350 was accomplished with 1/16-inch ID Teflon™ fluorinated ethylene polypropylene tubing. Gas plumbing 352 was made with Tygon™ tubing, which is easily clamp-sealed during hookups. Teflon™ compression fittings (not shown) were used on glass vessels and solenoid valves. All liquids in the system were held under nitrogen gas at approximately 5 psi (pounds per square inch). The gas supply system was comprised of a gas cylinder 344, a regulator 354, a pressure gauge (not shown) and a sensitive flow meter (not shown). The purpose of the flow meter is to detect system leaks.

The measurement subsystem comprised the ion-specific electrodes 320, 322, 326, and 328, and manifold 318, independent ion-chromatography measurements and pressure sensors 356. The four parameters of nitrate, chloride, ORP (oxidation/reduction potential) and pH were monitored with said electrodes. In order to optimize accuracy and resistance to the media, glass-body, double-junction probes were used. The pH and ORP probes contained preamplifiers to reduce noise. The probe outputs were read and converted to digital values with a commercial meter 330 which is controlled through the RS-232 port of computer 324. Water bath temperature was monitored with a temperature probe (not shown) connected to the meter 330.

The four probes were mounted in a custom-manufactured manifold 318. The manifold 318 was manufactured of transparent acrylic resin. This material was chosen for the prototype so that potential problems (bubbles, stagnant zones, etc.) could be monitored during the initial test runs.

The manifold was constructed in two pieces. The top piece provided mechanical support and protection for the fragile glass probe bodies. Bulkhead cable clamps (not shown) mounted in the top manifold section were used to secure each probe against "blow-out" forces produced by the fluids being measured. The two manifold sections were joined with stainless steel machine screws (not shown).

The measuring electrodes on the bottom of each of the four probes 320, 322, 326, and 328 varied radically in shape and size. In order to minimize dead volume around the measuring electrodes of the probes, the lower manifold was machined to fit each probe type. Fluid seals were achieved with nitrile o-rings (not shown) installed between each probe and the lower manifold section as close as practical to each probe's measuring electrode. The lower section would have been replaced with a similar Telfon™ piece if long-term exposure to the fluids proves detrimental to the acrylic.

Analyses of nitrate, chloride and acetate concentrations were performed on a Dionex DX100 ion chromatograph using a conductivity detector in conjunction with an anion suppressor and an IonPac column. Measurements were performed at the Center for Biofilm Engineering at Montana State University-Bozeman, Mont. Samples were cooled to 4° C. during storage and held less than seven days prior to analysis.

Reactor gas pressure was monitored with temperature-compensated silicon sensors 356 connected to the reactor bulkhead ports. The sensors were calibrated prior to each run by measuring their outputs at two known pressures (atmospheric and 10 psi). These values were used to convert millivolt outputs to psi readings by algorithms in the software. When gas pressure data were recorded, the reactors were isolated from the nitrogen supply gas after initial filling.

The computer 324 consisted of an 80486 IBM-compatable PC with an internally-mounted peripheral interface card and an external solid-state relay board (not shown). The interface card was used to provide digital outputs and to read analog and digital input signals. The TTL logic-level digital outputs were used to control solenoid valves and pumps. The relay board contained transistor switches to drive the 12-VDC solenoid valves and SCR's (silicon-controlled rectifiers) to drive the 110-VAC pumps. Analog inputs consisted of signals from the solid-state pressure transducers. These signals were converted to digital values by the interface board.

The system software was responsible for measurement and control functions. Measurement activities included collecting, organizing and reporting of measured data. Control functions included switching of valves and pumps and addition of pH buffers and nutrient solutions to maintain steady-state reactor conditions.

Coding was done in the C++ language using object-oriented techniques for both design and code generation. The graphical user interface is Windows™ compatible. The user interface was designed to be user-friendly with the target user type (research scientists and engineers). A copy of the C++ source code is attached in Appendix A.

User-interface specifications were presented to several potential users of the apparatus prior to final design. These individuals were graduate student microbiologists and environmental engineers with "hands-on" experience with aerobic respirometers and anaerobic experimentation. Results of these interviews indicated that the following features were strongly desired:

1. A user-friendly initial screen to select major program subareas such as experiment set-up, initiate data collection, print data, etc.
2. A set-up screen which allows user to select parameters for calibration, run time, etc.
3. A screen display of real time graphs (measured parameters versus time) during a run.
4. Bioprocess model parameter estimating capability for a range of widely-used models.
5. Numerical storage of measured values in a spreadsheet format for easy export and printing. The software was comprised of five distinct types of classes or components: a basic user interface, objects representing pumps and valves, several views of the data itself, an RS-232 communication component and a database component. Each class is described below.

The first component, the user interface, was implemented in version 1.5 of Microsoft's Visual C++. Microsoft Foundation Class (MFC) components were used to provide a standard windows-compliant interface (Microsoft, 1994, *Introducing Visual C++: Development System for Windows™ and Windows NT™, Version* 2.0. U.S.A.: Microsoft Corporation).

The second component, pumps and valves, were the main custom objects in the software. These C++ objects encapsulated the activities associated with their real-world counterparts. They included methods for turning objects on and off. Each pump or valve object also included a timer and visual component so they could be turned on for specific periods of time and provide feedback to the user.

The third component was the views of the data. The software architecture employed a standard Document-View model for Windows programming. In the working model, there was one set of data (Document) and several ways of looking at it (Views). MFC was used to provide the main view, current probe readings, time until next sample, etc. Graphics Server from Pinnacle was used to provide the time vs. value graphs (Pinnacle, 1993, *Graphics Server SDK: Graphing Toolkit for Windows™*, U.S.A.: Pinnacle Publishing, Inc.). GRID VBX, a Visual Basic Control (VBX), was used to provide the spreadsheet view of the data.

The fourth component of the software was the RS-232 serial communications portion. This component was used to communicate with the equipment which interfaces to the probes. A simple state machine was used to control the remote device. GreenLeaf's COMM++ Asynchronous Communications Library (Version 2.0) was used to handle the actual serial communications (Greenleaf Software, Inc., 16479 Dallas Parkway #570, Dallas, Tex. 75248). This component is compiled as a Dynamic Link Library (DLL).

The final component of the software architecture was the C++ containers used to store data. The data objects in these containers were persistent, meaning that they could be stored on disk and read back in at a later date. The data was not user-editable, but could be exported in a variety of standard formats for further manipulation.

Measurement sequences controlled by the software were initiated at user-specified intervals based on an internal timer. Pump and valves used in the measurement sequence were operated by setting specific output ports high for a specified time interval, then resetting them to low.

During runs where constant-pH and/or constant-nitrate conditions were maintained in a specific reactor, probe readings were compared to "setpoint" values during each measurement. If a measured value varied from a setpoint value by more than a preset amount (+0.2 units for pH, minus 50 ppm for nitrate), then a fixed quantity of appropriate concentrate was added to the reactor by switching on a pump and valve combination for a fixed period of time (10 seconds).

Each experiment used a minimum of three active reactors and one sterile control. Calibration standards consisted of high and low reference solutions for the nitrate and chloride probes. All experiments were run in the "nitrate depletion" mode (i.e., nitrate titrant was not added during the runs; instead, changes in nitrate concentrations were monitored).

Media formulations for the toluene medium, TCE medium, trace minerals and reductant are shown in Tables 18–21. Separate media formulations were developed for toluene and TCE biodegradation experiments. The media provide the carbon source and all the necessary minerals and vitamins for denitrifying organisms to grow efficiently.

TABLE 18

Toluene Mineral Media

| Constituent | Concentration, mg/l[a] |
|---|---|
| Potassium phosphate (mono) | 867 |
| Potassium phosphate (di) | 540 |
| Potassium nitrate | 150 |
| Ammonium sulfate | 996 |
| Magnesium sulfate | 198 |
| Trace minerals | 10 ml |
| Toluene | variable |
| Distilled water | 990 ml |

[a]Except where noted

TABLE 19

TCE-Acetate Mineral Media

| Constituent | Concentration, mg/l[a] |
|---|---|
| Potassium phosphate (mono) | 867 |
| Potassium phosphate (di) | 540 |
| Potassium nitrate | 785 |
| Ammonium sulfate | 996 |
| Magnesium sulfate | 198 |
| Acetate | 300 |
| Trace minerals | 10 ml |
| TCE | variabie |
| Distilled Water | 990 ml |

[a]Except where noted

TABLE 20

Trace Mineral Solution

| Constituent | Concentration, mg/l[a] |
|---|---|
| Calcium sulfate | 2,000 |
| Iron(II) sulfate | 1,000 |
| Manganese sulfate | 500 |
| Sodium molybdate | 100 |
| Copper sulfate | 100 |
| 0.1 N Sulfuric acid in distilled water | 1000 ml |

[a]where noted

TABLE 21

Reductant Solution

| Constituent | Concentration (mg/L) |
|---|---|
| Resazurin | 300 |
| Sodium dithionite | 1,000 |
| Sodium sulfide | 12,000 |

Water bath temperature was maintained at 30° C. Probe readings were recorded and ion chromatography (IC) samples were collected at 6 to 24-hour intervals, and gas chromatograph (GC) samples were collected at approximately 48-hour intervals during each run. The first experiment (Experiment A) comprised four reactors: a toluene medium sterile control (Reactor 1), a toluene sample (Reactor 2) and two acetate/TCE samples (Reactors 3 and 4). During a second experiment (Experiment B), additional TCE data were collected. Reactors included an acetate/TCE medium control (Reactor 2), an acetate/TCE medium with acetate but no TCE (Reactor 3) and an acetate/TCE sample (Reactor 4). The toluene control and sample (Reactor 1) from Experiment A remained in the water bath during the second experiment because further degradation was expected. Experiment C reactors consisted of a sterile acetate/TCE control (Reactor 1), an inoculated acetate/TCE sample (Reactor 2), a sterile toluene control (Reactor 3) and an inoculated toluene sample (Reactor 4).

Figure 14:
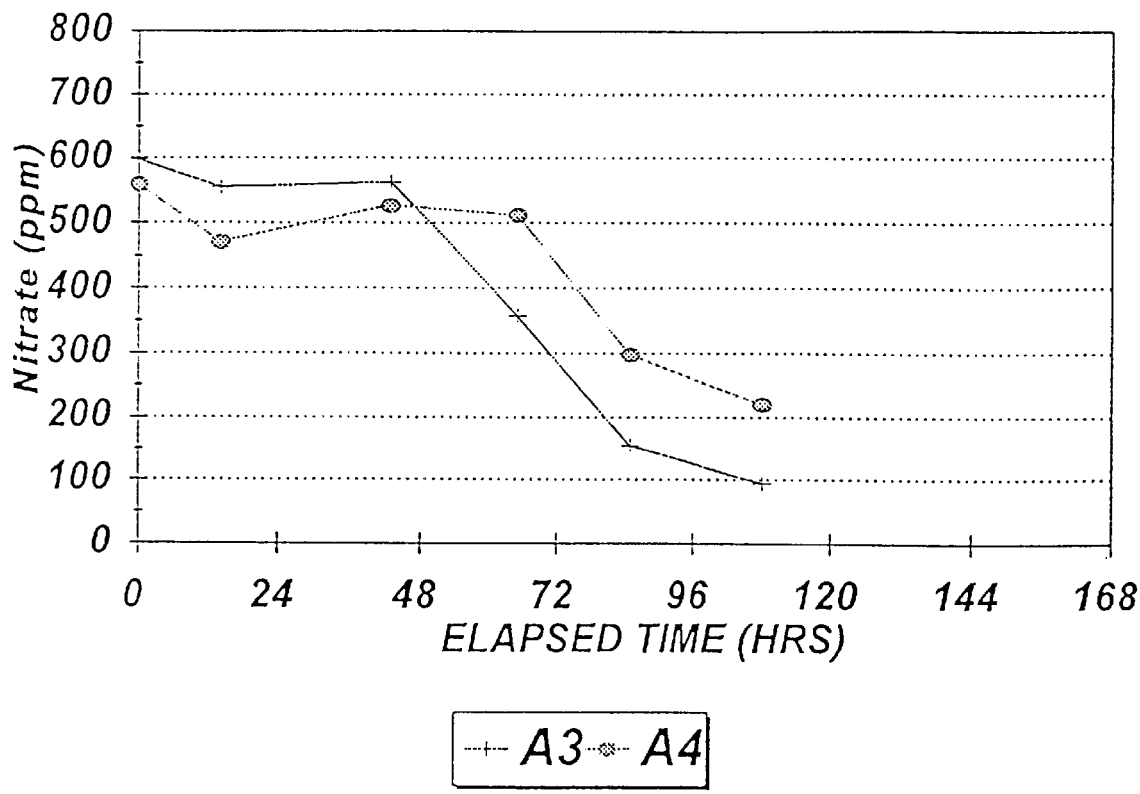
FIG. 14 is a graph showing the electron acceptor (nitrate) uptake versus time for two similar reactors operating simultaneously.
Figure 15:
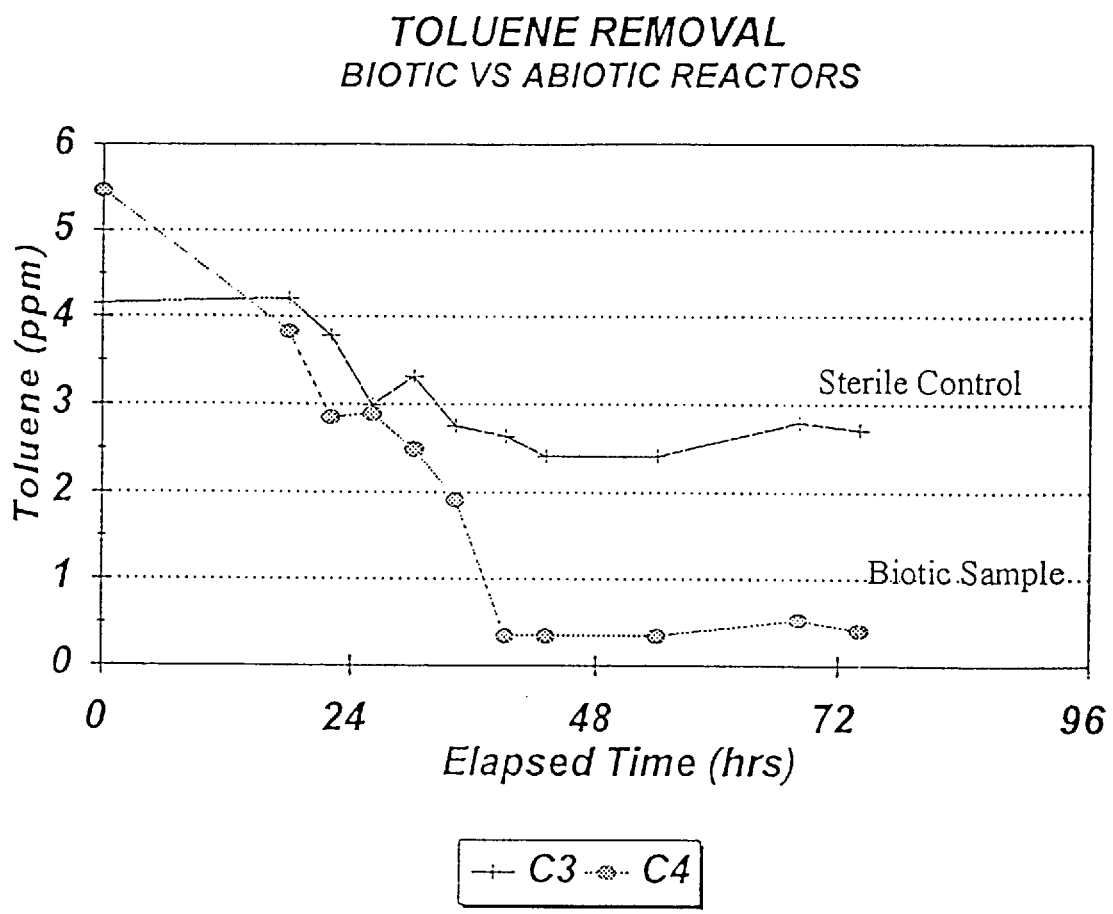
FIG. 15 is a graph showing the substrate (toluene) removal versus time for a sterile control and a biotic reactor.
Figure 16:
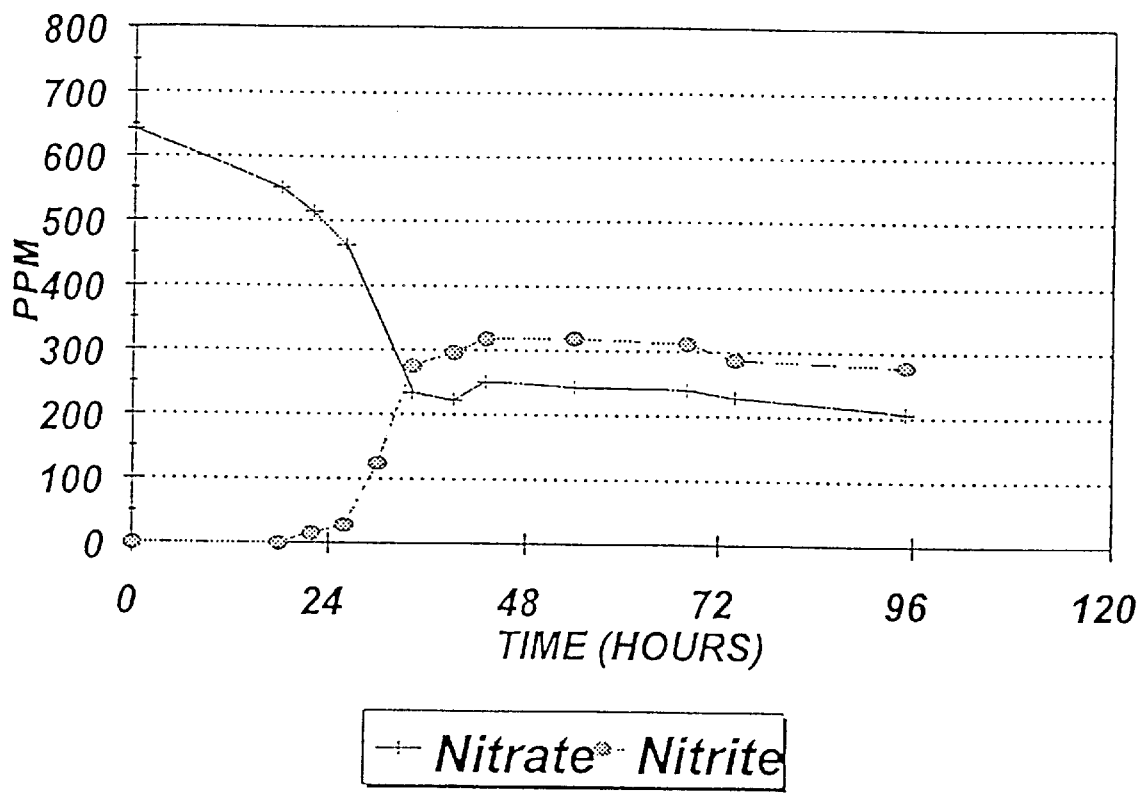
FIG. 16 is a graph showing the electron acceptor (nitrate) uptake and product (nitrite) production versus time for a single reactor during an experimental run.

Experimental results are summarized graphically in FIGS. 14, 15 and 16. Each graph curve represents an individual reactor run. The graph legends identify the experiment and reactor (i.e., curve A3 represents Experiment A, Reactor 3).

As illustrated in FIG. 14, measurements using an ion chromatograph sensor show similar behavior for the two reactors. Nitrate concentrations decreased from approximately 600 ppm to 150 ppm during the run. Both curves indicate a slow "lag phase" followed by a fast linear phase as expected.

Reductions in hydrocarbon concentrations during an experimental run are due to both biotic and a biotic processes. Abiotic processes include losses due to leaks of the volatile compounds from the system and adsorbtion of the compounds onto components of the system such as reactor walls and tubing. Losses due to abiotic removal are determined by running a sterile control sample in parallel with active samples. FIG. 15 shows data for the most volatile of the compounds studied (toluene). This graph shows that the biotic removal was significantly greater than abiotic losses in the working model, but that abiotic losses can be expected in studies of this type.

The results of ion-chromatography measurement performed during Experiments B and C were analyzed to shed light on the stoichiometries of the oxidation-reduction reactions under study. The results of this analysis are presented in Table 22. Those results plus illustration of the changes in nitrate and nitrite concentrations over time illustrated in FIG. 16 confirm that nitrate used during denitrification was converted, at least in part, to nitrite, thus clarifying the stoichiometry of the reactions monitored.

The fact that the working model could be used to collect data upon which estimates of reaction kinetics (rates) could be based is illustrated in FIGS. 15 and 16. The utility of the invention is illustrated by comparing the uncertainty of rate data collected by the anaerobic respirometer to the uncertainty of equivalent data collected by conventional, manual methods. This comparison was made by comparing decrease rates of nitrate, acetate and toluene measured using the anaerobic respirometer to the toluene degradation rate from a similar experiment where GC analyses were made on manually-collected headspace samples. Specifically, the 95 percent confidence interval of the slope of a linear curve fitted through concentration-versus-time data points for the respirometer data (expressed as a percent of the slope) was compared to the 95 percent confidence interval of the slope of a linear curve fitted through toluene concentration versus time data points (expressed as a percent of the slope) for the manually collected data.

The results of a statistical analyses of these data presented in Tables 23 and 24 indicated an average standard error of 0.91 percent of the slope of the respirometer data, and 4.25 percent of the slope of the manually-collected data. Therefore, the working model was able to significantly increase the reliability of a bioremediation design over the use of traditional methods.

Many variations in configurations have been discussed and others will occur to those skilled in the art. Some variations within the scope of the claims include network implementations of the invention. All such variations within the scope of the claims are intended to be within the scope and spirit of the present invention.

TABLE 22

Reaction Stoichiometries

| Experiment/ reaction | Component | Component type | Starting concentration mg/l | Starting concentration mM | Ending concentration mg/l | Ending concentration mM |
|---|---|---|---|---|---|---|
| B3 - Acetate denitrification | Acetate | Electron donor | 650 | 11 | 0 | 0 |
| | Nitrate | Electron donor | 490 | 8.0 | 225 | 3.7 |
| | Nitrite | Product | 0 | 0 | 90 | 2.0 |
| B4 - Acetate denitrification with TCE degradation | Acetate | Electron donor | 650 | 11 | 0 | 0 |
| | Nitrate | Electron acceptor | 500 | 8.0 | 55 | 0.9 |
| | Nitrite | Product | 0 | 0 | 82 | 1.8 |
| C2 - Acetate denitrification with TCE degradation | Acetate | Electron donor | 540 | 9 | 0 | 0 |
| | Nitrate | Electron acceptor | 640 | 11 | 240 | 3.8 |
| | Nitrite | Product | 0 | 0 | 280 | 6.0 |

TABLE 23

Respirometer Data Analysis

| Analyte | Analysis method | 95% Confidence interval (percent of value) |
|---|---|---|
| Nitrate | IC: automatic collection | 1.64 |
| Acetate | IC: automatic collection | 0.39 |
| Toluene | GC: automatic collection | 0.71 |
| Average | — | 0.91 |

TABLE 24

Manual Data Analysis

| Analyte | Analysis method | 95% Confidence interval (percent of value) |
|---|---|---|
| Toluene | GC: manual headspace collection | 4.2 |
| Toluene | GC: manual headspace collection | 2.1 |
| Toluene | GC: manual headspace collection | 6.4 |
| Average | — | 4.2 |

We claim:

1. An apparatus for respirometry comprising at least one chamber adapted to provide an anaerobic environment for batch culture of a microorganism in a liquid, said microorganism capable of consuming a dissolved electron acceptor other than molecular oxygen during growth on a substrate having a known initial and a measured final substrate concentration to produce suspended biomass;

means for sensing the concentration of said dissolved electron acceptor in said liquid, said means for sensing the concentration of said dissolved electron acceptor having a first output;

means for measuring the concentration of said suspended biomass at the beginning and at the end of said growth, said means for measuring the concentration of said suspended biomass having a second output; and means for converting said first output and said second output into kinetic and stoichiometric bioprocess model parameters.

2. The apparatus of claim 1 further comprising means for monitoring and controlling the temperature of said environment.

3. The apparatus of claim 1 further comprising means for monitoring and controlling the pH of said liquid.

4. The apparatus of claim 1 further comprising
   means for sensing the concentration of a dissolved product produced by said microorganism in said liquid, said means for sensing the concentration of a dissolved product having a third output; and
   means for converting said third output into one of the stoichiometric parameters of said bioprocess model, wherein said stoichiometric parameter is converted into and expressed in electron mole units.

5. The apparatus of claim 1 wherein said means for sensing the concentration of said electron acceptor in said liquid comprises at least one element selected from the group consisting of
   an ion-selective electrode,
   a pH electrode,
   a oxidation-reduction potential electrode, and
   an ion chromatograph.

6. The apparatus of claim 1 further comprising
   a computing device having a memory;
   a first set of instructions for execution in said computing device for providing a user interface;
   a second set of instructions for execution in said computing device for collecting, organizing and reporting said first output and said second output;
   a third set of instructions for execution in said computing device for using said first output and said second output for calibrating at least one of the stoichiometric parameters of said bioprocess model in electron mole units.

7. The apparatus of claim 6 wherein said bioprocess model is at least one model selected from the group consisting of
   a metabolism model, and
   a cometabolism model.

8. An apparatus for anaerobic respirometry comprising
   means for batch culture of at least one microorganism in a liquid, said means for batch culture being adapted to exclude molecular oxygen, and said microorganism requiring a dissolved electron acceptor other than molecular oxygen for growth on a substrate in accordance with a known stoichiometry, wherein said dissolved electron acceptor is selected from the group consisting of
   nitrate,
   nitrite,
   nitric oxide,
   nitrous oxide,
   iron,
   sulfate,
   acetate,
   formate,
   methanol,
   methylamine,
   dimethylamine,
   trimethylamine,
   carbon monoxide, and
   carbon dioxide,
   means for measuring the uptake of said dissolved electron acceptor to produce a plurality of electron acceptor uptake data; and
   computer means for analyzing said known stoichiometry and said plurality of electron acceptor uptake data to produce a plurality of stoichiometric and kinetic bioprocess model parameters.

9. The apparatus of claim 8
   wherein said means for batch culture is not adapted for measurement of undissolved gas production or consumption by said at least one microorganism; and
   wherein said plurality of stoichiometric and kinetic bioprocess model parameters are selected from the group consisting of
   a maximum specific growth rate,
   a half saturation constant,
   a maintenance coefficient,
   an inhibition coefficient, and
   a truth growth yield.

10. A method for anaerobic respirometry comprising the steps of
    adapting at least one chamber to provide an anaerobic environment for batch culture of a microorganism in a liquid, said microorganism capable of consuming a dissolved electron acceptor other than molecular oxygen during growth on a substrate having a known initial substrate concentration and a measured final substrate concentration to produce suspended biomass;
    sensing the concentration of said dissolved electron acceptor other than molecular oxygen in said liquid with a means for sensing having a first output;
    measuring the concentration of said suspended biomass at the beginning and at the end of said growth with a means for measuring having a second output; and
    converting said first output and said second output into kinetic and stoichiometric bioprocess model parameters,
    wherein the concentration of said dissolved electron acceptor is sensed at least one hundred times more than the concentration of said substrate is measured.

11. The method of claim 10 further comprising the step of monitoring and controlling the temperature of said environment.

12. The method of claim 10 further comprising the step of monitoring and controlling the pH of said liquid.

13. The method of claim 10 further comprising the steps of
    sensing the concentration of a dissolved product produced by said microorganism in said liquid with means for sensing the concentration of a dissolved product and converting said concentration of a dissolved product into other than chemical oxygen demand (COD) units, said means for sensing the concentration of a dissolved product having a third output; and
    converting said third output into said bioprocess model parameters.

14. The method of claim 13 wherein said means for sensing the concentration of a dissolved product comprises at least one element selected from the group consisting of
    an ion-selective electrode,
    a pH electrode,
    a oxidation-reduction potential electrode, and
    an ion chromatograph.

15. The method of claim 10 further comprising the steps of
    executing a first set of instructions for execution in a computing device for providing a user interface;
    executing a second set of instructions for execution in said computing device for collecting, organizing and reporting said first output;
    executing a third set of instructions for execution in said computing device for using said first output for calibrating a bioprocess model.

16. The method of claim 15 wherein said bioprocess model is at least one model selected from the group consisting of a metabolism model, and a cometabolism model.

17. The method of claim 10 wherein said model parameters are selected from the group consisting of a maximum specific growth rate, a half saturation constant, a maintenance coefficient, an inhibition coefficient, and a true growth yield.

18. A method for anaerobic respirometry comprising the steps of providing an environment for batch culture of a microorganism in a liquid, said microorganism capable of consuming a dissolved sulfate as an electron acceptor during growth on a substrate to produce suspended biomass;

sensing the concentration of said dissolved electron acceptor during said growth and producing a first output;

determining the concentration of said substrate at the beginning of said growth with means for producing substrate data;

measuring the concentration of said suspended biomass at the end of said growth with means for producing biomass data; and converting said first output, said substrate data and said biomass data into kinetic and stoichiometric bioprocess model parameters.

19. The method of claim 18 further comprising the step of monitoring and controlling said concentration of said dissolved electron acceptor by adding said electron acceptor to said liquid.

* * * * *